US007557199B2

(12) United States Patent
Ramareddy et al.

(10) Patent No.: US 7,557,199 B2
(45) Date of Patent: Jul. 7, 2009

(54) HEPATITIS C VIRUS VACCINE

(75) Inventors: Guntaka Venkata Ramareddy, Memphis, TN (US); Chittoor Mohammad Habibullah, Andhra Pradesh (IN); Mohammad Nanne Khaja, Andhra Pradesh (IN); Chandra Madhavi, Andhra Pradesh (IN)

(73) Assignee: Sudershan Biotech Ltd., Andhra Pradesh (IN)

( * ) Notice: Subject to any disclaimer, the term of this patent is extended or adjusted under 35 U.S.C. 154(b) by 0 days.

(21) Appl. No.: 11/979,440

(22) Filed: Nov. 2, 2007

(65) Prior Publication Data

US 2008/0145915 A1 Jun. 19, 2008

Related U.S. Application Data

(62) Division of application No. 11/447,049, filed on Jun. 6, 2006, now Pat. No. 7,348,011.

(60) Provisional application No. 60/689,090, filed on Jun. 10, 2005.

(51) Int. Cl.
*C12N 15/11* (2006.01)
*C12N 7/00* (2006.01)

(52) U.S. Cl. .................................. 536/23.1; 435/235.1

(58) Field of Classification Search ....................... None
See application file for complete search history.

(56) References Cited

FOREIGN PATENT DOCUMENTS

| | | | |
|---|---|---|---|
| EP | 1 481 984 | A1 | 12/2004 |
| WO | WO 02/097091 | | 12/2002 |

OTHER PUBLICATIONS

Broor et al., Analysis of genetic variability of Indian isolates of Hepatitis C virus, Arch. Virol., 2004, 149:1185-1192.*
Panigrahi et al., Genotype Determination of Hepatitis C Virus From Northern India: Identification of a New Subtype, Journal of Medical Virology, 1996, 48:191-198.*
NCBI Report Q6DQ94 (submitted Jun. 2004 and created Aug. 16, 2004).
Huang et al., Recent development of therapeutics for chronic HCV infection, Antiviral Research, 2006, 71:351-362.

* cited by examiner

*Primary Examiner*—Bruce Campell
*Assistant Examiner*—Nicole Kinsey White
(74) *Attorney, Agent, or Firm*—Oliff & Berridge, Plc.

(57) ABSTRACT

The present invention relates to isolation of a novel Hepatitis C virus, more particularly, the present invention relates to a viral class Hepatitis C, polypeptides, polynucleotide, vaccine and antibodies derived there from.

5 Claims, 48 Drawing Sheets

HCV – CORE Protein

1 – Whole cell pellet without induced protein

2 – Whole cell pellet with induced protein

3 – Protein Marker (from top to bottom 116, 66.2, 45, 35, 25, 18.4 and 14.4 kDa)

4 – Purified CORE Protein

HCV - NS3 Protein

1 - Whole cell pellet with out induced protein

2 - Whole cell pellet with induced protein

3 - Protein Marker (from top to bottom 116, 66.2, 45, 35, 25, 18.4 and 14.4 kDa)

4 - Purified NS3 Protein

HCV - NS4 PROTEIN

1 - Whole cell pellet without induced protein

2 - Whole cell pellet with induced protein

3 - Protein Marker (from top to bottom (116, 66.2, 45, 35 and 25 kDA)

4 - Purified NS4 protein

HCV - NS5 protein

1 - Whole cell pellet without induced protein

2 - Whole cell pellet with induced protein

3 - Protein marker (from top to bottom 116, 66.2, 45, 35, 25, 18.4 kDa)

4 - Purified NS5 protein

Fig. 9

5'UTR: 341 bases – SEQ ID No. 3

CORE: 573 bases – SEQ ID No. 5 and corresponding polypeptide (SEQ ID No.6)

E1: 576 bases – SEQ ID No. 7 and corresponding polypeptide (SEQ ID No.8)

E2/NS1: 1278 bases – SEQ ID No. 9 and corresponding polypeptide (SEQ ID No.10)

NS2: 591 bases – SEQ ID No. 11 and corresponding polypeptide (SEQ ID No.12)

NS3: 1953 bases – SEQ ID No. 13 and corresponding polypeptide (SEQ ID No.14)

NS4: 945 bases – SEQ ID No. 15 and corresponding polypeptide (SEQ ID No.16)

NS5: 3117 bases – SEQ ID No. 17 and corresponding polypeptide (SEQ ID No.18)

3'UTR: 67 bases– SEQ ID No. 4

AY651061: 5' UTR:

gccagccccctgatgggggcgacactccgccatgaatcactcccctgtgaggaactactgtcttcacgcagaaagcgtct
agccatggcgttagtatgagtgtcgtgcagcctccaggaccccccctcccgggagagccatagtggtctgcggaaccggt
gagtacaccggaattgccaggacgaccgggtcctttcttggataaacccgctcaacgcctggagatttgggcgtgccccc
gcaagactgctagccgagtagtgttgggtcgcgaaaggccttgtggtactgcctgatagggtgcttgcgagtgccccggg
aggtctcgtagaccgtgcacc

AY651061: CORE:

atgagcacgaatcctaaacctcaaagaaaaaccaaacgtaacaccaaccgtcgcccacaggacgtcaagttcccgggtg
gcggacagatcgttggtggagtttacttgttgccgcgcaggggccctagattgggtgtgcgcgcgacgaggaagacttcc
gagcggtcgcaacctcgaggtagacgtcagcctatccccaaggcacgtcggcccgagggcaggacctgggctcagcccgg
gtacccttggcccctctatggcaatgagggctgcgggtgggcgggatggctcctgtctccccgcggctctcggcctagtt
ggggccccacagacccccggcgtagatcgcgcaatttgggtaaggtcatcgatacccttacgtatggcttcgccgacctc
atggggtacataccgctcgtcggcgccccccttgggggcgctgccagggccctggcgcacggcgtccgggtcctggaaga
cggcgtgaactatgcaacagggaaccttcctggttgctctttctctatcttccttctggccctgctctcttgcttgactgtgcccgcttc
ggcc

AY651061: E1:

gtcggagtgcgcaactcttcgggggtgtaccatgtcaccaatgattgccccaatgcgtctgttgtgtacgagacagatagcttgat
catacatctgccggggtgtgtgccctgcgtacgcgagggcaacggttcgaggtgctgggtctcccttagtcctactgttg
ccgctaaggatccgggcgtcccggtcaacgagattcggcgtcacgtcgacctgattgccggggccgctgcattctgttcg
gctatgtatgtagggcacttatgcggttccatcttcctcgttggccagcttttcaccctctcccctaggcgccactggacaacacaa Fig. 9 continued AY651061: E1 gactgtaattgctccatctacccaggacatgtgacaggccatcgaatggcttgggacatgatgatgaactggtcccctacgac
ggcgctggtagtagcccagctgctccggatcccacaagccatcttggacatgatcgctggtgctcactggggagtcctgg
cgggcatagcgtatttctccatggtggggaactggacgaaggtcctggtagtgctgctgctatttgccggcgtcgacgcg

AY651061: E2/NS1:

acgaccatcgtctccgggggaagtgccggccgcagcacggctggacttgttgggctcttctcaccaggcgcccggcagaa
catccagctgatcaacaccaacggcagttggcacatcaaccgcacggccctgaactgcaatgataccccttcaaaccggct
gggtagcagggcttttctataccaacaaattcaactcttcgggttgccccgagaggttggccagctgccgaccccttgcc
gactttgaccagggctggggccctatcagttataccaacggaagcggccccgaccaacgcccctactgctggcactaccc
cccaaaaccttgtggtattgtgcccgcagagagcgtgtgtggcccagtatactgcttcactcccagccccgtggtggtgg
gaacgaccgacaggtcgggcgcgcccacctacaactggggtgaaaatgaaacggacgttttcgtcctcaacaacaccagg
ccacggctgggcaattggttcggtggtacctggatgaactcaactggattcaccaaggtgtgcggagcgccccccttgtgc
catcggaggggtgggcaacaacaccttgtactgccccactgattgtttccgcaaacatccggaagccacgtactctcggt
gcggctccggtccttggattacacccaggtgcttgatccactacccgtataggctttggcattatccttgtaccatcaat
tacaccatattcaagatcaggatgtttgtgggcggggttgagcacaggctcgacgccgcgtgcaactggacgcggggaga
gcgctgcgacttggacgacagggatcgggccgagttgagccctctgttgctgtccactacgcaatggcaggtcctcccct
gctcattcacaacactgcccgccctgtcaactggcctgatacatctccaccagaacatcgtggacgtgcagtacctctat
gggttgagctcggcagtcacatcctgggtcataaagtgggagtacgttgtgctcctcttcttgctgctagcagatgctcg
catttgtgcctgcttgtggatgatgcttctcatatctcaggtagaggcggcgctggagaacttgatagttctcaacgctgcttcccta
gtcgggacacatggcatcgtccccttcttcatctttttttgtgcagcttggtacctaaaaggcaagtgggcccctggactcgcctatt
ccgtctatgggatgtggccactgctcctgcttctcctggcgttgccccaacgggcatacgcc

AY651061: NS2:

ttggatcaggagttggccgcgtcgtgtggggccacggtcttcatctgcctagcggtgctcactctatcgccatattacaaac
agtacatggcccgcggcatctggtggctgcagtacatgctgaccagagcagaggcgctcctacaggtttgggtcccccg
ctcaacgcccgaggagggcgcgacggagtcgtactgctcacgtgtgtgctccacccgcacttgctctttgaaatcaccaa
gatcatgctggccattctcgggcctttgtggatcttgcaggccagtctgctcaaggtaccgtacttcgtgcgcgttcagg
gccttctccggatctgcgcgctagcgcggaagatggtcggaggccattacgtgcaaatggtcaccatcaagttaggggcg
ctcactggcacctatatttataaccatctcactcctcttcgggactgggcgcacaacggcttgcaagacctagccgtagc
tgtggagccagtcgtcttctcccaaatggagaccaagctcatcacgtgggggggcagacacagccgcgtgtggtgacatca
tcaacggcttgcccgtctccgcccgcagg

AY651061: NS3:

ggccaggagatactgctcggaccagccgatggaatggcctctaggggatggaggttgctggcgcccatcacggcgtacgct
cagcagacaaggggcctcctagggtgtataatcaccagcctgactggccgggacaagaaccaagtggagggtgaagtcca
gattgtgtcaactgctgcccaaacgttcttggcgacgtgcatcaacggggtatgctggactgtctaccacggggccggaaccag
gaccattgcatcatccaagggtcctgttattctaatgtataccaatgtagaccaagacctcgggggctggaccgctcctcaagtgc
tcggctcactgacaccctggagctgcggctcctcggacctttacctggtcacgaggcatgccgatgtcattcccgtgccgcggc
gaggtgaaaccaggggcagcctgctttcgccccggcccatttcctatctaaagggatcctcgggaggccccctgctctgtccca
tgggacatgccgtgggcattttcagggccgcggtgtgcacccgtggggtcgcaaaggcggtcgactttgtgcccgttgagtc
cttagagaccaccatgaggtccccagtgtttactgacaattccagccctctaacagtgccccagagttaccaggtggcgcatcta
catgcacccactgggagtggcaagagcacgaaggtgccggccgcttacgcagctcaggggtacaaggtacttgtgctgaacc
cgtctgttgctgccaccttagggttcggtgcttatatgtcaaaggcccatgggatcgacccaaacatcaggaccggcgtgagg Fig. 9 continued AY651061: NS3 accatcaccacaggctcccccatcacctactccacctacggcaaatttttggctgatggcggatgcccaggaggtgcgtacgac
atcataatatgtgacgaatgtcactcagtggacgccacctcgattctgggcatagggaccgtcttggaccaagcggagacggcg
ggggtcaggctcactgtcctcgccaccgctacaccacctggttccgtcaccgtgccacattccaacatcgaggaagttgcactgt
ccgctgacggggaaataccattttatggtaaggccatccccctaaactacatcaagggggggaggcacctcattttctgccactc
caagaagaagtgcgacgagctcgctgcaaagctggtcggtccgggcgtcaacgcggtggcctttaccgtggcctcgacgta
tctgtcattccaactacaggagacgtcgttgttgtagcgaccgacgccttgatgactggcttcaccggagatttcgactctgtgata
gactgcaacacctgtgtcgtccagacagtcgacttcagcctagaccctatattctctattgagacttccaccgtgccccagga
cgccgtgtcccgctcccaacggaggggtaggaccggtcgagggaagcatggtatttacagatatgtgtcacccggggagc
ggccgtctggcatgttcgactccgtggtcctctgtgagtgctatgacgcgggttgtgcttggtacgagcttacacccgcc
gagaccacagtcaggctacgggcatacctcaacaccccaggattgcccgtgtgccaggaccacttggagttctgggagag
tgtcttcaccggcctcacccacatagatgcccacttcctgtcccagacgaaacagagtggggagaacttcccctacctag
tcgcataccaagccaccgtgtgcgctagagctagagctcctcccccgtcatgggaccaaatgtggaagtgcctgatacgg
ctcaagcccaccctcactggggctaccccattactatacagactgggtagtgtacagaatgagatcaccttaacacaccc
aatcacccaatacatcatggcttgcatgtcggcggacctggaggtcgtcact

AY651061: NS4:

agcacgtgggtgttggtgggcggcgtcctagccgctttggccgcttactgcctgtccacaggcagcgtggtcatagtgggcagg
ataatcctaggtgggaagccggcagtcatacctgacagggaggttctctaccgagagtttgatgagatggaggagtgcgccgc
ccacgtcccctacctcgagcaggggatgcatttggcggagcagttcaagcagaaagctcttgggttgctccagacggcatccaa
acaaacagagacgatcactcccattgtccagtctaattggcagaagctcgagtctttctgggctaaacacatgtggaacttcgtta
gcgggatacaatatctggcgggcctatcaacgctgcccgggaaccccgctatagcatcgctgatgtcgtttacggccgcag
tgacgagtccactaaccactcagcagaccctcctctttaacatcttgggggggtggctggctgcccagcttgccgcccca
gccgccgccacagccttcgttggcgcaggcattactggcgccgttgttggcagtgtgggcctagggaaggtcctggtgga
cattcttgccggctacggggctggtgtggccggggccctcgtggctttcaaaatcatgagcggggagacccccaccacgg
aggatctagtcaaccttctgcctgccatcctatcgccaggagctctcgttgtcgccgtggtgtgcgcagcaatactacgccggca
cgtgggccttggcgagggcgccgtgcagtggatgaaccggctgatagcgtttgcttctcggggtaaccacgtctcccctacaca
ctacgtgccggagagcgacgcgtcggctcgtgtcacaccaattctcaccaggctcactgttactcagcttctgaaagggctccac
gtgtggataagctcgaattgcatcgccccgtgt

AY651061: NS5:

gct agttcttggc ttaaagatgt ctggaactgg atatgcgagg
tgctgagcga cttcaagaat tggctgaagg ccaaacttgt accacaactg cccgggatcc
cattcgtatc ctgccaacgc gggtaccgtg gggtctggcg gggcgagggc atcgtgcaca
ctcgttgccc gtgtggggcc aatataactg gacatgtcaa gaacggttcg atgagaatcg
tcgggcctaa gacttgcagc aacacctggc gtgggtcgtt ccccattaac gcttacacta
caggcccgtg cacgccctcc ccggcgccga actatacgtt cgcgctatgg agggtgtctg
cagaggagta tgtggaggta aggcggctgg gggacttcca ttacgtcacg gggtgacca
ctgataaact caagtgtcca tgccaggtcc cctcacccga gttctccaca gaggtggacg
gggtgcgcct gcataggtac gcccctccct gcaaaccccct gctacgggat gaggtgacgt
ttagcgtcgg gttcaatgaa tacctggtgg ggtcccagtt gccctgcgag cccgagccag
acgtagcagc attaacatca atgcttacag acccttccca catcactgca aagacggcgg
cgcgtaggct gaagcggggg tctcccccct ccctggccag ttcttctgcc agccagctgt Fig. 9 continued AY651061 E1 ctggtagtagcccagctgctccggatcccacaagccatcttggacatgatcgctggtgct
L V V A Q L L R I P Q A I L D M I A G A
cactggggagtcctggcgggcatagcgtatttctccatggtggggaactggacgaaggtc
H W G V L A G I A Y F S M V G N W T K V
ctggtagtgctgctgctatttgccggcgtcgacgcg
L V V L L L F A G V D A VGVRNSSGVYHVTNDCPNASVVYETDSLIIHLPGCVPCVREGNGSRCWVSLSPTVAAKDP
GVPVNEIRRHVDLIAGAAAFCSAMYVGHLCGSIFLVGQLFTLSPRRHWTTQDCNCSIYPG
HVTGHRMAWDMMMNWSPTTALVVAQLLRIPQAILDMIAGAHWGVLAGIAYFSMVGNWTKV
LVVLLLFAGVDA

AY651061 E2/NS1:

acgaccatcgtctccgggggaagtgccggccgcagcacggctggacttgttgggctcttc
T T I V S G G S A G R S T A G L V G L F
tcaccaggcgcccggcagaacatccagctgatcaacaccaacggcagttggcacatcaac
S P G A R Q N I Q L I N T N G S W H I N
cgcacggccctgaactgcaatgatacccttcaaaccggctgggtagcagggcttttctat
R T A L N C N D T L Q T G W V A G L F Y
accaacaaattcaactcttcgggttgccccgagaggttggccagctgccgaccccttgcc
T N K F N S S G C P E R L A S C R P L A
gactttgaccagggctggggccctatcagttataccaacggaagcggccccgaccaacgc
D F D Q G W G P I S Y T N G S G P D Q R
ccctactgctggcactacccccccaaaccttgtggtattgtgcccgcagagagcgtgtgt
P Y C W H Y P P K P C G I V P A E S V C
ggcccagtatactgcttcactcccagccccgtggtggtgggaacgaccgacaggtcgggc
G P V Y C F T P S P V V V G T T D R S G
gcgcccacctacaactggggtgaaaatgaaacggacgttttcgtcctcaacaacaccagg
A P T Y N W G E N E T D V F V L N N T R
ccacggctgggcaattggttcggtggtacctggatgaactcaactggattcaccaaggtg
P R L G N W F G G T W M N S T G F T K V
tgcggagcgcccccttgtgccatcggaggggtgggcaacaacaccttgtactgccccact
C G A P P C A I G G V G N N T L Y C P T
gattgtttccgcaaacatccggaagccacgtactctcggtgcggctccggtccttggatt
D C F R K H P E A T Y S R C G S G P W I
acacccaggtgcttgatccactacccgtataggctttggcattatccttgtaccatcaat
T P R C L I H Y P Y R L W H Y P C T I N
tacaccatattcaagatcaggatgtttgtgggcggggttgagcacaggctcgacgccgcg
Y T I F K I R M F V G G V E H R L D A A
tgcaactggacgcggggagagcgctgcgacttggacgacagggatcgggccgagttgagc
C N W T R G E R C D L D D R D R A E L S
cctctgttgctgtccactacgcaatggcaggtcctcccctgctcattcacaacactgccc
P L L L S T T Q W Q V L P C S F T T L P
gccctgtcaactggcctgatacatctccaccagaacatcgtggacgtgcagtacctctat
A L S T G L I H L H Q N I V D V Q Y L Y
gggttgagctcggcagtcacatcctgggtcataaagtgggagtacgttgtgctcctcttc
G L S S A V T S W V I K W E Y V V L L F
ttgctgctagcagatgctcgcatttgtgcctgcttgtggatgatgcttctcatatctcag
L L L A D A R I C A C L W M M L L I S Q
gtagaggcggcgctggagaacttgatagttctcaacgctgcttccctagtcgggacacat
V E A A L E N L I V L N A A S L V G T H Fig. 9 continued AY651061: NS5 ccgcgccgtc actgaaagca acatgcacca ctcaccatga ctctccagac gccgacctca
tagaagccaa cctcctgtgg agacgggaga tgggggggaa catcaccaga gtggagtcgg
agaacaagat tgttgttctg gattctttcg acccgctcgt ggcagaggag gatgaccggg
agatttctat tccagctgag attctgcgga aatttaagca gtttcccccc gccatgccca
tatgggcacg gccggattat aatcctcccc ttgtggaacc gtggaagcgc ccggactgtg
atccaccctt agtccacggg tgccccctac cacctcccaa gccgactccg gtgccgccac
cccggaaaaa gaggacggtg gtgctggacg agtctacagt atcatctgct ctggctgagc
ttgccactaa gaccttcggc agctctacaa cctcaggcgt gacaagtggt gaagcggccg
aatcgtcccc ggcgctttcc tgcgacggtg agctggactc cgaagctgaa tcttactcct
ccatgccccc tctcgagggg gaaccggggg accccgatct cagcgacggg tcttggtcta
ccgtgagcag tgatggcggt acggaggatg tcgtgtgctg ctcgatgtcc tactcgtgga
cgggcgcctt aattacgccc tgtgccgcag aggaaaccaa actccccatc aacgcactga
gtaactcgct gctgcgccac cacaatttgg tgtattccac cacctctcgc agcgctggca
agaggcagaa aaaagtcaca tttgacaggc tgcaggtcct ggacgatcat taccgggacg
tgctcaagga ggctaaggcc aaggcatcca cagtgaaggc taaattgcta tccgtagagg
aggcatgtag cctgacgccc ccgcactccg ccagatcaaa atttggctat gggccgaagg
atgtccgaag ccattccagt aaggctatac gccacatcaa ctccgtgtgg caggaccttc
tggaggacaa tacaacacct atagacacta ccatcatggc caagaatgaa gtcttctgcg
tgaaggccga aaaagggggt cgcaagcccg ctcgccttat cgtgtacccc gacctggggg
tgcgcgtgtg cgagaagaga gctttgtatg acgtagtcaa acagctcccc attgccgtga
tgggaccctc ctacgggttc cagtactcgc cagcgcagcg ggtcgacttc ctgcttaacg
cgtggaaatc aaagaaaaac cctatggggt ttcctatga cacccgttgc tttgactcaa
cagtcactga ggctgatatc cgtacggagg aagacctcta tcaatcttgt gacctggtcc
ctgaggcccg cgcggccata aggtctctca cagagaggct ttacatcggg ggcccactta
ccaattctaa gggacaaaac tgcggctatc ggcgatgccg cgcaagcggc gtgctgacca
ctagctgcgg taacaccata acttgctacc ttaaggctag tgcggcctgt cgagctgcaa
agctccagga ctgcaccatg ctcgtgtgcg gcgacgacct cgtcgttatc tgtgaaagcg
ccggtgtcaa ggaggacgct gcgagcctga gagccttcac cgaggctatg accaggtact
ccggcccccc gggagacccg gctcaaccag aatacgactt ggagcttata acatcctgct
cctccaatgt gtcggtcgcg cgcgacggcg ctggccaaag ggtctattat ctgacccgtg
aacctgagac tcccctcgcg cgtgccgctt gggagacagc aagacacact ccagtgaact
cctggctagg caacatcatc atgtttgccc ccactctgtg ggtacggatg gtcctcatga
cccacttatt ctccatactc atagttcagg agcaccttga aaaggctcta gattgtgaaa
tctatggagc cacacactcc gtcccaccgt tggacctacc tgaaatcatt caaagactcc
atggcctcag cgcgttttcg ctccacagtt actctccagg tgaaatcaat agggtggctt
catgcctcag gaaacttggg gttccacccct tgcgagcttg gagacaccgg gcccggagcg
tccgcgccac actcctatcc caggggggga aagccgccat atgcggtaag tacctcttca Fig. 9 continued AY651061: NS5 actgggcggt gaaaaccaaa ctcaaactca ttccattacc gctcgcgtct catttggact
tgtccaattg gttcacgggc ggctacagcg gggagacat ttatcacagc gtgtctcatg
cccggccccg ttggtttctc tggtgcctac tcctactctc agtaggggta ggcatctacc
tccttcccaa ccga

AY651061: 3` UTR:

tagacg gttgggcaac cactccaggc ctttaggccc tatttaaaca
ctccaggcct ttaggccccg t

AY651061 CORE:

```
atgagcacgaatcctaaacctcaaagaaaaaccaaacgtaacaccaaccgtcgcccacag
 M  S  T  N  P  K  P  Q  R  K  T  K  R  N  T  N  R  R  P  Q
gacgtcaagttcccgggtggcggacagatcgttggtggagtttacttgttgccgcgcagg
 D  V  K  F  P  G  G  G  Q  I  V  G  G  V  Y  L  L  P  R  R
ggccctagattgggtgtgcgcgcgacgaggaagacttccgagcggtcgcaacctcgaggt
 G  P  R  L  G  V  R  A  T  R  K  T  S  E  R  S  Q  P  R  G
agacgtcagcctatccccaaggcacgtcggcccgagggcaggacctgggctcagcccggg
 R  R  Q  P  I  P  K  A  R  R  P  E  G  R  T  W  A  Q  P  G
taccccttggcccctctatggcaatgagggctgcgggtgggcgggatggctcctgtctccc
 Y  P  W  P  L  Y  G  N  E  G  C  G  W  A  G  W  L  L  S  P
cgcggctctcggcctagttggggccccacagacccccggcgtagatcgcgcaatttgggt
 R  G  S  R  P  S  W  G  P  T  D  P  R  R  R  S  R  N  L  G
aaggtcatcgatacccttacgtatggcttcgccgacctcatggggtacataccgctcgtc
 K  V  I  D  T  L  T  Y  G  F  A  D  L  M  G  Y  I  P  L  V
ggcgccccccttgggggcgctgccagggccctggcgcacggcgtccgggtcctggaagac
 G  A  P  L  G  G  A  A  R  A  L  A  H  G  V  R  V  L  E  D
ggcgtgaactatgcaacagggaaccttcctggttgctctttctctatcttccttctggcc
 G  V  N  Y  A  T  G  N  L  P  G  C  S  F  S  I  F  L  L  A
ctgctctcttgcttgactgtgcccgcttcggcc
 L  L  S  C  L  T  V  P  A  S  A
```

AY651061 E1:

```
gtcggagtgcgcaactcttcgggggtgtaccatgtcaccaatgattgccccaatgcgtct
 V  G  V  R  N  S  S  G  V  Y  H  V  T  N  D  C  P  N  A  S
gttgtgtacgagacagatagcttgatcatacatctgccggggtgtgtgccctgcgtacgc
 V  V  Y  E  T  D  S  L  I  I  H  L  P  G  C  V  P  C  V  R
gagggcaacggttcgaggtgctgggtctcccttagtcctactgttgccgctaaggatccg
 E  G  N  G  S  R  C  W  V  S  L  S  P  T  V  A  A  K  D  P
ggcgtcccggtcaacgagattcggcgtcacgtcgacctgattgccggggccgctgcattc
 G  V  P  V  N  E  I  R  R  H  V  D  L  I  A  G  A  A  A  F
tgttcggctatgtatgtagggcacttatgcggttccatcttcctcgttggccagcttttc
 C  S  A  M  Y  V  G  H  L  C  G  S  I  F  L  V  G  Q  L  F
accctctcccctaggcgccactggacaacacaagactgtaattgctccatctacccagga
 T  L  S  P  R  R  H  W  T  T  Q  D  C  N  C  S  I  Y  P  G
catgtgacaggccatcgaatggcttgggacatgatgatgaactggtcccctacgacggcg
 H  V  T  G  H  R  M  A  W  D  M  M  M  N  W  S  P  T  T  A
```

Fig. 9 continued AY651061 E2/NS1

```
ggcatcgtccccttcttcatctttttttgtgcagcttggtacctaaaaggcaagtgggcc
 G  I  V  P  F  F  I  F  F  C  A  A  W  Y  L  K  G  K  W  A
cctggactcgcctattccgtctatgggatgtggccactgctcctgcttctcctggcgttg
 P  G  L  A  Y  S  V  Y  G  M  W  P  L  L  L  L  L  L  A  L
ccccaacgggcatacgcc
 P  Q  R  A  Y  A
```

TTIVSGGSAGRSTAGLVGLFSPGARQNIQLINTNGSWHINRTALNCNDTLQTGWVAGLFY
TNKFNSSGCPERLASCRPLADFDQGWGPISYTNGSGPDQRPYCWHYPPKPCGIVPAESVC
GPVYCFTPSPVVVGTTDRSGAPTYNWGENETDVFVLNNTRPRLGNWFGGTWMNSTGFTKV
CGAPPCAIGGVGNNTLYCPTDCFRKHPEATYSRCGSGPWITPRCLIHYPYRLWHYPCTIN
YTIFKIRMFVGGVEHRLDAACNWTRGERCDLDDRDRAELSPLLLSTTQWQVLPCSFTTLP
ALSTGLIHLHQNIVDVQYLYGLSSAVTSWVIKWEYVVLLFLLLADARICACLWMMLLISQ
VEAALENLIVLNAASLVGTHGIVPFFIFFCAAWYLKGKWAPGLAYSVYGMWPLLLLLLAL
PQRAYA

AY651061 NS2:

```
ttggatcaggagttggccgcgtcgtgtggggccacggtcttcatctgcctagcggtgctc
 L  D  Q  E  L  A  A  S  C  G  A  T  V  F  I  C  L  A  V  L
actctatcgccatattacaaacagtacatggcccgcggcatctggtggctgcagtacatg
 T  L  S  P  Y  Y  K  Q  Y  M  A  R  G  I  W  W  L  Q  Y  M
ctgaccagagcagaggcgctcctacaggtttgggtccccccgctcaacgcccgaggaggg
 L  T  R  A  E  A  L  L  Q  V  W  V  P  P  L  N  A  R  G  G
cgcgacggagtcgtactgctcacgtgtgtgctccacccgcacttgctctttgaaatcacc
 R  D  G  V  V  L  L  T  C  V  L  H  P  H  L  L  F  E  I  T
aagatcatgctggccattctcgggcctttgtggatcttgcaggccagtctgctcaaggta
 K  I  M  L  A  I  L  G  P  L  W  I  L  Q  A  S  L  L  K  V
ccgtacttcgtgcgcgttcagggccttctccggatctgcgcgctagcgcggaagatggtc
 P  Y  F  V  R  V  Q  G  L  L  R  I  C  A  L  A  R  K  M  V
ggaggccattacgtgcaaatggtcaccatcaagttaggggcgctcactggcacctatatt
 G  G  H  Y  V  Q  M  V  T  I  K  L  G  A  L  T  G  T  Y  I
tataaccatctcactcctcttcgggactgggcgcacaacggcttgcaagacctagccgta
 Y  N  H  L  T  P  L  R  D  W  A  H  N  G  L  Q  D  L  A  V
gctgtggagccagtcgtcttctcccaaatggagaccaagctcatcacgtggggggcagac
 A  V  E  P  V  V  F  S  Q  M  E  T  K  L  I  T  W  G  A  D
acagccgcgtgtggtgacatcatcaacggcttgcccgtctccgcccgcagg
 T  A  A  C  G  D  I  I  N  G  L  P  V  S  A  R  R
```

LDQELAASCGATVFICLAVLTLSPYYKQYMARGIWWLQYMLTRAEALLQVWVPPLNARGG
RDGVVLLTCVLHPHLLFEITKIMLAILGPLWILQASLLKVPYFVRVQGLLRICALARKMV
GGHYVQMVTIKLGALTGTYIYNHLTPLRDWAHNGLQDLAVAVEPVVFSQMETKLITWGAD
TAACGDIINGLPVSARR

```
ggccaggagatactgctcggaccagccgatggaatggcctctaggggatggaggttgctg
 G  Q  E  I  L  L  G  P  A  D  G  M  A  S  R  G  W  R  L  L
gcgcccatcacggcgtacgctcagcagacaaggggcctcctagggtgtataatcaccagc
 A  P  I  T  A  Y  A  Q  Q  T  R  G  L  L  G  C  I  I  T  S
ctgactggccgggacaagaaccaagtggagggtgaagtccagattgtgtcaactgctgcc
 L  T  G  R  D  K  N  Q  V  E  G  E  V  Q  I  V  S  T  A  A
caaacgttcttggcgacgtgcatcaacggggtatgctggactgtctaccacggggccgga
 Q  T  F  L  A  T  C  I  N  G  V  C  W  T  V  Y  H  G  A  G
accaggaccattgcatcatccaagggtcctgttattctaatgtataccaatgtagaccaa
 T  R  T  I  A  S  S  K  G  P  V  I  L  M  Y  T  N  V  D  Q
gacctcgggggctggaccgctcctcaagtgctcggctcactgacaccctggagctgcggc
 D  L  G  G  W  T  A  P  Q  V  L  G  S  L  T  P  W  S  C  G
tcctcggacctttacctggtcacgaggcatgccgatgtcattcccgtgccgcggcgaggt
 S  S  D  L  Y  L  V  T  R  H  A  D  V  I  P  V  P  R  R  G
gaaaccaggggcagcctgctttcgccccggcccatttcctatctaaagggatcctcggga
 E  T  R  G  S  L  L  S  P  R  P  I  S  Y  L  K  G  S  S  G
ggccccctgctctgtcccatgggacatgccgtgggcattttcagggccgcggtgtgcacc
 G  P  L  L  C  P  M  G  H  A  V  G  I  F  R  A  A  V  C  T
cgtggggtcgcaaaggcggtcgactttgtgcccgttgagtccttagagaccaccatgagg
 R  G  V  A  K  A  V  D  F  V  P  V  E  S  L  E  T  T  M  R
tccccagtgtttactgacaattccagccctctaacagtgccccagagttaccaggtggcg
 S  P  V  F  T  D  N  S  S  P  L  T  V  P  Q  S  Y  Q  V  A
catctacatgcacccactgggagtggcaagagcacgaaggtgccggccgcttacgcagct
 H  L  H  A  P  T  G  S  G  K  S  T  K  V  P  A  A  Y  A  A
caggggtacaaggtacttgtgctgaacccgtctgttgctgccaccttagggttcggtgct
 Q  G  Y  K  V  L  V  L  N  P  S  V  A  A  T  L  G  F  G  A
tatatgtcaaaggcccatgggatcgacccaaacatcaggaccggcgtgaggaccatcacc
 Y  M  S  K  A  H  G  I  D  P  N  I  R  T  G  V  R  T  I  T
acaggctcccccatcacctactccacctacggcaaatttttggctgatggcggatgccca
 T  G  S  P  I  T  Y  S  T  Y  G  K  F  L  A  D  G  G  C  P
ggaggtgcgtacgacatcataatatgtgacgaatgtcactcagtggacgccacctcgatt
 G  G  A  Y  D  I  I  I  C  D  E  C  H  S  V  D  A  T  S  I
ctgggcatagggaccgtcttggaccaagcggagacggcgggggtcaggctcactgtcctc
 L  G  I  G  T  V  L  D  Q  A  E  T  A  G  V  R  L  T  V  L
gccaccgctacaccacctggttccgtcaccgtgccacattccaacatcgaggaagttgca
 A  T  A  T  P  P  G  S  V  T  V  P  H  S  N  I  E  E  V  A
ctgtccgctgacggggaaataccattttatggtaaggccatccccctaaactacatcaag
 L  S  A  D  G  E  I  P  F  Y  G  K  A  I  P  L  N  Y  I  K
gggggaaggcacctcattttctgccactccaagaagaagtgcgacgagctcgctgcaaag
 G  G  R  H  L  I  F  C  H  S  K  K  K  C  D  E  L  A  A  K
ctggtcggtccgggcgtcaacgcggtggccttttaccgtggcctcgacgtatctgtcatt
 L  V  G  P  G  V  N  A  V  A  F  Y  R  G  L  D  V  S  V  I
ccaactacaggagacgtcgttgttgtagcgaccgacgccttgatgactggcttcaccgga
 P  T  T  G  D  V  V  V  V  A  T  D  A  L  M  T  G  F  T  G
gatttcgactctgtgatagactgcaacacctgtgtcgtccagacagtcgacttcagccta
 D  F  D  S  V  I  D  C  N  T  C  V  V  Q  T  V  D  F  S  L
gaccctatattctctattgagacttccaccgtgccccaggacgccgtgtcccgctcccaa
 D  P  I  F  S  I  E  T  S  T  V  P  Q  D  A  V  S  R  S  Q
cggaggggtaggaccggtcgagggaagcatggtatttacagatatgtgtcacccggggag
 R  R  G  R  T  G  R  G  K  H  G  I  Y  R  Y  V  S  P  G  E
cggccgtctggcatgttcgactccgtggtcctctgtgagtgctatgacgcgggttgtgct
 R  P  S  G  M  F  D  S  V  V  L  C  E  C  Y  D  A  G  C  A
tggtacgagcttacacccgccgagaccacagtcaggctacgggcatacctcaacacccca
 W  Y  E  L  T  P  A  E  T  T  V  R  L  R  A  Y  L  N  T  P
ggattgcccgtgtgccaggaccacttggagttctgggagagtgtcttcaccggcctcacc
 G  L  P  V  C  Q  D  H  L  E  F  W  E  S  V  F  T  G  L  T
```

Fig. 9 continued AY651061 NS3 cacatagatgcccacttcctgtcccagacgaaacagagtggggagaacttcccctaccta
H I D A H F L S Q T K Q S G E N F P Y L
gtcgcataccaagccaccgtgtgcgctagagctagagctcctcccccgtcatgggaccaa
V A Y Q A T V C A R A R A P P P S W D Q
atgtggaagtgcctgatacggctcaagcccaccctcactggggctaccccattactatac
M W K C L I R L K P T L T G A T P L L Y
agactgggtagtgtacagaatgagatcaccttaacacacccaatcacccaatacatcatg
R L G S V Q N E I T L T H P I T Q Y I M
gcttgcatgtcggcggacctggaggtcgtcact
A C M S A D L E V V T GQEILLGPADGMASRGWRLLAPITAYAQQTRGLLGCIITSLTGRDKNQVEGEVQIVSTAA
QTFLATCINGVCWTVYHGAGTRTIASSKGPVILMYTNVDQDLGGWTAPQVLGSLTPWSCG
SSDLYLVTRHADVIPVPRRGETRGSLLSPRPISYLKGSSGGPLLCPMGHAVGIFRAAVCT
RGVAKAVDFVPVESLETTMRSPVFTDNSSPLTVPQSYQVAHLHAPTGSGKSTKVPAAYAA
QGYKVLVLNPSVAATLGFGAYMSKAHGIDPNIRTGVRTITTGSPITYSTYGKFLADGGCP
GGAYDIIICDECHSVDATSILGIGTVLDQAETAGVRLTVLATATPPGSVTVPHSNIEEVA
LSADGEIPFYGKAIPLNYIKGGRHLIFCHSKKKCDELAAKLVGPGVNAVAFYRGLDVSVI
PTTGDVVVVATDALMTGFTGDFDSVIDCNTCVVQTVDFSLDPIFSIETSTVPQDAVSRSQ
RRGRTGRGKHGIYRYVSPGERPSGMFDSVVLCECYDAGCAWYELTPAETTVRLRAYLNTP
GLPVCQDHLEFWESVFTGLTHIDAHFLSQTKQSGENFPYLVAYQATVCARARAPPPSWDQ
MWKCLIRLKPTLTGATPLLYRLGSVQNEITLTHPITQYIMACMSADLEVVT

AY651061 NS4:

agcacgtgggtgttggtgggcggcgtcctagccgctttggccgcttactgcctgtccaca
S T W V L V G G V L A A L A A Y C L S T
ggcagcgtggtcatagtgggcaggataatcctaggtgggaagccggcagtcatacctgac
G S V V I V G R I I L G G K P A V I P D
agggaggttctctaccgagagtttgatgagatggaggagtgcgccgcccacgtcccctac
R E V L Y R E F D E M E E C A A H V P Y
ctcgagcaggggatgcatttggcggagcagttcaagcagaaagctcttgggttgctccag
L E Q G M H L A E Q F K Q K A L G L L Q
acggcatccaaacaaacagagacgatcactcccattgtccagtctaattggcagaagctc
T A S K Q T E T I T P I V Q S N W Q K L
gagtctttctgggctaaacacatgtggaacttcgttagcgggatacaatatctggcgggc
E S F W A K H M W N F V S G I Q Y L A G
ctatcaacgctgcccgggaaccccgctatagcatcgctgatgtcgtttacggccgcagtg
L S T L P G N P A I A S L M S F T A A V
acgagtccactaaccactcagcagaccctcctctttaacatcttgggggggtggctggct
T S P L T T Q Q T L L F N I L G G W L A
gcccagcttgccgccccagccgccgccacagccttcgttggcgcaggcattactggcgcc
A Q L A A P A A A T A F V G A G I T G A
gttgttggcagtgtgggcctagggaaggtcctggtggacattcttgccggctacggggct
V V G S V G L G K V L V D I L A G Y G A
ggtgtggccggggccctcgtggctttcaaaatcatgagcggggagacccccaccacggag
G V A G A L V A F K I M S G E T P T T E
gatctagtcaaccttctgcctgccatcctatcgccaggagctctcgttgtcgccgtggtg Fig. 9 continued AY651061 NS4

```
 D  L  V  N  L  L  P  A  I  L  S  P  G  A  L  V  V  A  V  V
tgcgcagcaatactacgccggcacgtgggccttggcgagggcgccgtgcagtggatgaac
 C  A  A  I  L  R  R  H  V  G  L  G  E  G  A  V  Q  W  M  N
cggctgatagcgtttgcttctcggggtaaccacgtctcccctacacactacgtgccggag
 R  L  I  A  F  A  S  R  G  N  H  V  S  P  T  H  Y  V  P  E
agcgacgcgtcggctcgtgtcacaccaattctcaccaggctcactgttactcagcttctg
 S  D  A  S  A  R  V  T  P  I  L  T  R  L  T  V  T  Q  L  L
aaagggctccacgtgtggataagctcgaattgcatcgccccgtgt
 K  G  L  H  V  W  I  S  S  N  C  I  A  P  C
```

STWVLVGGVLAALAAYCLSTGSVVIVGRIILGGKPAVIPDREVLYREFDEMEECAAHVPY
LEQGMHLAEQFKQKALGLLQTASKQTETITPIVQSNWQKLESFWAKHMWNFVSGIQYLAG
LSTLPGNPAIASLMSFTAAVTSPLTTQQTLLFNILGGWLAAQLAAPAAATAFVGAGITGA
VVGSVGLGKVLVDILAGYGAGVAGALVAFKIMSGETPTTEDLVNLLPAILSPGALVVAVV
CAAILRRHVGLGEGAVQWMNRLIAFASRGNHVSPTHYVPESDASARVTPILTRLTVTQLL
KGLHVWISSNCIAPC

AY651061 NS5 :

```
gctagttcttggcttaaagatgtctggaactggatatgcgaggtgctgagcgacttcaag
 A  S  S  W  L  K  D  V  W  N  W  I  C  E  V  L  S  D  F  K
aattggctgaaggccaaacttgtaccacaactgcccgggatcccattcgtatcctgccaa
 N  W  L  K  A  K  L  V  P  Q  L  P  G  I  P  F  V  S  C  Q
cgcgggtaccgtggggtctggcggggcgagggcatcgtgcacactcgttgcccgtgtggg
 R  G  Y  R  G  V  W  R  G  E  G  I  V  H  T  R  C  P  C  G
gccaatataactggacatgtcaagaacggttcgatgagaatcgtcgggcctaagacttgc
 A  N  I  T  G  H  V  K  N  G  S  M  R  I  V  G  P  K  T  C
agcaacacctggcgtgggtcgttccccattaacgcttacactacaggcccgtgcacgccc
 S  N  T  W  R  G  S  F  P  I  N  A  Y  T  T  G  P  C  T  P
tccccggcgccgaactatacgttcgcgctatggagggtgtctgcagaggagtatgtggag
 S  P  A  P  N  Y  T  F  A  L  W  R  V  S  A  E  E  Y  V  E
gtaaggcggctgggggacttccattacgtcacgggggtgaccactgataaactcaagtgt
 V  R  R  L  G  D  F  H  Y  V  T  G  V  T  T  D  K  L  K  C
ccatgccaggtcccctcacccgagttctccacagaggtggacggggtgcgcctgcatagg
 P  C  Q  V  P  S  P  E  F  S  T  E  V  D  G  V  R  L  H  R
tacgcccctccctgcaaacccctgctacgggatgaggtgacgtttagcgtcgggttcaat
 Y  A  P  P  C  K  P  L  L  R  D  E  V  T  F  S  V  G  F  N
gaatacctggtggggtcccagttgccctgcgagcccgagccagacgtagcagcattaaca
 E  Y  L  V  G  S  Q  L  P  C  E  P  E  P  D  V  A  A  L  T
tcaatgcttacagacccttcccacatcactgcaaagacggcggcgcgtaggctgaagcgg
 S  M  L  T  D  P  S  H  I  T  A  K  T  A  A  R  R  L  K  R
gggtctccccccctccctggccagttcttctgccagccagctgtccgcgccgtcactgaaa
 G  S  P  P  S  L  A  S  S  S  A  S  Q  L  S  A  P  S  L  K
gcaacatgcaccactcaccatgactctccagacgccgacctcatagaagccaacctcctg
 A  T  C  T  T  H  H  D  S  P  D  A  D  L  I  E  A  N  L  L
tggagacgggagatgggggggaacatcaccagagtggagtcggagaacaagattgttgtt
 W  R  R  E  M  G  G  N  I  T  R  V  E  S  E  N  K  I  V  V
ctggattctttcgacccgctcgtggcagaggaggatgaccgggagatttctattccagct
 L  D  S  F  D  P  L  V  A  E  E  D  D  R  E  I  S  I  P  A
gagattctgcggaaatttaagcagtttcccccgccatgcccatatgggcacggccggat
 E  I  L  R  K  F  K  Q  F  P  P  A  M  P  I  W  A  R  P  D
```

Fig. 9 continued AY651061 NS5 tataatcctccccttgtggaaccgtggaagcgcccggactgtgatccaccccttagtccac

Y N P P L V E P W K R P D C D P P L V H gggtgcccccctaccacctcccaagccgactccggtgccgccaccccggaaaagaggacg

G C P L P P P K P T P V P P P R K K R T gtggtgctggacgagtctacagtatcatctgctctggctgagcttgccactaagaccttc

V V L D E S T V S S A L A E L A T K T F ggcagctctacaacctcaggcgtgacaagtggtgaagcggccgaatcgtccccggcgctt

G S S T T S G V T S G E A A E S S P A L tcctgcgacggtgagctggactccgaagctgaatcttactcctccatgccccctctcgag

S C D G E L D S E A E S Y S S M P P L E ggggaaccgggggaccccgatctcagcgacgggtcttggtctaccgtgagcagtgatggc

G E P G D P D L S D G S W S T V S S D G ggtacggaggatgtcgtgtgctgctcgatgtcctactcgtggacgggcgccttaattacg

G T E D V V C C S M S Y S W T G A L I T ccctgtgccgcagaggaaaccaaactccccatcaacgcactgagtaactcgctgctgcgc

P C A A E E T K L P I N A L S N S L L R caccacaatttggtgtattccaccacctctcgcagcgctggcaagaggcagaaaaagtc

H H N L V Y S T T S R S A G K R Q K K V acatttgacaggctgcaggtcctggacgatcattaccgggacgtgctcaaggaggctaag

T F D R L Q V L D D H Y R D V L K E A K gccaaggcatccacagtgaaggctaaattgctatccgtagaggaggcatgtagcctgacg

A K A S T V K A K L L S V E E A C S L T cccccgcactccgccagatcaaaatttggctatgggccgaaggatgtccgaagccattcc

P P H S A R S K F G Y G P K D V R S H S agtaaggctatacgccacatcaactccgtgtggcaggaccttctggaggacaatacaaca

S K A I R H I N S V W Q D L L E D N T T cctatagacactaccatcatggccaagaatgaagtcttctgcgtgaaggccgaaaaaggg

P I D T T I M A K N E V F C V K A E K G ggtcgcaagcccgctcgccttatcgtgtaccccgacctgggggtgcgcgtgtgcgagaag

G R K P A R L I V Y P D L G V R V C E K agagctttgtatgacgtagtcaaacagctccccattgccgtgatgggaccctcctacggg

R A L Y D V V K Q L P I A V M G P S Y G ttccagtactcgccagcgcagcgggtcgacttcctgcttaacgcgtggaaatcaaagaaa

F Q Y S P A Q R V D F L L N A W K S K K aaccctatggggtttttcctatgacacccgttgctttgactcaacagtcactgaggctgat

N P M G F S Y D T R C F D S T V T E A D atccgtacggaggaagacctctatcaatcttgtgacctggtccctgaggcccgcgcggcc

I R T E E D L Y Q S C D L V P E A R A A ataaggtctctcacagagaggctttacatcgggggcccacttaccaattctaagggacaa

I R S L T E R L Y I G G P L T N S K G Q aactgcggctatcggcgatgccgcgcaagcggcgtgctgaccactagctgcggtaacacc

N C G Y R R C R A S G V L T T S C G N T ataacttgctaccttaaggctagtgcggcctgtcgagctgcaaagctccaggactgcacc

I T C Y L K A S A A C R A A K L Q D C T atgctcgtgtgcggcgacgacctcgtcgttatctgtgaaagcgccggtgtcaaggaggac

M L V C G D D L V V I C E S A G V K E D gctgcgagcctgagagccttcaccgaggctatgaccaggtactccggcccccgggagac

A A S L R A F T E A M T R Y S G P P G D ccggctcaaccagaatacgacttggagcttataacatcctgctcctccaatgtgtcggtc

P A Q P E Y D L E L I T S C S S N V S V gcgcgcgacggcgctggccaaagggtctattatctgacccgtgaacctgagactcccctc

A R D G A G Q R V Y Y L T R E P E T P L gcgcgtgccgcttgggagacagcaagacacactccagtgaactcctggctaggcaacatc

A R A A W E T A R H T P V N S W L G N I atcatgtttgcccccactctgtgggtacggatggtcctcatgacccacttattctccata

I M F A P T L W V R M V L M T H L F S I ctcatagttcaggagcaccttgaaaaggctctagattgtgaaatctatggagccacacac Fig. 9 continued AY651061 NS5

```
 L  I  V  Q  E  H  L  E  K  A  L  D  C  E  I  Y  G  A  T  H
tccgtcccaccgttggacctacctgaaatcattcaaagactccatggcctcagcgcgttt
 S  V  P  P  L  D  L  P  E  I  I  Q  R  L  H  G  L  S  A  F
tcgctccacagttactctccaggtgaaatcaatagggtggcttcatgcctcaggaaactt
 S  L  H  S  Y  S  P  G  E  I  N  R  V  A  S  C  L  R  K  L
ggggttccacccttgcgagcttggagacaccgggcccggagcgtccgcgccacactccta
 G  V  P  P  L  R  A  W  R  H  R  A  R  S  V  R  A  T  L  L
tcccagggggggaaagccgccatatgcggtaagtacctcttcaactgggcggtgaaaacc
 S  Q  G  G  K  A  A  I  C  G  K  Y  L  F  N  W  A  V  K  T
aaactcaaactcattccattaccgctcgcgtctcatttggacttgtccaattggttcacg
 K  L  K  L  I  P  L  P  L  A  S  H  L  D  L  S  N  W  F  T
ggcggctacagcgggggagacatttatcacagcgtgtctcatgcccggccccgttggttt
 G  G  Y  S  G  G  D  I  Y  H  S  V  S  H  A  R  P  R  W  F
ctctggtgcctactcctactctcagtaggggtaggcatctacctccttcccaaccga
 L  W  C  L  L  L  L  S  V  G  V  G  I  Y  L  L  P  N  R
```

ASSWLKDVWNWICEVLSDFKNWLKAKLVPQLPGIPFVSCQRGYRGVWRGEGIVHTRCPCG
ANITGHVKNGSMRIVGPKTCSNTWRGSFPINAYTTGPCTPSPAPNYTFALWRVSAEEYVE
VRRLGDFHYVTGVTTDKLKCPCQVPSPEFSTEVDGVRLHRYAPPCKPLLRDEVTFSVGFN
EYLVGSQLPCEPEPDVAALTSMLTDPSHITAKTAARRLKRGSPPSLASSSASQLSAPSLK
ATCTTHHDSPDADLIEANLLWRREMGGNITRVESENKIVVLDSFDPLVAEEDDREISIPA
EILRKFKQFPPAMPIWARPDYNPPLVEPWKRPDCDPPLVHGCPLPPPKPTPVPPPRKKRT
VVLDESTVSSALAELATKTFGSSTTSGVTSGEAAESSPALSCDGELDSEAESYSSMPPLE
GEPGDPDLSDGSWSTVSSDGGTEDVVCCSMSYSWTGALITPCAAEETKLPINALSNSLLR
HHNLVYSTTSRSAGKRQKKVTFDRLQVLDDHYRDVLKEAKAKASTVKAKLLSVEEACSLT
PPHSARSKFGYGPKDVRSHSSKAIRHINSVWQDLLEDNTTPIDTTIMAKNEVFCVKAEKG
GRKPARLIVYPDLGVRVCEKRALYDVVKQLPIAVMGPSYGFQYSPAQRVDFLLNAWKSKK
NPMGFSYDTRCFDSTVTEADIRTEEDLYQSCDLVPEARAAIRSLTERLYIGGPLTNSKGQ
NCGYRRCRASGVLTTSCGNTITCYLKASAACRAAKLQDCTMLVCGDDLVVICESAGVKED
AASLRAFTEAMTRYSGPPGDPAQPEYDLELITSCSSNVSVARDGAGQRVYYLTREPETPL
ARAAWETARHTPVNSWLGNIIMFAPTLWVRMVLMTHLFSILIVQEHLEKALDCEIYGATH
SVPPLDLPEIIQRLHGLSAFSLHSYSPGEINRVASCLRKLGVPPLRAWRHRARSVRATLL
SQGGKAAICGKYLFNWAVKTKLKLIPLPLASHLDLSNWFTGGYSGGDIYHSVSHARPRWF
LWCLLLLSVGVGIYLLPNR

Fig. 10

SEQ ID No.2 translation="MSTNPKPQRKTKRNTNRRPQDVKFPGGGQIVGGVYLLPRRGPRL
GVRATRKTSERSQPRGRRQPIPKARRPEGRTWAQPGYPWPLYGNEGCGWAGWLLSPRG
SRPSWGPTDPRRRSRNLGKVIDTLTYGFADLMGYIPLVGAPLGGAARALAHGVRVLED Fig. 10 continued SEQ ID No.2

GVNYATGNLPGCSFSIFLLALLSCLTVPASAVGVRNSSGVYHVTNDCPNASVVYETDS

LIIHLPGCVPCVREGNGSRCWVSLSPTVAAKDPGVPVNEIRRHVDLIAGAAAFCSAMY

VGHLCGSIFLVGQLFTLSPRRHWTTQDCNCSIYPGHVTGHRMAWDMMMNWSPTTALV
V

AQLLRIPQAILDMIAGAHWGVLAGIAYFSMVGNWTKVLVVLLLFAGVDATTIVSGGSA

GRSTAGLVGLFSPGARQNIQLINTNGSWHINRTALNCNDTLQTGWVAGLFYTNKFNSS

GCPERLASCRPLADFDQGWGPISYTNGSGPDQRPYCWHYPPKPCGIVPAESVCGPVYC

FTPSPVVVGTTDRSGAPTYNWGENETDVFVLNNTRPRLGNWFGGTWMNSTGFTKVCGA

PPCAIGGVGNNTLYCPTDCFRKHPEATYSRCGSGPWITPRCLIHYPYRLWHYPCTINY

TIFKIRMFVGGVEHRLDAACNWTRGERCDLDDRDRAELSPLLLSTTQWQVLPCSFTTL

PALSTGLIHLHQNIVDVQYLYGLSSAVTSWVIKWEYVVLLFLLLADARICACLWMMLL

ISQVEAALENLIVLNAASLVGTHGIVPFFIFFCAAWYLKGKWAPGLAYSVYGMWPLLL

LLLALPQRAYALDQELAASCGATVFICLAVLTLSPYYKQYMARGIWWLQYMLTRAEAL

LQVWVPPLNARGGRDGVVLLTCVLHPHLLFEITKIMLAILGPLWILQASLLKVPYFVR

VQGLLRICALARKMVGGHYVQMVTIKLGALTGTYIYNHLTPLRDWAHNGLQDLAVAV
E

PVVFSQMETKLITWGADTAACGDIINGLPVSARRGQEILLGPADGMASRGWRLLAPIT

AYAQQTRGLLGCIITSLTGRDKNQVEGEVQIVSTAAQTFLATCINGVCWTVYHGAGTR

TIASSKGPVILMYTNVDQDLGGWTAPQVLGSLTPWSCGSSDLYLVTRHADVIPVPRRG

ETRGSLLSPRPISYLKGSSGGPLLCPMGHAVGIFRAAVCTRGVAKAVDFVPVESLETT

MRSPVFTDNSSPLTVPQSYQVAHLHAPTGSGKSTKVPAAYAAQGYKVLVLNPSVAATL

GFGAYMSKAHGIDPNIRTGVRTITTGSPITYSTYGKFLADGGCPGGAYDIIICDECHS

VDATSILGIGTVLDQAETAGVRLTVLATATPPGSVTVPHSNIEEVALSADGEIPFYGK

AIPLNYIKGGRHLIFCHSKKKCDELAAKLVGPGVNAVAFYRGLDVSVIPTTGDVVVVA

TDALMTGFTGDFDSVIDCNTCVVQTVDFSLDPIFSIETSTVPQDAVSRSQRRGRTGRG

KHGIYRYVSPGERPSGMFDSVVLCECYDAGCAWYELTPAETTVRLRAYLNTPGLPVCQ

Fig. 10 continued SEQ ID No.2

DHLEFWESVFTGLTHIDAHFLSQTKQSGENFPYLVAYQATVCARARAPPPSWDQMWKC
LIRLKPTLTGATPLLYRLGSVQNEITLTHPITQYIMACMSADLEVVTSTWVLVGGVLA
ALAAYCLSTGSVVIVGRIILGGKPAVIPDREVLYREFDEMEECAAHVPYLEQGMHLAE
QFKQKALGLLQTASKQTETITPIVQSNWQKLESFWAKHMWNFVSGIQYLAGLSTLPGN
PAIASLMSFTAAVTSPLTTQQTLLFNILGGWLAAQLAAPAAATAFVGAGITGAVVGSV
GLGKVLVDILAGYGAGVAGALVAFKIMSGETPTTEDLVNLLPAILSPGALVVAVVCAA
ILRRHVGLGEGAVQWMNRLIAFASRGNHVSPTHYVPESDASARVTPILTRLTVTQLLK
GLHVWISSNCIAPCASSWLKDVWNWICEVLSDFKNWLKAKLVPQLPGIPFVSCQRGYR
GVWRGEGIVHTRCPCGANITGHVKNGSMRIVGPKTCSNTWRGSFPINAYTTGPCTPSP
APNYTFALWRVSAEEYVEVRRLGDFHYVTGVTTDKLKCPCQVPSPEFSTEVDGVRLHR
YAPPCKPLLRDEVTFSVGFNEYLVGSQLPCEPEPDVAALTSMLTDPSHITAKTAARRL
KRGSPPSLASSSASQLSAPSLKATCTTHHDSPDADLIEANLLWRREMGGNITRVESEN
KIVVLDSFDPLVAEEDDREISIPAEILRKFKQFPPAMPIWARPDYNPPLVEPWKRPDC
DPPLVHGCPLPPPKPTPVPPPRKKRTVVLDESTVSSALAELATKTFGSSTTSGVTSGE
AAESSPALSCDGELDSEAESYSSMPPLEGEPGDPDLSDGSWSTVSSDGGTEDVVCCSM
SYSWTGALITPCAAEETKLPINALSNSLLRHHNLVYSTTSRSAGKRQKKVTFDRLQVL
DDHYRDVLKEAKAKASTVKAKLLSVEEACSLTPPHSARSKFGYGPKDVRSHSSKAIRH
INSVWQDLLEDNTTPIDTTIMAKNEVFCVKAEKGGRKPARLIVYPDLGVRVCEKRALY
DVVKQLPIAVMGPSYGFQYSPAQRVDFLLNAWKSKKNPMGFSYDTRCFDSTVTEADIR
TEEDLYQSCDLVPEARAAIRSLTERLYIGGPLTNSKGQNCGYRRCRASGVLTTSCGNT
ITCYLKASAACRAAKLQDCTMLVCGDDLVVICESAGVKEDAASLRAFTEAMTRYSGPP
GDPAQPEYDLELITSCSSNVSVARDGAGQRVYYLTREPETPLARAAWETARHTPVNSW
LGNIIMFAPTLWVRMVLMTHLFSILIVQEHLEKALDCEIYGATHSVPPLDLPEIIQRL
HGLSAFSLHSYSPGEINRVASCLRKLGVPPLRAWRHRARSVRATLLSQGGKAAICGKY
LFNWAVKTKLKLIPLPLASHLDLSNWFTGGYSGGDIYHSVSHARPRWFLWCLLLLSVG

Fig. 10 continued SEQ ID No.2

VGIYLLPNR"

SEQ ID No. 1

ORIGIN 1 gccagccccc tgatgggggc gacactccgc catgaatcac tcccctgtga ggaactactg
61 tcttcacgca gaaagcgtct agccatggcg ttagtatgag tgtcgtgcag cctccaggac
121 ccccccctccc gggagagcca tagtggtctg cggaaccggt gagtacaccg gaattgccag
181 gacgaccggg tcctttcttg gataaacccg ctcaacgcct ggagatttgg gcgtgccccc
241 gcaagactgc tagccgagta gtgttgggtc gcgaaaggcc ttgtggtact gcctgatagg
301 gtgcttgcga gtgccccggg aggtctcgta gaccgtgcac catgagcacg aatcctaaac
361 ctcaaagaaa aaccaaacgt aacaccaacc gtcgcccaca ggacgtcaag ttcccgggtg
421 gcggacagat cgttggtgga gtttacttgt tgccgcgcag gggccctaga ttgggtgtgc
481 gcgcgacgag gaagacttcc gagcggtcgc aacctcgagg tagacgtcag cctatcccca
541 aggcacgtcg gcccgagggc aggacctggg ctcagcccgg gtacccttgg cccctctatg
601 gcaatgaggg ctgcgggtgg gcgggatggc tcctgtctcc ccgcggctct cggcctagtt
661 ggggccccac agacccccgg cgtagatcgc gcaatttggg taaggtcatc gataccctta
721 cgtatggctt cgccgacctc atggggtaca taccgctcgt cggcgccccc cttgggggcg
781 ctgccagggc cctggcgcac ggcgtccggg tcctggaaga cggcgtgaac tatgcaacag
841 ggaaccttcc tggttgctct ttctctatct tccttctggc cctgctctct tgcttgactg
901 tgcccgcttc ggccgtcgga gtgcgcaact cttcgggggt gtaccatgtc accaatgatt
961 gccccaatgc gtctgttgtg tacgagacag atagcttgat catacatctg ccgggggtgtg
1021 tgccctgcgt acgcgagggc aacggttcga ggtgctgggt ctcccttagt cctactgttg
1081 ccgctaagga tccgggcgtc ccggtcaacg agattcggcg tcacgtcgac ctgattgccg
1141 gggccgctgc attctgttcg gctatgtatg tagggcactt atgcggttcc atcttcctcg
1201 ttggccagct tttcaccctc tcccctaggc gccactggac aacacaagac tgtaattgct
1261 ccatctaccc aggacatgtg acaggccatc gaatggcttg ggacatgatg atgaactggt
1321 cccctacgac ggcgctggta gtagcccagc tgctccggat cccacaagcc atcttggaca
1381 tgatcgctgg tgctcactgg ggagtcctgg cgggcatagc gtatttctcc atggtgggga
1441 actggacgaa ggtcctggta gtgctgctgc tatttgccgg cgtcgacgcg acgaccatcg
1501 tctccggggg aagtgccggc cgcagcacgg ctggacttgt tgggctcttc tcaccaggcg
1561 cccggcagaa catccagctg atcaacacca acggcagttg gcacatcaac cgcacggccc
1621 tgaactgcaa tgataccctt caaaccggct gggtagcagg gcttttctat accaacaaat
1681 tcaactcttc gggttgcccc gagaggttgg ccagctgccg acccttgcc gactttgacc
1741 agggctgggg ccctatcagt tataccaacg gaagcggccc cgaccaacgc ccctactgct
1801 ggcactaccc cccaaaacct tgtggtattg tgcccgcaga gagcgtgtgt ggcccagtat
1861 actgcttcac tcccagcccc gtggtggtgg gaacgaccga caggtcgggc gcgcccacct
1921 acaactgggg tgaaaatgaa acggacgttt tcgtcctcaa caacaccagg ccacggctgg
1981 gcaattggtt cggtggtacc tggatgaact caactggatt caccaaggtg tgcggagcgc
2041 ccccttgtgc catcggaggg gtgggcaaca acaccttgta ctgccccact gattgtttcc
2101 gcaaacatcc ggaagccacg tactctcggt gcggctccgg tccttggatt acacccaggt
2161 gcttgatcca ctacccgtat aggctttggc attatccttg taccatcaat tacaccatat
2221 tcaagatcag gatgtttgtg ggcgggggttg agcacaggct cgacgccgcg tgcaactgga
2281 cgcgggggaga gcgctgcgac ttggacgaca gggatcgggc cgagttgagc cctctgttgc
2341 tgtccactac gcaatggcag gtcctcccct gctcattcac aacactgccc gccctgtcaa
2401 ctggcctgat acatctccac cagaacatcg tggacgtgca gtacctctat gggttgagct
2461 cggcagtcac atcctgggtc ataaagtggg agtacgttgt gctcctcttc ttgctgctag
2521 cagatgctcg catttgtgcc tgcttgtgga tgatgcttct catatctcag gtagaggcgg Fig. 10 continued SEQ ID No.1

2581 cgctggagaa cttgatagtt ctcaacgctg cttccctagt cgggacacat ggcatcgtcc
2641 ccttcttcat cttttttgt gcagcttggt acctaaaagg caagtgggcc cctggactcg
2701 cctattccgt ctatgggatg tggccactgc tcctgcttct cctggcgttg ccccaacggg
2761 catacgcctt ggatcaggag ttggccgcgt cgtgtggggc cacggtcttc atctgcctag
2821 cggtgctcac tctatcgcca tattacaaac agtacatggc ccgcggcatc tggtggctgc
2881 agtacatgct gaccagagca gaggcgctcc tacaggtttg ggtcccccg ctcaacgccc
2941 gaggagggcg cgacggagtc gtactgctca cgtgtgtgct ccacccgcac ttgctctttg
3001 aaatcaccaa gatcatgctg gccattctcg ggcctttgtg gatcttgcag gccagtctgc
3061 tcaaggtacc gtacttcgtg cgcgttcagg gccttctccg gatctgcgcg ctagcgcgga
3121 agatggtcgg aggccattac gtgcaaatgg tcaccatcaa gttaggggcg ctcactggca
3181 cctatattta taaccatctc actcctcttc gggactgggc gcacaacggc ttgcaagacc
3241 tagccgtagc tgtggagcca gtcgtcttct cccaaatgga gaccaagctc atcacgtggg
3301 gggcagacac agccgcgtgt ggtgacatca tcaacggctt gcccgtctcc gcccgcaggg
3361 gccaggagat actgctcgga ccagccgatg gaatggcctc taggggatgg aggttgctgg
3421 cgcccatcac ggcgtacgct cagcagacaa ggggcctcct agggtgtata atcaccagcc
3481 tgactggccg ggacaagaac caagtggagg gtgaagtcca gattgtgtca actgctgccc
3541 aaacgttctt ggcgacgtgc atcaacgggg tatgctggac tgtctaccac ggggccggaa
3601 ccaggaccat tgcatcatcc aagggtcctg ttattctaat gtataccaat gtagaccaag
3661 acctcggggg ctggaccgct cctcaagtgc tcggctcact gacaccctgg agctgcggct
3721 cctcggacct ttacctggtc acgaggcatg ccgatgtcat tcccgtgccg cggcgaggtg
3781 aaaccagggg cagcctgctt tcgccccggc ccatttccta tctaaaggga tcctcgggag
3841 gcccccctgct ctgtcccatg ggacatgccg tgggcatttt cagggccgcg gtgtgcaccc
3901 gtggggtcgc aaaggcggtc gactttgtgc ccgttgagtc cttagagacc accatgaggt
3961 ccccagtgtt tactgacaat tccagccctc taacagtgcc ccagagttac caggtggcgc
4021 atctacatgc acccactggg agtggcaaga gcacgaaggt gccggccgct tacgcagctc
4081 aggggtacaa ggtacttgtg ctgaacccgt ctgttgctgc caccttaggg ttcggtgctt
4141 atatgtcaaa ggcccatggg atcgacccaa acatcaggac cggcgtgagg accatcacca
4201 caggctcccc catcacctac tccacctacg gcaaattttt ggctgatggc ggatgcccag
4261 gaggtgcgta cgacatcata atatgtgacg aatgtcactc agtggacgcc acctcgattc
4321 tgggcatagg gaccgtcttg gaccaagcgg agacggcggg ggtcaggctc actgtcctcg
4381 ccaccgctac accacctggt tccgtcaccg tgccacattc caacatcgag gaagttgcac
4441 tgtccgctga cggggaaata ccattttatg gtaaggccat cccctaaac tacatcaagg
4501 gggggaggca cctcattttc tgccactcca agaagaagtg cgacgagctc gctgcaaagc
4561 tggtcggtcc gggcgtcaac gcggtggcct tttaccgtgg cctcgacgta tctgtcattc
4621 caactacagg agacgtcgtt gttgtagcga ccgacgcctt gatgactggc ttcaccggag
4681 atttcgactc tgtgatagac tgcaacacct gtgtcgtcca gacagtcgac ttcagcctag
4741 accctatatt ctctattgag acttccaccg tgccccagga cgccgtgtcc cgctcccaac
4801 ggagggggtag gaccggtcga gggaagcatg gtatttacag atatgtgtca cccgggggagc
4861 ggccgtctgg catgttcgac tccgtggtcc tctgtgagtg ctatgacgcg ggttgtgctt
4921 ggtacgagct tacacccgcc gagaccacag tcaggctacg ggcatacctc aacaccccag
4981 gattgcccgt gtgccaggac cacttggagt tctgggagag tgtcttcacc ggcctcaccc
5041 acatagatgc ccacttcctg tcccagacga aacagagtgg ggagaacttc ccctacctag
5101 tcgcatacca agccaccgtg tgcgctagag ctagagctcc tcccccgtca tgggaccaaa
5161 tgtggaagtg cctgatacgg ctcaagccca ccctcactgg ggctacccca ttactataca
5221 gactgggtag tgtacagaat gagatcacct taacacaccc aatcacccaa tacatcatgg
5281 cttgcatgtc ggcggacctg gaggtcgtca ctagcacgtg ggtgttggtg ggcggcgtcc Fig. 10 continued SEQ ID No.1

5341 tagccgcttt ggccgcttac tgcctgtcca caggcagcgt ggtcatagtg ggcaggataa
5401 tcctaggtgg gaagccggca gtcatacctg acagggaggt tctctaccga gagtttgatg
5461 agatggagga gtgcgccgcc cacgtcccct acctcgagca ggggatgcat ttggcggagc
5521 agttcaagca gaaagctctt gggttgctcc agacggcatc caaacaaaca gagacgatca
5581 ctcccattgt ccagtctaat tggcagaagc tcgagtcttt ctgggctaaa cacatgtgga
5641 acttcgttag cgggatacaa tatctggcgg gcctatcaac gctgcccggg aaccccgcta
5701 tagcatcgct gatgtcgttt acggccgcag tgacgagtcc actaaccact cagcagaccc
5761 tcctctttaa catcttgggg gggtggctgg ctgcccagct tgccgcccca gccgccgcca
5821 cagccttcgt tggcgcaggc attactggcg ccgttgttgg cagtgtgggc ctagggaagg
5881 tcctggtgga cattcttgcc ggctacgggg ctggtgtggc cggggccctc gtggctttca
5941 aaatcatgag cggggagacc cccaccacgg aggatctagt caaccttctg cctgccatcc
6001 tatcgccagg agctctcgtt gtcgccgtgg tgtgcgcagc aatactacgc cggcacgtgg
6061 gccttggcga gggcgccgtg cagtggatga accggctgat agcgtttgct tctcggggta
6121 accacgtctc ccctacacac tacgtgccgg agagcgacgc gtcggctcgt gtcacaccaa
6181 ttctcaccag gctcactgtt actcagcttc tgaaagggct ccacgtgtgg ataagctcga
6241 attgcatcgc cccgtgtgct agttcttggc ttaaagatgt ctggaactgg atatgcgagg
6301 tgctgagcga cttcaagaat tggctgaagg ccaaacttgt accacaactg cccgggatcc
6361 cattcgtatc ctgccaacgc gggtaccgtg gggtctggcg gggcgagggc atcgtgcaca
6421 ctcgttgccc gtgtggggcc aatataactg gacatgtcaa gaacggttcg atgagaatcg
6481 tcgggcctaa gacttgcagc aacacctggc gtgggtcgtt ccccattaac gcttacacta
6541 caggcccgtg cacgccctcc ccggcgccga actatacgtt cgcgctatgg agggtgtctg
6601 cagaggagta tgtggaggta aggcggctgg gggacttcca ttacgtcacg gggtgacca
6661 ctgataaact caagtgtcca tgccaggtcc cctcacccga gttctccaca gaggtggacg
6721 gggtgcgcct gcataggtac gcccctccct gcaaacccct gctacgggat gaggtgacgt
6781 ttagcgtcgg gttcaatgaa tacctggtgg ggtcccagtt gccctgcgag cccgagccag
6841 acgtagcagc attaacatca atgcttacag acccttccca catcactgca aagacggcgg
6901 cgcgtaggct gaagcggggg tctcccccct ccctggccag ttcttctgcc agccagctgt
6961 ccgcgccgtc actgaaagca acatgcacca ctcaccatga ctctccagac gccgacctca
7021 tagaagccaa cctcctgtgg agacggggaga tgggggggaa catcaccaga gtggagtcgg
7081 agaacaagat tgttgttctg gattctttcg acccgctcgt ggcagaggag gatgaccggg
7141 agatttctat tccagctgag attctgcgga aatttaagca gtttcccccc gccatgccca
7201 tatgggcacg gccggattat aatcctcccc ttgtggaacc gtggaagcgc ccggactgtg
7261 atccaccctt agtccacggg tgcccccctac cacctcccaa gccgactccg gtgccgccac
7321 cccggaaaaa gaggacggtg gtgctggacg agtctacagt atcatctgct ctggctgagc
7381 ttgccactaa gaccttcggc agctctacaa cctcaggcgt gacaagtggt gaagcggccg
7441 aatcgtcccc ggcgctttcc tgcgacggtg agctggactc cgaagctgaa tcttactcct
7501 ccatgccccc tctcgagggg gaaccggggg accccgatct cagcgacggg tcttggtcta
7561 ccgtgagcag tgatggcggt acggaggatg tcgtgtgctg ctcgatgtcc tactcgtgga
7621 cgggcgcctt aattacgccc tgtgccgcag aggaaaccaa actccccatc aacgcactga
7681 gtaactcgct gctgcgccac cacaatttgg tgtattccac cacctctcgc agcgctggca
7741 agaggcagaa aaaagtcaca tttgacaggc tgcaggtcct ggacgatcat taccgggacg
7801 tgctcaagga ggctaaggcc aaggcatcca cagtgaaggc taaattgcta tccgtagagg
7861 aggcatgtag cctgacgccc ccgcactccg ccagatcaaa atttggctat gggccgaagg
7921 atgtccgaag ccattccagt aaggctatac gccacatcaa ctccgtgtgg caggaccttc
7981 tggaggacaa tacaacacct atagacacta ccatcatggc caagaatgaa gtcttctgcg
8041 tgaaggccga aaaagggggt cgcaagcccg ctcgccttat cgtgtacccc gacctggggg Fig. 10 continued SEQ ID No.1

8101 tgcgcgtgtg cgagaagaga gctttgtatg acgtagtcaa acagctcccc attgccgtga
8161 tgggaccctc ctacgggttc cagtactcgc cagcgcagcg ggtcgacttc ctgcttaacg
8221 cgtggaaatc aaagaaaaac cctatggggt tttcctatga cacccgttgc tttgactcaa
8281 cagtcactga ggctgatatc cgtacggagg aagacctcta tcaatcttgt gacctggtcc
8341 ctgaggcccg cgcggccata aggtctctca cagagaggct ttacatcggg ggcccactta
8401 ccaattctaa gggacaaaac tgcggctatc ggcgatgccg cgcaagcggc gtgctgacca
8461 ctagctgcgg taacaccata acttgctacc ttaaggctag tgcggcctgt cgagctgcaa
8521 agctccagga ctgcaccatg ctcgtgtgcg gcgacgacct cgtcgttatc tgtgaaagcg
8581 ccggtgtcaa ggaggacgct gcgagcctga gagccttcac cgaggctatg accaggtact
8641 ccggcccccc gggagacccg gctcaaccag aatacgactt ggagcttata acatcctgct
8701 cctccaatgt gtcggtcgcg cgcgacggcg ctggccaaag ggtctattat ctgacccgtg
8761 aacctgagac tcccctcgcg cgtgccgctt gggagacagc aagacacact ccagtgaact
8821 cctggctagg caacatcatc atgtttgccc ccactctgtg ggtacggatg gtcctcatga
8881 cccacttatt ctccatactc atagttcagg agcaccttga aaaggctcta gattgtgaaa
8941 tctatggagc cacacactcc gtcccaccgt tggacctacc tgaaatcatt caaagactcc
9001 atggcctcag cgcgttttcg ctccacagtt actctccagg tgaaatcaat agggtggctt
9061 catgcctcag gaaacttggg gttccaccct tgcgagcttg gagacaccgg gcccggagcg
9121 tccgcgccac actcctatcc caggggggga aagccgccat atgcggtaag tacctcttca
9181 actgggcggt gaaaaccaaa ctcaaactca ttccattacc gctcgcgtct catttggact
9241 tgtccaattg gttcacgggc ggctacagcg gggagacat ttatcacagc gtgtctcatg
9301 cccggccccg ttggtttctc tggtgcctac tcctactctc agtaggggta ggcatctacc
9361 tccttcccaa ccgatagacg gttgggcaac cactccaggc ctttaggccc tatttaaaca
9421 ctccaggcct ttaggccccg t

Fig: 11

```
                 10        20        30        40        50        60
HCV1    GCCAGCCCCCTGATGGGGGCGACACTCCACCATGAATCACTCCCCTGTGAGGAACTACTG
        :::::::::::::::::::::::::::: :::::::::::::::::::::::::::::::
AY6510  GCCAGCCCCCTGATGGGGGCGACACTCCGCCATGAATCACTCCCCTGTGAGGAACTACTG
                 10        20        30        40        50        60

                 70        80        90       100       110       120
HCV1    TCTTCACGCAGAAAGCGTCTAGCCATGGCGTTAGTATGAGTGTCGTGCAGCCTCCAGGAC
        ::::::::::::::::::::::::::::::::::::::::::::::::::::::::::::
AY6510  TCTTCACGCAGAAAGCGTCTAGCCATGGCGTTAGTATGAGTGTCGTGCAGCCTCCAGGAC
                 70        80        90       100       110       120

                130       140       150       160       170       180
HCV1    CCCCCCTCCCGGGAGAGCCATAGTGGTCTGCGGAACCGGTGAGTACACCGGAATTGCCAG
        ::::::::::::::::::::::::::::::::::::::::::::::::::::::::::::
AY6510  CCCCCCTCCCGGGAGAGCCATAGTGGTCTGCGGAACCGGTGAGTACACCGGAATTGCCAG
                130       140       150       160       170       180

                190       200       210       220       230       240
HCV1    GACGACCGGGTCCTTTCTTGGATCAACCCGCTCAATGCCTGGAGATTTGGGCGTGCCCCC
        ::::::::::::::::::::::: ::::::::::: ::::::::::::::::::::::::
AY6510  GACGACCGGGTCCTTTCTTGGATAAACCCGCTCAACGCCTGGAGATTTGGGCGTGCCCCC
                190       200       210       220       230       240

                250       260       270       280       290       300
```

```
HCV1    GCAAGACTGCTAGCCGAGTAGTGTTGGGTCGCGAAAGGCCTTGTGGTACTGCCTGATAGG
        ::::::::::::::::::::::::::::::::::::::::::::::::::::::::::::
AY6510  GCAAGACTGCTAGCCGAGTAGTGTTGGGTCGCGAAAGGCCTTGTGGTACTGCCTGATAGG
                  250       260       270       280       290       300

                  310       320       330       340
HCV1    GTGCTTGCGAGTGCCCCGGGAGGTCTCGTAGACCGTGCACC
        :::::::::::::::::::::::::::::::::::::::::
AY6510  GTGCTTGCGAGTGCCCCGGGAGGTCTCGTAGACCGTGCACC
                  310       320       330       340
```

Fig: 12

```
        10   20   30   40   50   60
HCV1    ATGAGCACGAATCCTAAACCTCAAAAAAAAAACAAACGTAACACCAACCGTCGCCCACAG
        ::::::::::::::::::::::::: ::::: ::::::::::::::::::::::::::::
AY6510  ATGAGCACGAATCCTAAACCTCAAAGAAAAACCAAACGTAACACCAACCGTCGCCCACAG
                  10        20        30        40        50        60

                  70        80        90        100       110       120
HCV1    GACGTCAAGTTCCCGGGTGGCGGTCAGATCGTTGGTGGAGTTTACTTGTTGCCGCGCAGG
        ::::::::::::::::::::::: ::::::::::::::::::::::::::::::::::::
AY6510  GACGTCAAGTTCCCGGGTGGCGGACAGATCGTTGGTGGAGTTTACTTGTTGCCGCGCAGG
                  70        80        90        100       110       120

                  130       140       150       160       170       180
HCV1    GGCCCTAGATTGGGTGTGCGCGCGACGAGAAAGACTTCCGAGCGGTCGCAACCTCGAGGT
        ::::::::::::::::::::::::::: ::::::::::::::::::::::::::::::::
AY6510  GGCCCTAGATTGGGTGTGCGCGCGACGAGGAAGACTTCCGAGCGGTCGCAACCTCGAGGT
                  130       140       150       160       170       180

                  190       200       210       220       230       240
HCV1    AGACGTCAGCCTATCCCCAAGGCTCGTCGGCCCGAGGGCAGGACCTGGGCTCAGCCCGGG
        ::::::::::::::::::::::: ::::::::::::::::::::::::::::::::::::
AY6510  AGACGTCAGCCTATCCCCAAGGCACGTCGGCCCGAGGGCAGGACCTGGGCTCAGCCCGGG
                  190       200       210       220       230       240

                  250       260       270       280       290       300
HCV1    TACCCTTGGCCCCTCTATGGCAATGAGGGCTGCGGGTGGGCGGGATGGCTCCTGTCTCCC
        ::::::::::::::::::::::::::::::::::::::::::::::::::::::::::::
AY6510  TACCCTTGGCCCCTCTATGGCAATGAGGGCTGCGGGTGGGCGGGATGGCTCCTGTCTCCC
                  250       260       270       280       290       300

                  310       320       330       340       350       360
HCV1    CGTGGCTCTCGGCCTAGCTGGGGCCCCACAGACCCCCGGCGTAGGTCGCGCAATTTGGGT
        :: :::::::::::::: :::::::::::::::::::::::::: :::::::::::::::
AY6510  CGCGGCTCTCGGCCTAGTTGGGGCCCCACAGACCCCCGGCGTAGATCGCGCAATTTGGGT
                  310       320       330       340       350       360

                  370       380       390       400       410       420
HCV1    AAGGTCATCGATACCCTTACGTGCGGCTTCGCCGACCTCATGGGGTACATACCGCTCGTC
        :::::::::::::::::::::: :::::::::::::::::::::::::::::::::::::
AY6510  AAGGTCATCGATACCCTTACGTATGGCTTCGCCGACCTCATGGGGTACATACCGCTCGTC
                  370       380       390       400       410       420

                  430       440       450       460       470       480
HCV1    GGCGCCCCTCTTGGAGGCGCTGCCAGGGCCCTGGCGCATGGCGTCCGGGTTCTGGAAGAC
```

Fig. 12 continued

```
        :::::::: ::::: :::::::::::::::::::::::: ::::::::::: :::::::::
AY6510  GGCGCCCCCCTTGGGGGCGCTGCCAGGGCCCTGGCGCACGGCGTCCGGGTCCTGGAAGAC
                430       440       450       460       470       480

                490       500       510       520       530       540
HCV1    GGCGTGAACTATGCAACAGGGAACCTTCCTGGTTGCTCTTTCTCTATCTTCCTTCTGGCC
        ::::::::::::::::::::::::::::::::::::::::::::::::::::::::::::
AY6510  GGCGTGAACTATGCAACAGGGAACCTTCCTGGTTGCTCTTTCTCTATCTTCCTTCTGGCC
                490       500       510       520       530       540

                550       560       570
HCV1    CTGCTCTCTTGCTTGACTGTGCCCGCTTCGGCC
        :::::::::::::::::::::::::::::::::
AY6510  CTGCTCTCTTGCTTGACTGTGCCCGCTTCGGCC
                550       560       570
```

FIG: 13

```
                10        20        30        40        50        60
HCV1    AGTGCGCAACTCCACGGGGCTTTACCACGTCACCAATGATTGCCCTAACTCGAGTATTGT
        ::::::::::::  ::::: : ::::: :::::::::::::::: ::   ::   : ::::
AY6510  AGTGCGCAACTCTTCGGGGGTGTACCATGTCACCAATGATTGCCCCAATGCGTCTGTTGT
                10        20        30        40        50        60

                70        80        90       100       110       120
HCV1    GTACGAGGCGGCCGATGCCATCCTGCACACTCCGGGGTGCGTCCCTTGCGTTCGTGAGGG
        ::::::: : :          ::: : ::    :::::::: :: :: ::::: :: :::::
AY6510  GTACGAGACAGATAGCTTGATCATACATCTGCCGGGGTGTGTGCCCTGCGTACGCGAGGG
                70        80        90       100       110       120

               130       140       150       160       170       180
HCV1    CAACGCCTCGAGGTGTTGGGTGGCGATGACCCCTACGGTGGCCACCAGGGATGGCAAACT
        :::::  :::::::: :::::   :   :  :  ::::: :: ::: : : ::::        :
AY6510  CAACGGTTCGAGGTGCTGGGTCTCCCTTAGTCCTACTGTTGCCGCTAAGGATCCGGGCGT
               130       140       150       160       170       180

               190       200       210       220       230       240
HCV1    CCCCG-CGACGCAGCTTCGACGTCACATCGATCTGCTTGTCGGGAGCGCCACCCTCTGTT
        ::: : : ::: :: :::: :::::: :::: ::: ::: ::::   :::   :   ::::::
AY6510  CCCGGTCAACG-AGATTCGGCGTCACGTCGACCTGATTGCCGGGGCCGCTGCATTCTGTT
               190       200       210       220       230       240

               250       260       270       280       290       300
HCV1    CGGCCCTCTACGTGGGGGACCTATGCGGGTCTGTCTTTCTTGTCGGCCAACTGTTCACCT
        ::::   : :: :: ::: :: ::::::: ::   :::: :: :: ::::: :: ::::::
AY6510  CGGCTATGTATGTAGGGCACTTATGCGGTTCCATCTTCCTCGTTGGCCAGCTTTTCACCC
               250       260       270       280       290       300

               310       320       330       340       350       360
HCV1    TCTCTCCCAGGCGCCACTGGACGACGCAAGGTTGCAATTGCTCTATCTATCCCGGCCATA
        :::: :: ::::::::::::: :: ::::   :: :::::::: ::::: :: :: :::
AY6510  TCTCCCCTAGGCGCCACTGGACAACACAAGACTGTAATTGCTCCATCTACCCAGGACATG
               310       320       330       340       350       360
```

Fig. 13 continued

```
               370       380       390       400       410       420
HCV1   TAACGGGTCACCGCATGGCATGGGATATGATGATGAACTGGTCCCCTACGACGGCGTTGG
       : :: :: :: :: ::::: ::::: :::::::::::::::::::::::::::::: :::
AY6510 TGACAGGCCATCGAATGGCTTGGGACATGATGATGAACTGGTCCCCTACGACGGCGCTGG
               370       380       390       400       410       420

               430       440       450       460       470       480
HCV1   TAATGGCTCAGCTGCTCCGGATCCCACAAGCCATCTTGGACATGATCGCTGGTGCTCACT
       :: : :: ::::::::::::::::::::::::::::::::::::::::::::::::::::
AY6510 TAGTAGCCCAGCTGCTCCGGATCCCACAAGCCATCTTGGACATGATCGCTGGTGCTCACT
               430       440       450       460       470       480

               490       500       510       520       530       540
HCV1   GGGGAGTCCTGGCGGGCATAGCGTATTTCTCCATGGTGGGGAACTGGGCGAAGGTCCTGG
       ::::::::::::::::::::::::::::::::::::::::::::::: ::::::::::::
AY6510 GGGGAGTCCTGGCGGGCATAGCGTATTTCTCCATGGTGGGGAACTGGACGAAGGTCCTGG
               490       500       510       520       530       540

               550       560       570
HCV1   TAGTGCTGCTGCTATTTGCCGGCGTCGACGCG
       ::::::::::::::::::::::::::::::::
AY6510 TAGTGCTGCTGCTATTTGCCGGCGTCGACGCG
               550       560       570
```

Fig: 14

```
                10        20        30        40        50        60
HCV1   ACCCACGTCACCGGGGGAAGTGCCGGCCACACTGTGTCTGGATTTGTTAGCCTCCTCGCA
       :::  :::: :::::::::::::::::: ::    : ::::: ::::: : ::: :: ::
AY6510 ACCATCGTCTCCGGGGGAAGTGCCGGCCGCAGCACGGCTGGACTTGTTGGGCTCTTCTCA
                10        20        30        40        50        60

                70        80        90       100       110       120
HCV1   CCAGGCGCCAAGCAGAACGTCCAGCTGATCAACACCAACGGCAGTTGGCACCTCAATAGC
       :::::::::  ::::::: :::::::::::::::::::::::::::::::: ::::  ::
AY6510 CCAGGCGCCCGGCAGAACATCCAGCTGATCAACACCAACGGCAGTTGGCACATCAACCGC
                70        80        90       100       110       120

               130       140       150       160       170       180
HCV1   ACGGCCCTGAACTGCAATGATAGCCTCAACACCGGCTGGTTGGCAGGGCTTTTCTATCAC
       :::::::::::::::::::::: :::  : ::::::::: : :::::::::::::::  :
AY6510 ACGGCCCTGAACTGCAATGATACCCTTCAAACCGGCTGGGTAGCAGGGCTTTTCTATACC
               130       140       150       160       170       180

               190       200       210       220       230       240
HCV1   CACAAGTTCAACTCTTCAGGCTGTCCTGAGAGGCTAGCCAGCTGCCGACCCCTTACCGAT
        :::: ::::::::::: :: :: :: :::::: : :::::::::::::::::: :::: 
AY6510 AACAAATTCAACTCTTCGGGTTGCCCCGAGAGGTTGGCCAGCTGCCGACCCCTTGCCGAC
               190       200       210       220       230       240

               250       260       270       280       290       300
HCV1   TTTGACCAGGGCTGGGGCCCTATCAGTTATGCCAACGGAAGCGGCCCCGACCAGCGCCCC
       :::::::::::::::::::::::::::::: ::::::::::::::::::::::: ::::::
AY6510 TTTGACCAGGGCTGGGGCCCTATCAGTTATACCAACGGAAGCGGCCCCGACCAACGCCCC
               250       260       270       280       290       300

               310       320       330       340       350       360
```

```
HCV1    TACTGCTGGCACTACCCCCCAAAACCTTGCGGTATTGTGCCCGCGAAGAGTGTGTGTGGT
        ::::::::::::::::::::::::::::::::: :::::::::::::  ::::  :::::::
AY6510  TACTGCTGGCACTACCCCCCAAAACCTTGTGGTATTGTGCCCGCAGAGAGCGTGTGTGGC
             310       320       330       340       350       360

             370       380       390       400       410       420
HCV1    CCGGTATATTGCTTCACTCCCAGCCCCGTGGTGGTGGGAACGACCGACAGGTCGGGCGCG
        ::  :::::  ::::::::::::::::::::::::::::::::::::::::::::::::::
AY6510  CCAGTATACTGCTTCACTCCCAGCCCCGTGGTGGTGGGAACGACCGACAGGTCGGGCGCG
             370       380       390       400       410       420

             430       440       450       460       470       480
HCV1    CCCACCTACAGCTGGGGTGAAAATGATACGGACGTCTTCGTCCTTAACAATACCAGGCCA
        :::::::::   ::::::::::::::: :::::::::: :::::::: :::::  :::::::
AY6510  CCCACCTACAACTGGGGTGAAAATGAAACGGACGTTTTCGTCCTCAACAACACCAGGCCA
             430       440       450       460       470       480

             490       500       510       520       530       540
HCV1    CCGCTGGGCAATTGGTTCGGTTGTACCTGGATGAACTCAACTGGATTCACCAAAGTGTGC
        : :::::::::::::::::::::: ::::::::::::::::::::::::::::: ::::::
AY6510  CGGCTGGGCAATTGGTTCGGTGGTACCTGGATGAACTCAACTGGATTCACCAAGGTGTGC
             490       500       510       520       530       540

             550       560       570       580       590       600
HCV1    GGAGCGCCTCCTTGTGTCATCGGAGGGGCGGGCAACAACACCCTGCACTGCCCCACTGAT
        :::::::::  ::::::  ::::::::::  :::::::::::::  ::::::::::::::::
AY6510  GGAGCGCCCCCTTGTGCCATCGGAGGGGTGGGCAACAACACCTTGTACTGCCCCACTGAT
             550       560       570       580       590       600

             610       620       630       640       650       660
HCV1    TGCTTCCGCAAGCATCCGGACGCCACATACTCTCGGTGCGGCTCCGGTCCCTGGATCACA
        :: :::::::::  ::::::: :::::  ::::::::::::::::::::::: ::::: :::
AY6510  TGTTTCCGCAAACATCCGGAAGCCACGTACTCTCGGTGCGGCTCCGGTCCTTGGATTACA
             610       620       630       640       650       660

             670       680       690       700       710       720
HCV1    CCCAGGTGCCTGGTCGACTACCCGTATAGGCTTTGGCATTATCCTTGTACCATCAACTAC
        :::::::::::  :: :: ::::::::::::::::::::::::::::::::::::: :::
AY6510  CCCAGGTGCTTGATCCACTACCCGTATAGGCTTTGGCATTATCCTTGTACCATCAATTAC
             670       680       690       700       710       720

             730       740       750       760       770       780
HCV1    ACCATATTTAAAATCAGGATGTACGTGGAGGGGTCGAACACAGGCTGGAAGCTGCCTGC
        :::::::::  :: ::::::::::: :::::  :: ::::::::: :: :: :: :::
AY6510  ACCATATTCAAGATCAGGATGTTTGTGGCGGGGTTGAGCACAGGCTCGACGCCGCGTGC
             730       740       750       760       770       780

             790       800       810       820       830       840
HCV1    AACTGGACGCGGGGCGAACGTTGCGATCTGGAAGACAGGGACAGGTCCGAGCTCAGCCCG
        :::::::::::::::  :: ::::: :::: :::::::  :::::: : :::::
AY6510  AACTGGACGCGGGGAGAGCGCTGCGACTTGGACGACAGGGATCGGGCCGAGTTGAGCCCT
             790       800       810       820       830       840

             850       860       870       880       890       900
HCV1    TTACTGCTGACCACTACACAGTGGCAGGTCCTCCCGTGTTCCTTCACAACCCTACCAGCC
        :   ::::: ::::::::  :::::::::::::: :: :: :::::::: :: :: :::
AY6510  CTGTTGCTGTCCACTACGCAATGGCAGGTCCTCCCCCTGCTCATTCACAACACTGCCCGCC
```

```
               850       860       870       880       890       900

               910       920       930       940       950       960
HCV1    TTGTCCACCGGCCTCATCCACCTCCACCAGAACATTGTGGACGTGCAGTACTTGTACGGG
         :::: :: ::::: :: :: :::::::::::::: ::::::::::::::: : :: :::
AY6510  CTGTCAACTGGCCTGATACATCTCCACCAGAACATCGTGGACGTGCAGTACCTCTATGGG
               910       920       930       940       950       960

               970       980       990      1000      1010      1020
HCV1    GTGGGGTCAAGCA-TCGCGTCCTGGGCCATTAAGTGGGAGTACGTCGTTCTCCTGTTCCT
         :: : ::  ::: :: : ::::::: ::: :::::::::::::: :: ::::: ::: :
AY6510  TTGAGCTCG-GCAGTCACATCCTGGGTCATAAAGTGGGAGTACGTTGTGCTCCTCTTCTT
               970       980       990      1000      1010      1020

              1030      1040      1050      1060      1070      1080
HCV1    TCTGCTTGCAGACGCGCGCGTCTGCTCCTGCTTGTGGATGATGCTACTCATATCCCAAGC
         ::::: ::::: :: ::: : ::  :::::::::::::::::::: :::::::: :: :
AY6510  GCTGCTAGCAGATGCTCGCATTTGTGCCTGCTTGTGGATGATGCTTCTCATATCTCAGGT
              1030      1040      1050      1060      1070      1080

              1090      1100      1110      1120      1130      1140
HCV1    GGAGGCGGCTTTGGAGAACCTCGTAATACTTAATGCAGCATCCCTGGCCGGGACGCACGG
         ::::::::  :::::::: :  :: : :: :: :: :: ::::: : ::::::: :: ::
AY6510  AGAGGCGGCGCTGGAGAACTTGATAGTTCTCAACGCTGCTTCCCTAGTCGGGACACATGG
              1090      1100      1110      1120      1130      1140

              1150      1160      1170      1180      1190      1200
HCV1    TCTTGTATCCTTCCTCGTGTTCTTCTGCTTTGCATGGTATTTGAAGGGTAAGTGGGTGCC
          : ::  ::::: :: : :: :: ::    :: :::::  : :: :: :::::::  ::
AY6510  CATCGTCCCCTTCTTCATCTTTTTTTGTGCAGCTTGGTACCTAAAAGGCAAGTGGGCCCC
              1150      1160      1170      1180      1190      1200

              1210      1220      1230      1240      1250      1260
HCV1    CGGAGCGGTCTACACCTTCTACGGGATGTGGCCTCTCCTCCTGCTCCTGTTGGCGTTGCC
         :::   : :::  :: :::: ::::::::::: :: :::::::: ::  ::::::::::
AY6510  TGGACTCGCCTATTCCGTCTATGGGATGTGGCCACTGCTCCTGCTTCTCCTGGCGTTGCC
              1210      1220      1230      1240      1250      1260

              1270
HCV1    CCAGCGGGCGTACGC
        ::: ::::: :::::
AY6510  CCAACGGGCATACGC
              1270
```

FIG: 15

```
                10        20        30        40        50        60
HCV1    TGGACACGGAGGTGGCCGCGTCGTGTGGCGGTGTTGTTCTCGTCGGGTTGATGGCGCTGA
        ::::   :::: :::::::::::::::: :     ::  :: :: :  :   :: ::: :
AY6510  TGGATCAGGAGTTGGCCGCGTCGTGTGGGGCCACGGTCTTCATCTGCCTAGCGGTGCTCA
                10        20        30        40        50        60

                70        80        90       100       110       120
HCV1    CTCTGTCACCATATTACAAGCGCTATATCAGCTGGTGCTTGTGGTGGCTTCAGTATTTTC
        :::: :: ::::::::::: :  :: ::   : :  :: : :::::::: :::::  : :
AY6510  CTCTATCGCCATATTACAAACAGTACATGGCCCGCGGCATCTGGTGGCTGCAGTACATGC
                70        80        90       100       110       120
```

Fig. 15 continued

```
               130       140       150       160       170       180
HCV1    TGACCAGAGTGGAAGCGCAACTGCACGTGTGGATTCCCCCCCTCAACGTCCGAGGGGGGC
        :::::::::  :: ::::  :: :: :: ::: : ::::: ::::::: :::::: ::::
AY6510  TGACCAGAGCAGAGGCGCTCCTACAGGTTTGGGTCCCCCCGCTCAACGCCCGAGGAGGGC
               130       140       150       160       170       180

               190       200       210       220       230       240
HCV1    GCGACGCCGTCATCTTACTCATGTGTGCTGTACACCCG-ACTCTGGTATTTGACATCACC
        ::::::  ::: :  : :::: :::::   : :::::: ::: :: : ::::: ::::::
AY6510  GCGACGGAGTCGTACTGCTCACGTGTGTGCTCCACCCGCACT-TGCTCTTTGAAATCACC
               190       200       210       220       230       240

               250       260       270       280       290       300
HCV1    AAATTGCTGCTGGCCGTCTTCGGACCCCTTTGGATTCTTCAAGCCAGTTTGCTTAAAGTA
        ::  :  :::::::: :  :::: ::  : :::::  : :: :::::: :::: :: :::
AY6510  AAGATCATGCTGGCCATTCTCGGGCCTTTGTGGATCTTGCAGGCCAGTCTGCTCAAGGTA
               250       260       270       280       290       300

               310       320       330       340       350       360
HCV1    CCCTACTTTGTGCGCGTCCAAGGCCTTCTCCGGTTCTGCGCGTTAGCGCGGAAGATGATC
        :: ::::: :::::::: :: :::::::::::: :::::::: :::::::::::::: ::
AY6510  CCGTACTTCGTGCGCGTTCAGGGCCTTCTCCGGATCTGCGCGCTAGCGCGGAAGATGGTC
               310       320       330       340       350       360

               370       380       390       400       410       420
HCV1    GGAGGCCATTACGTGCAAATGGTCATCATTAAGTTAGGGGCGCTTACTGGCACCTATGTT
        ::::::::::::::::::::::::: ::: :::::::::::::: :::::::::::: ::
AY6510  GGAGGCCATTACGTGCAAATGGTCACCATCAAGTTAGGGGCGCTCACTGGCACCTATATT
               370       380       390       400       410       420

               430       440       450       460       470       480
HCV1    TATAACCATCTCACTCCTCTTCGGGACTGGGCGCACAACGGCTTGCGAGATCTGGCCGTG
        :::::::::::::::::::::::::::::::::::::::::::::: ::: :: ::::: 
AY6510  TATAACCATCTCACTCCTCTTCGGGACTGGGCGCACAACGGCTTGCAAGACCTAGCCGTA
               430       440       450       460       470       480

               490       500       510       520       530       540
HCV1    GCTGTAGAGCCAGTCGTCTTCTCCCAAATGGAGACCAAGCTCATCACGTGGGGGGCAGAT
        ::::: ::::::::::::::::::::::::::::::::::::::::::::::::::::: 
AY6510  GCTGTGGAGCCAGTCGTCTTCTCCCAAATGGAGACCAAGCTCATCACGTGGGGGGCAGAC
               490       500       510       520       530       540

               550       560       570       580       590
HCV1    ACCGCCGCGTGCGGTGACATCATCAACGGCTTGCCTGTTTCCGCCCGCAGG
        :: :::::::: ::::::::::::::::::::::: :: ::::::::::::
AY6510  ACAGCCGCGTGTGGTGACATCATCAACGGCTTGCCCGTCTCCGCCCGCAGG
               550       560       570       580       590
```

Fig: 16

```
                10        20        30        40        50        60
HCV1    GGCCGGGAGATACTGCTCGGGCCAGCCGATGGAATGGTCTCCAAGGGGTGGAGGTTGCTG
        :::: ::::::::::::::: ::::::::::::::::: ::: : ::: :::::::::::
AY6510  GGCCAGGAGATACTGCTCGGACCAGCCGATGGAATGGCCTCTAGGGGATGGAGGTTGCTG
                10        20        30        40        50        60
```

Fig. 16 continued

```
                  70        80        90       100       110       120
HCV1    GCGCCCATCACGGCGTACGCCCAGCAGACAAGGGGCCTCCTAGGGTGCATAATCACCAGC
        :::::::::::::::::::: :::::::::::::::::::::::::: ::::::::::::
AY6510  GCGCCCATCACGGCGTACGCTCAGCAGACAAGGGGCCTCCTAGGGTGTATAATCACCAGC
                  70        80        90       100       110       120

                 130       140       150       160       170       180
HCV1    CTAACTGGCCGGGACAAAAACCAAGTGGAGGGTGAGGTCCAGATTGTGTCAACTGCTGCC
        :: :::::::::::::: ::::::::::::::::: ::::::::::::::::::::::::
AY6510  CTGACTGGCCGGGACAAGAACCAAGTGGAGGGTGAAGTCCAGATTGTGTCAACTGCTGCC
                 130       140       150       160       170       180

                 190       200       210       220       230       240
HCV1    CAAACCTTCCTGGCAACGTGCATCAATGGGGTGTGCTGGACTGTCTACCACGGGGCCGGA
        ::::: ::: :::: ::::::::::: ::::: :::::::::::::::::::::::::::
AY6510  CAAACGTTCTTGGCGACGTGCATCAACGGGGTATGCTGGACTGTCTACCACGGGGCCGGA
                 190       200       210       220       230       240

                 250       260       270       280       290       300
HCV1    ACGAGGACCATCGCGTCACCCAAGGGTCCTGTCATCCAGATGTATACCAATGTAGACCAA
        :: :::::::: :: ::: ::::::::::::: :: :  :::::::::::::::::::::
AY6510  ACCAGGACCATTGCATCATCCAAGGGTCCTGTTATTCTAATGTATACCAATGTAGACCAA
                 250       260       270       280       290       300

                 310       320       330       340       350       360
HCV1    GACCTTGTGGGCTGGCCCGCTCCGCAAGGTAGCCGCTCATTGACACCCTGCACTTGCGGC
        ::::: : ::::::: ::::::: ::::    : ::::: :::::::::: :  ::::::
AY6510  GACCTCGGGGGCTGGACCGCTCCTCAAGTGCTCGGCTCACTGACACCCTGGAGCTGCGGC
                 310       320       330       340       350       360

                 370       380       390       400       410       420
HCV1    TCCTCGGACCTTTACCTGGTCACGAGGCACGCCGATGTCATTCCCGTGCGCCGGCGGGGT
        ::::::::::::::::::::::::::::: :::::::::::::::::::  ::::: :::
AY6510  TCCTCGGACCTTTACCTGGTCACGAGGCATGCCGATGTCATTCCCGTGCCGCGGCGAGGT
                 370       380       390       400       410       420

                 430       440       450       460       470       480
HCV1    GATAGCAGGGGCAGCCTGCTGTCGCCCCGGCCCATTTCCTACTTGAAAGGCTCCTCGGGG
        :: : ::::::::::::::: ::::::::::::::::::::  : :: :: :::::::: 
AY6510  GAAACCAGGGGCAGCCTGCTTTCGCCCCGGCCCATTTCCTATCTAAAGGGATCCTCGGGA
                 430       440       450       460       470       480

                 490       500       510       520       530       540
HCV1    GGTCCGCTGTTGTGCCCCGCGGGGCACGCCGTGGGCATATTTAGGGCCGCGGTGTGCACC
        :: :: ::: : :: :::  ::: :: ::::::::::: :: ::::::::::::::::::
AY6510  GGCCCCCTGCTCTGTCCCATGGGACATGCCGTGGGCATTTTCAGGGCCGCGGTGTGCACC
                 490       500       510       520       530       540

                 550       560       570       580       590       600
HCV1    CGTGGAGTGGCTAAGGCGGTGGACTTTATCCCTGTGGAGAACCTAGAGACAACCATGAGG
        ::::: :: :: :::::::: :::::: : :: :: :::  : ::::::: :::::::::
AY6510  CGTGGGGTCGCAAAGGCGGTCGACTTTGTGCCCGTTGAGTCCTTAGAGACCACCATGAGG
                 550       560       570       580       590       600

                 610       620       630       640       650       660
HCV1    TCCCCGGTGTTCACGGATAACTCCTCTCCACCAGTAGTGCCCCAGAGCTTCCAGGTGGCT
```

Fig. 16 continued

```
          :::::   :::::  ::  ::  ::  :::       ::  :  :  ::::::::::::  :  :::::::::
AY6510  TCCCCAGTGTTTACTGACAATTCCAGCCCTCTAACAGTGCCCCAGAGTTACCAGGTGGCG
            610       620       630       640       650       660

            670       680       690       700       710       720
HCV1    CACCTCCATGCTCCCACAGGCAGCGGCAAAAGCACCAAGGTCCCGGCTGCATATGCAGCT
        ::  ::  :::::   :::::  ::  ::  :::::   :::::  :::::  ::  ::  :::::::
AY6510  CATCTACATGCACCCACTGGGAGTGGCAAGAGCACGAAGGTGCCGGCCGCTTACGCAGCT
            670       680       690       700       710       720

            730       740       750       760       770       780
HCV1    CAGGGCTATAAGGTGCTAGTACTCAACCCCTCTGTTGCTGCAACACTGGGCTTTGGTGCT
        ::::: ::  :::::  ::  ::  ::  :::::  :::::::::::  ::  :  :::  ::  :::::
AY6510  CAGGGGTACAAGGTACTTGTGCTGAACCCGTCTGTTGCTGCCACCTTAGGGTTCGGTGCT
            730       740       750       760       770       780

            790       800       810       820       830       840
HCV1    TACATGTCCAAGGCTCATGGGATCGATCCTAACATCAGGACCGGGGTGAGAACAATTACC
        ::  :::::  :::::  ::::::::::: :: ::::::::::::::::  :::::  ::  ::  :::
AY6510  TATATGTCAAAGGCCCATGGGATCGACCCAAACATCAGGACCGGCGTGAGGACCATCACC
            790       800       810       820       830       840

            850       860       870       880       890       900
HCV1    ACTGGCAGCCCCATCACGTACTCCACCTACGGCAAGTTCCTTGCCGACGGCGGGTGCTCG
        ::  :::   :::::::::   :::::::::::::::::  ::    :  ::  ::  :::::  :::  :
AY6510  ACAGGCTCCCCCATCACCTACTCCACCTACGGCAAATTTTTGGCTGATGGCGGATGCCCA
            850       860       870       880       890       900

            910       920       930       940       950       960
HCV1    GGGGGCGCTTATGACATAATAATTTGTGACGAGTGCCACTCCACGGATGCCACATCCATC
        ::  ::  ::  ::     :::::  ::  :::::   :::::   :::   :::::  ::  :::::
AY6510  GGAGGTGCGTACGACATCATAATATGTGACGAATGTCACTCAGTGGACGCCACCTCGATT
            910       920       930       940       950       960

            970       980       990      1000      1010      1020
HCV1    TTGGGCATCGGCACTGTCCTTGACCAAGCAGAGACTGCGGGGGCGAGACTGGTTGTGCTC
        ::::::::  ::  ::  :::  :  :::::::::  :::::  :::::::::  ::  ::   :::  :::
AY6510  CTGGGCATAGGGACCGTCTTGGACCAAGCGGAGACGGCGGGGGTCAGGCTCACTGTCCTC
            970       980       990      1000      1010      1020

           1030      1040      1050      1060      1070      1080
HCV1    GCCACCGCCACCCCTCCGGGCTCCGTCACTGTGCCCCATCCCAACATCGAGGAGGTTGCT
        ::::::::  ::  ::  ::  ::  :::::::::   :::::  :::  :::::::::::::::  :::::
AY6510  GCCACCGCTACACCACCTGGTTCCGTCACCGTGCCACATTCCAACATCGAGGAAGTTGCA
           1030      1040      1050      1060      1070      1080

           1090      1100      1110      1120      1130
HCV1    CTGTCCACCACCGGAGAGATCCCTTTTTACGGCAAGGCTATCCCCCTCGAAGTA-ATCAA
        ::::::  :    :::  ::  ::  ::  :::::  ::  :::::  ::::::::   ::  ::  :::::
AY6510  CTGTCCGCTGACGGGGAAATACCATTTTATGGTAAGGCCATCCCCCTA-AACTACATCAA
           1090      1100      1110      1120      1130

           1140      1150      1160      1170      1180      1190
HCV1    GGGGGGGAGACATCTCATCTTCTGTCATTCAAAGAAGAAGTGCGACGAACTCGCCGCAAA
        ::::::::::  ::  :::::  :::::  ::  ::  ::::::::::  :::::  :::::  :::::
AY6510  GGGGGGGAGGCACCTCATTTTCTGCCACTCCAAGAAGAAGTGCGACGAGCTCGCTGCAAA
           1140      1150      1160      1170      1180      1190
```

Fig. 16 continued

```
               1200      1210      1220      1230      1240      1250
HCV1    GCTGGTCGCATTGGGCATCAATGCCGTGGCCTACTACCGCGGTCTTGACGTGTCCGTCAT
        ::::::::   ::::  ::::  ::  ::::::::   :::::  ::  ::  :::::  :: :::::
AY6510  GCTGGTCGGTCCGGGCGTCAACGCGGTGGCCTTTTACCGTGGCCTCGACGTATCTGTCAT
               1200      1210      1220      1230      1240      1250

               1260      1270      1280      1290      1300      1310
HCV1    CCCGACCAGCGGCGATGTTGTCGTCGTGGCAACCGATGCCCTCATGACCGGCTATACCGG
        ::  ::   :   ::  ::  ::  ::  ::  ::  ::  :::::  :::  :  :::::  ::::   :::::
AY6510  TCCAACTACAGGAGACGTCGTTGTTGTAGCGACCGACGCCTTGATGACTGGCTTCACCGG
               1260      1270      1280      1290      1300      1310

               1320      1330      1340      1350      1360      1370
HCV1    CGACTTCGACTCGGTGATAGACTGCAATACGTGTGTCACCCAGACAGTCGATTTCAGCCT
        ::  ::::::::   :::::::::::::::  ::  ::::::   :::::::::::::   :::::::::
AY6510  AGATTTCGACTCTGTGATAGACTGCAACACCTGTGTCGTCCAGACAGTCGACTTCAGCCT
               1320      1330      1340      1350      1360      1370

               1380      1390      1400      1410      1420      1430
HCV1    TGACCCTACCTTCACCATTGAGACAATCACGCTCCCCCAGGATGCTGTCTCCCGCACTCA
        :::::::   :::  :  :::::::::   :::  :   :::::::::  ::  :: ::::::  :  ::
AY6510  AGACCCTATATTCTCTATTGAGACTTCCACCGTGCCCCAGGACGCCGTGTCCCGCTCCCA
               1380      1390      1400      1410      1420      1430

               1440      1450      1460      1470      1480      1490
HCV1    ACGTCGGGGCAGGACTGGCAGGGGGAAGCCAGGCATCTACAGATTTGTGGCACCGGGGGA
        :::   ::::   :::::   :   ::::::::   ::  ::   :::::::   :::::   :::::
AY6510  ACGGAGGGGTAGGACCGGTCGAGGGAAGCATGGTATTTACAGATATGTGTCACCCGGGGA
               1440      1450      1460      1470      1480      1490

               1500      1510      1520      1530      1540      1550
HCV1    GCGCCCCTCCGGCATGTTCGACTCGTCCGTCCTCTGTGAGTGCTATGACGCAGGCTGTGC
        :::  ::  ::  :::::::::::::        ::::::::::::::::::::::::  ::  :::::
AY6510  GCGGCCGTCTGGCATGTTCGACTCCGTGGTCCTCTGTGAGTGCTATGACGCGGGTTGTGC
               1500      1510      1520      1530      1540      1550

               1560      1570      1580      1590      1600      1610
HCV1    TTGGTATGAGCTCACGCCCGCCGAGACTACAGTTAGGCTACGAGCGTACATGAACACCCC
        ::::::  :::::  ::  :::::::::  ::::::  :::::  ::::::::  :::  ::  :::::::::
AY6510  TTGGTACGAGCTTACACCCGCCGAGACCACAGTCAGGCTACGGGCATACCTCAACACCCC
               1560      1570      1580      1590      1600      1610

               1620      1630      1640      1650      1660      1670
HCV1    GGGGCTTCCCGTGTGCCAGGACCATCTTGAATTTTGGGAGGGCGTCTTTACAGGCCTCAC
        ::   :   :::::::::::::::::::  :  ::  ::  :::::  :  :::::  ::  ::::::::
AY6510  AGGATTGCCCGTGTGCCAGGACCACTTGGAGTTCTGGGAGAGTGTCTTCACCGGCCTCAC
               1620      1630      1640      1650      1660      1670

               1680      1690      1700      1710      1720      1730
HCV1    TCATATAGATGCCCACTTTCTATCCCAGACAAAGCAGAGTGGGGAGAACCTTCCTTACCT
        ::  :::::::::::::::::  :::::::::  ::  ::::::::::::   ::  :::::
AY6510  CCACATAGATGCCCACTTCCTGTCCCAGACGAAACAGAGTGGGGAGAACTTCCCCTACCT
               1680      1690      1700      1710      1720      1730

               1740      1750      1760      1770      1780      1790
HCV1    GGTAGCGTACCAAGCCACCGTGTGCGCTAGGGCTCAAGCCCCTCCCCCATCGTGGGACCA
```

Fig. 16 continued

```
        ::  ::  :::::::::::::::::::::::  :::    :::  ::::::::  ::  ::::::::
AY6510  AGTCGCATACCAAGCCACCGTGTGCGCTAGAGCTAGAGCTCCTCCCCCGTCATGGGACCA
        1740      1750      1760      1770      1780      1790

            1800      1810      1820      1830      1840      1850
HCV1    GATGTGGAAGTGTTTGATTCGCCTCAAGCCCACCCTCCATGGGCCAACACCCCTGCTATA
        :::::::::::  ::::  ::  :::::::::::::::::  ::::  :  ::  ::  :  :::::
AY6510  AATGTGGAAGTGCCTGATACGGCTCAAGCCCACCCTCACTGGGGCTACCCCATTACTATA
        1800      1810      1820      1830      1840      1850

            1860      1870      1880      1890      1900      1910
HCV1    CAGACTGGGCGCTGTTCAGAATGAAATCACCCTGACGCACCCAGTCACCAAATACATCAT
        :::::::::        :::  ::::::::  :::::::  :  ::  :::::  :::::  ::::::::::
AY6510  CAGACTGGGTAGTGTACAGAATGAGATCACCTTAACACACCCAATCACCCAATACATCAT
        1860      1870      1880      1890      1900      1910

            1920      1930      1940      1950
HCV1    GACATGCATGTCGGCCGACCTGGAGGTCGTCAC
        :  :  :::::::::::  :::::::::::::::::
AY6510  GGCTTGCATGTCGGCGGACCTGGAGGTCGTCAC
        1920      1930      1940      1950
```

Fig: 17

```
            10        20        30        40        50        60
HCV1    AGCACCTGGGTGCTCGTTGGCGGCGTCCTGGCTGCTTTGGCCGCGTATTGCCTGTCAACA
        :::::  :::::::  :  ::  :::::::::::  ::  ::::::::::::  ::  ::::::::  :::
AY6510  AGCACGTGGGTGTTGGTGGGCGGCGTCCTAGCCGCTTTGGCCGCTTACTGCCTGTCCACA
            10        20        30        40        50        60

            70       ·80        90        100       110       120
HCV1    GGCTGCGTGGTCATAGTGGGCAGGGTCGTCTTGTCCGGGAAGCCGGCAATCATACCTGAC
        :::  :::::::::::::::::::::::::  :  ::  :          :::::::::::::  :::::::::::
AY6510  GGCAGCGTGGTCATAGTGGGCAGGATAATCCTAGGTGGGAAGCCGGCAGTCATACCTGAC
            70        80        90        100       110       120

            130       140       150       160       170       180
HCV1    AGGGAAGTCCTCTACCGAGAGTTCGATGAGATGGAAGAGTGCTCTCAGCACTTACCGTAC
        :::::  ::  :::::::::::::::  :::::::::::::  :::::::  :  :::  ::  :::  :::
AY6510  AGGGAGGTTCTCTACCGAGAGTTTGATGAGATGGAGGAGTGCGCCGCCCACGTCCCCTAC
            130       140       150       160       170       180

            190       200       210       220       230       240
HCV1    ATCGAGCAAGGGATGATGCTCGCCGAGCAGTTCAAGCAGAAGGCCCTCGGCCTCCTGCAG
        :::::::  ::::::          :  ::  :::::::::::::::::  ::  ::  :  :  :::
AY6510  CTCGAGCAGGGGATGCATTTGGCGGAGCAGTTCAAGCAGAAAGCTCTTGGGTTGCTCCAG
            190       200       210       220       230       240

            250       260       270       280       290       300
HCV1    ACCGCGTCCCGTCAGGCAGAGGTTATCGCCCCTGCTGTCCAGACCAACTGGCAAAAACTC
        ::  ::  :::      ::      :::::        :::  :  ::        :::::::  :  ::  :::::  ::  :::
AY6510  ACGGCATCCAAACAAACAGAGACGATCACTCCCATTGTCCAGTCTAATTGGCAGAAGCTC
            250       260       270       280       290       300
```

Fig. 17 continued

```
               310       320       330       340       350       360
HCV1    GAGACCTTCTGGGCGAAGCATATGTGGAACTTCATCAGTGGGATACAATACTTGGCGGGC
        ::: : ::::::::: :: :: ::::::::::::: : :: :::::::::::  ::::::::
AY6510  GAGTCTTTCTGGGCTAAACACATGTGGAACTTCGTTAGCGGGATACAATATCTGGCGGGC
               310       320       330       340       350       360

               370       380       390       400       410       420
HCV1    TTGTCAACGCTGCCTGGTAACCCCGCCATTGCTTCATTGATGGCTTTTACAGCTGCTGTC
         : ::::::::::: :: ::::::::: :: :: ::  ::::: : ::::: :: :: :: 
AY6510  CTATCAACGCTGCCCGGGAACCCCGCTATAGCATCGCTGATGTCGTTTACGGCCGCAGTG
               370       380       390       400       410       420

               430       440       450       460       470       480
HCV1    ACCAGCCCACTAACCACTAGCCAAACCCTCCTCTTCAACATATTGGGGGGGTGGGTGGCT
        :: :: ::::::::::::   :: :::::::::::: ::::: :::::::::::: :::::
AY6510  ACGAGTCCACTAACCACTCAGCAGACCCTCCTCTTTAACATCTTGGGGGGGTGGCTGGCT
               430       440       450       460       470       480

               490       500       510       520       530       540
HCV1    GCCCAGCTCGCCGCCCCCGGTGCCGCTACTGCCTTTGTGGGCGCTGGCTTAGCTGGCGCC
        :::::::: :::::::: :  ::::: :: ::::: :: ::::: ::: :  ::::::::
AY6510  GCCCAGCTTGCCGCCCCAGCCGCCGCCACAGCCTTCGTTGGCGCAGGCATTACTGGCGCC
               490       500       510       520       530       540

               550       560       570       580       590       600
HCV1    GCCATCGGCAGTGTTGGACTGGGGAAGGTCCTCATAGACATCCTTGCAGGGTATGGCGCG
        :   : :::::::: :: :: :::::::::::  : ::::: ::::: :: :: :: :: 
AY6510  GTTGTTGGCAGTGTGGGCCTAGGGAAGGTCCTGGTGGACATTCTTGCCGGCTACGGGGCT
               550       560       570       580       590       600

               610       620       630       640       650       660
HCV1    GGCGTGGCGGGAGCTCTTGTGGCATTCAAGATCATGAGCGGTGAGGTCCCCTCCACGGAG
        :: ::::: :: :: :: ::::: ::::: ::::::::::: :::  :::: ::::::::
AY6510  GGTGTGGCCGGGGCCCTCGTGGCTTTCAAAATCATGAGCGGGGAGACCCCCACCACGGAG
               610       620       630       640       650       660

               670       680       690       700       710       720
HCV1    GACCTGGTCAATCTACTGCCCGCCATCCTCTCGCCCGGAGCCCTCGTAGTCGGCGTGGTC
        :: :: ::::: :: ::::: :::::::: ::::: ::::: ::::: :::: :::::: 
AY6510  GATCTAGTCAACCTTCTGCCTGCCATCCTATCGCCAGGAGCTCTCGTTGTCGCCGTGGTG
               670       680       690       700       710       720

               730       740       750       760       770       780
HCV1    TGTGCAGCAATACTGCGCCGGCACGTTGGCCCGGGCGAGGGGGCAGTGCAGTGGATGAAC
        :: ::::::::::: ::::::::::: ::::  :::::::: :: :::::::::::::::
AY6510  TGCGCAGCAATACTACGCCGGCACGTGGGCCTTGGCGAGGGCGCCGTGCAGTGGATGAAC
               730       740       750       760       770       780

               790       800       810       820       830       840
HCV1    CGGCTGATAGCCTTCGCCTCCCGGGGGAACCATGTTTCCCCCACGCACTACGTGCCGGAG
        ::::::::::: :: :: :: ::::: ::::: :: ::::: :: :::::::::::::::
AY6510  CGGCTGATAGCGTTTGCTTCTCGGGGTAACCACGTCTCCCCTACACACTACGTGCCGGAG
               790       800       810       820       830       840

               850       860       870       880       890       900
HCV1    AGCGATGCAGCTGCCCGCGTCACTGCCATACTCAGCAGCCTCACTGTAACCCAGCTCCTG
        ::::: ::  : :: :: :::::  : :: :::: ::: :::::::: :: ::::: :::
```

Fig. 17 continued

```
AY6510  AGCGACGCGTCGGCTCGTGTCACACCAATTCTCACCAGGCTCACTGTTACTCAGCTTCTG
               850       860       870       880       890       900

               910       920       930       940
HCV1    AGGCGACTGCACCAGTGGATAAGCTCGGAGTGTACCACTCCATG
        :   : :: :::  ::::::::::::: : :: : : : :: ::
AY6510  AAAGGGCTCCACGTGTGGATAAGCTCGAATTGCATCGCCCCGTG
               910       920       930       940
```

FIG: 18

```
                10        20        30        40        50        60
HCV1    GTTCCTGGCTAAGGGACATCTGGGACTGGATATGCGAGGTGTTGAGCGACTTTAAGACCT
        :::: ::::: :  ::  ::::: ::::::::::::::::: :::::::::: ::::  :
AY6510  GTTCTTGGCTTAAAGATGTCTGGAACTGGATATGCGAGGTGCTGAGCGACTTCAAGAATT
                10        20        30        40        50        60

                70        80        90       100       110       120
HCV1    GGCTAAAAGCTAAGCTCATGCCACAGCTGCCTGGGATCCCCTTTGTGTCCTGCCAGCGCG
        :::: :: :: :: ::  : ::::: ::::: :::::::: :: :: :::::::: ::::
AY6510  GGCTGAAGGCCAAACTTGTACCACAACTGCCCGGGATCCCATTCGTATCCTGCCAACGCG
                70        80        90       100       110       120

               130       140       150       160       170       180
HCV1    GGTATAAGGGGGTCTGGCGAGTGGACGGCATCATGCACACTCGCTGCCACTGTGGAGCTG
        ::::    ::::::::::: :  :: :::::: :::::::::: ::::  ::::: ::  
AY6510  GGTACCGTGGGGTCTGGCGGGGCGAGGGCATCGTGCACACTCGTTGCCCGTGTGGGGCCA
               130       140       150       160       170       180

               190       200       210       220       230       240
HCV1    AGATCACTGGACATGTCAAAAACGGGACGATGAGGATCGTCGGTCCTAGGACCTGCAGGA
        : :: :::::::::::::: :::::  ::::::: :::::::: :::: ::: ::::: :
AY6510  ATATAACTGGACATGTCAAGAACGGTTCGATGAGAATCGTCGGGCCTAAGACTTGCAGCA
               190       200       210       220       230       240

               250       260       270       280       290       300
HCV1    ACATGTGGAGTGGGACCTTCCCCATTAATGCCTACACCACGGGCCCCTGTACCCCCCTTC
        :::  ::: ::::: : ::::::::::: :: ::::: :: ::::: :: :: :::   :
AY6510  ACACCTGGCGTGGGTCGTTCCCCATTAACGCTTACACTACAGGCCCGTGCACGCCCTCCC
               250       260       270       280       290       300

               310       320       330       340       350       360
HCV1    CTGCGCCGAACTACACGTTCGCGCTATGGAGGGTGTCTGCAGAGGAATATGTGGAGATAA
        : ::::::::::: :::::::::::::::::::::::::::::::: ::::::::: :::
AY6510  CGGCGCCGAACTATACGTTCGCGCTATGGAGGGTGTCTGCAGAGGAGTATGTGGAGGTAA
               310       320       330       340       350       360

               370       380       390       400       410       420
HCV1    GGCAGGTGGGGGACTTCCACTACGTGACGGGTATGACTACTGACAATCTCAAATGCCCGT
        ::: : ::::::::::::: ::::: :::::  ::: :::::: :: ::::: :: :: :
AY6510  GGCGGCTGGGGGACTTCCATTACGTCACGGGGGTGACCACTGATAAACTCAAGTGTCCAT
               370       380       390       400       410       420

               430       440       450       460       470       480
```

```
HCV1    GCCAGGTCCCATCGCCCGAATTTTTCACAGAATTGGACGGGGTGCGCCTACATAGGTTTG
        :::::::::: :: ::::: :: : ::::::  :::::::::::::::: :::::::  :
AY6510  GCCAGGTCCCCTCACCCGAGTTCTCCACAGAGGTGGACGGGGTGCGCCTGCATAGGTACG
               430       440       450       460       470       480

               490       500       510       520       530       540
HCV1    CGCCCCCCTGCAAGCCCTTGCTGCGGGAGGAGGTATCATTCAGAGTAGGACTCCACGAAT
        : :: :::::::: ::: :::: ::::: :::::  : :: :: :: ::  :: : ::::
AY6510  CCCCTCCCTGCAAACCCCTGCTACGGGATGAGGTGACGTTTAGCGTCGGGTTCAATGAAT
               490       500       510       520       530       540

               550       560       570       580       590       600
HCV1    ACCCGGTAGGGTCGCAATTACCTTGCGAGCCCGAACCGGACGTGGCCGTGTTGACGTCCA
        ::: ::: ::::: :: :: :: ::::::::::: :: ::::: :: :  :: :: :: :
AY6510  ACCTGGTGGGGTCCCAGTTGCCCTGCGAGCCCGAGCCAGACGTAGCAGCATTAACATCAA
               550       560       570       580       590       600

               610       620       630       640       650       660
HCV1    TGCTCACTGATCCCTCCCATATAACAGCAGAGGCGGCCGGGCGAAGGTTGGCGAGGGGAT
        :::: :: :: :: ::::: :: :: ::: :: :::: : ::: ::: ::  : :::: :
AY6510  TGCTTACAGACCCTTCCCACATCACTGCAAAGACGGCGGCGCGTAGGCTGAAGCGGGGGT
               610       620       630       640       650       660

               670       680       690       700       710       720
HCV1    CACCCCCCTCTGTGGCCAGCTCCTCGGCTAGCCAGCTATCCGCTCCATCTCTCAAGGCAA
        : ::::::::  ::::::: :: :: :: :::::::: ::::: :: :: :: :: ::::
AY6510  CTCCCCCCTCCCTGGCCAGTTCTTCTGCCAGCCAGCTGTCCGCGCCGTCACTGAAAGCAA
               670       680       690       700       710       720

               730       740       750       760       770       780
HCV1    CTTGCACCGCTAACCATGACTCCCCTGATGCTGAGCTCATAGAGGCCAACCTCCTATGGA
        : :::::: :: :::::::::: :: :: :: :: :::::::: ::::::::::: ::::
AY6510  CATGCACCACTCACCATGACTCTCCAGACGCCGACCTCATAGAAGCCAACCTCCTGTGGA
               730       740       750       760       770       780

               790       800       810       820       830       840
HCV1    GGCAGGAGATGGGCGGCAACATCACCAGGGTTGAGTCAGAAAACAAAGTGGTGATTCTGG
        : : ::::::::: :: ::::::::::: :: ::::: :: :::::  : ::  ::::::
AY6510  GACGGGAGATGGGGGGGAACATCACCAGAGTGGAGTCGGAGAACAAGATTGTTGTTCTGG
               790       800       810       820       830       840

               850       860       870       880       890       900
HCV1    ACTCCTTCGATCCGCTTGTGGCGGAGGAGGACGAGCGGGAGATCTCCGTACCCGCAGAAA
        : :: ::::: ::::: ::::: :::::::: :: :::::::: ::  : :: :: :: :
AY6510  ATTCTTTCGACCCGCTCGTGGCAGAGGAGGATGACCGGGAGATTTCTATTCCAGCTGAGA
               850       860       870       880       890       900

               910       920       930       940       950       960
HCV1    TCCTGCGGAAGTCTCGG-AGATTCGCCCAGGCCCTGCCCGTTTGGGCGCGGCCGGACTAT
        : :::::::: : :  : :: ::: ::: : :: ::::: : ::::: :::::::: :::
AY6510  TTCTGCGGAAATTTAAGCAGTTTCCCCCCG-CCATGCCCATATGGGCACGGCCGGATTAT
               910       920       930       940       950       960

               970       980       990      1000      1010      1020
HCV1    AACCCCCCGCTAGTGGAGACGTGGAAAAAGCCCGACTACGAACCACCTGTGGTCCATGGC
        :: :: :: :: :::::  :::::::    :: ::::  :: :::::  : ::::: :: 
AY6510  AATCCTCCCCTTGTGGAACCGTGGAAGCGCCCGGACTGTGATCCACCCTTAGTCCACGGG
```

Figure 18:
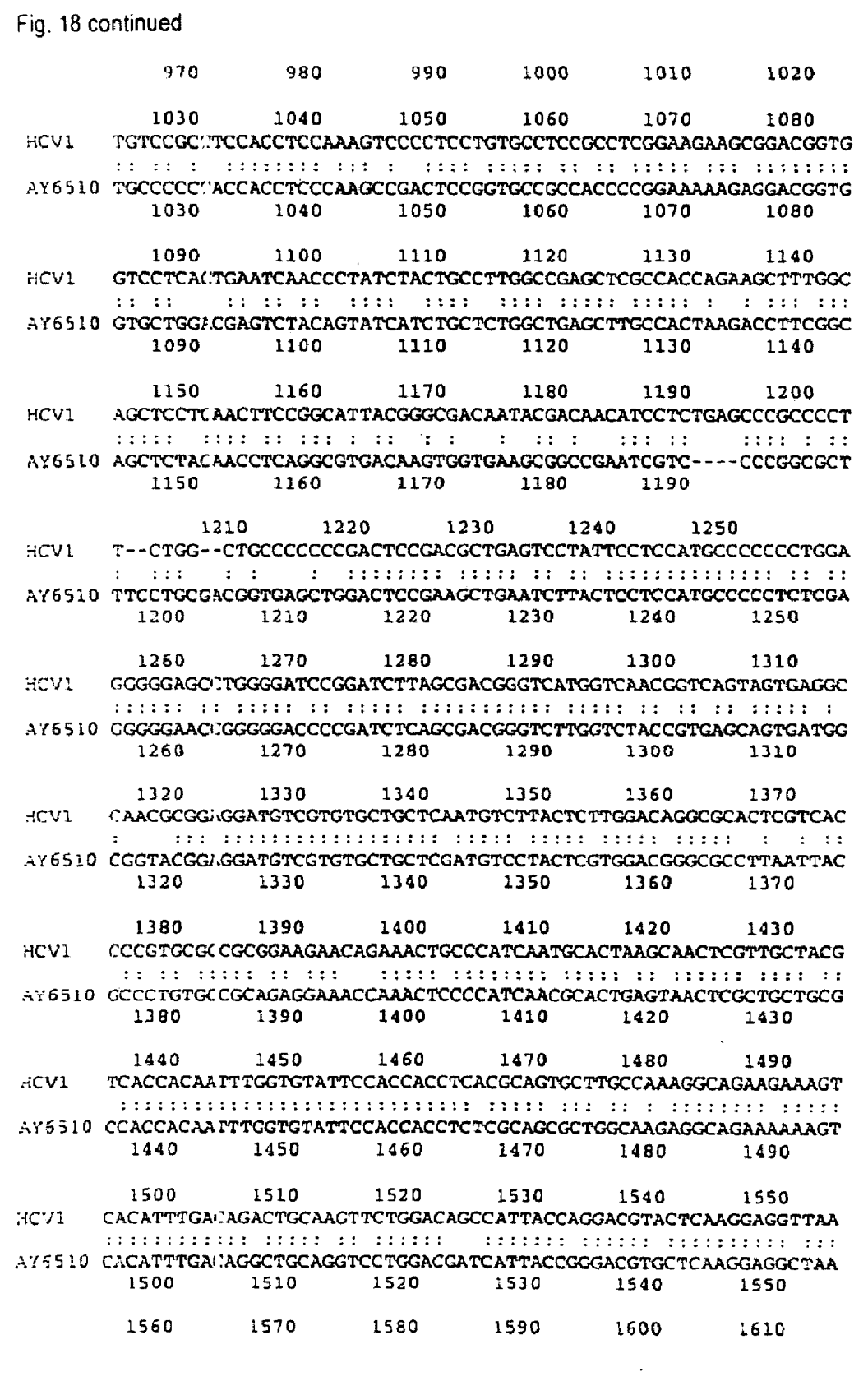

```
              970       980       990      1000      1010      1020

             1030      1040      1050      1060      1070      1080
HCV1    TGTCCGCCTCCACCTCCAAAGTCCCCTCCTGTGCCTCCGCCTCGGAAGAAGCGGACGGTG
        :: :: :  :::::::: ::: :  :::: ::::: :: :: ::::: ::: ::::::::
AY6510  TGCCCCCTACCACCTCCCAAGCCGACTCCGGTGCCGCCACCCCGGAAAAAGAGGACGGTG
             1030      1040      1050      1060      1070      1080

             1090      1100      1110      1120      1130      1140
HCV1    GTCCTCACTGAATCAACCCTATCTACTGCCTTGGCCGAGCTCGCCACCAGAAGCTTTGGC
        :: ::     :: :: ::  ::::  ::::  :::: ::::: ::::: :  : ::: :::
AY6510  GTGCTGGACGAGTCTACAGTATCATCTGCTCTGGCTGAGCTTGCCACTAAGACCTTCGGC
             1090      1100      1110      1120      1130      1140

             1150      1160      1170      1180      1190      1200
HCV1    AGCTCCTCAACTTCCGGCATTACGGGCGACAATACGACAACATCCTCTGAGCCCGCCCCT
        :::::  :::: :: ::: : ::  : :     :  :: :    ::: ::    :::: : ::
AY6510  AGCTCTACAACCTCAGGCGTGACAAGTGGTGAAGCGGCCGAATCGTC----CCCGGCGCT
             1150      1160      1170      1180      1190

                 1210      1220      1230      1240      1250
HCV1    T--CTGG--CTGCCCCCCCGACTCCGACGCTGAGTCCTATTCCTCCATGCCCCCCCTGGA
        :  :::    : :     :  :::::::: ::::: :: :: ::::::::::::: :: ::
AY6510  TTCCTGCGACGGTGAGCTGGACTCCGAAGCTGAATCTTACTCCTCCATGCCCCCTCTCGA
           1200      1210      1220      1230      1240      1250

           1260      1270      1280      1290      1300      1310
HCV1    GGGGAGCCTGGGGATCCGGATCTTAGCGACGGGTCATGGTCAACGGTCAGTAGTGAGGC
        :::::: :: ::::: :: ::::: ::::::::::: ::::: :: :: :: ::::: :
AY6510  GGGGAACCGGGGGACCCCGATCTCAGCGACGGGTCTTGGTCTACCGTGAGCAGTGATGG
           1260      1270      1280      1290      1300      1310

           1320      1330      1340      1350      1360      1370
HCV1    CAACGCGGAGGATGTCGTGTGCTGCTCAATGTCTTACTCTTGGACAGGCGCACTCGTCAC
        :     ::: ::::::::::::::::::: ::::: ::::: ::::: :::::  :  : ::
AY6510  CGGTACGGAGGATGTCGTGTGCTGCTCGATGTCCTACTCGTGGACGGGCGCCTTAATTAC
           1320      1330      1340      1350      1360      1370

           1380      1390      1400      1410      1420      1430
HCV1    CCCGTGCGCCGCGGAAGAACAGAAACTGCCCATCAATGCACTAAGCAACTCGTTGCTACG
         :: :: ::::: :: :::    ::::: :::::::: ::::: :: :::::: :::: ::
AY6510  GCCCTGTGCCGCAGAGGAAACCAAACTCCCCATCAACGCACTGAGTAACTCGCTGCTGCG
           1380      1390      1400      1410      1420      1430

           1440      1450      1460      1470      1480      1490
HCV1    TCACCACAATTTGGTGTATTCCACCACCTCACGCAGTGCTTGCCAAAGGCAGAAGAAAGT
         :::::::::::::::::::::::::::: ::::: ::: :: : :::::::: :::::
AY6510  CCACCACAATTTGGTGTATTCCACCACCTCTCGCAGCGCTGGCAAGAGGCAGAAAAAAGT
           1440      1450      1460      1470      1480      1490

           1500      1510      1520      1530      1540      1550
HCV1    CACATTTGACAGACTGCAAGTTCTGGACAGCCATTACCAGGACGTACTCAAGGAGGTTAA
        :::::::::::: ::::: :: ::::::    ::::::: :::::: :::::::::: :::
AY6510  CACATTTGACAGGCTGCAGGTCCTGGACGATCATTACCGGGACGTGCTCAAGGAGGCTAA
           1500      1510      1520      1530      1540      1550

           1560      1570      1580      1590      1600      1610
```

```
HCV1    AGCAGCGGCGTCAAAAGTGAAGGCTAACTTGCTATCCGTAGAGGAAGCTTGCAGCCTGAC
         ::   ::: :: : :::::::::::: ::::::::::::::::: :: :: ::::::::
AY6510  GGCCAAGGCATCCACAGTGAAGGCTAAATTGCTATCCGTAGAGGAGGCATGTAGCCTGAC
           1560      1570      1580      1590      1600      1610

           1620      1630      1640      1650      1660      1670
HCV1    GCCCCCACACTCAGCCAAATCCAAGTTTGGTTATGGGGCAAAAGACGTCCGTTGCCATGC
        :::::: ::::: :::: ::: :: ::::: :::::: : :: :: :::::  ::::: :
AY6510  GCCCCCGCACTCCGCCAGATCAAAATTTGGCTATGGGCCGAAGGATGTCCGAAGCCATTC
           1620      1630      1640      1650      1660      1670

           1680      1690      1700      1710      1720      1730
HCV1    CAGAAAGGCCGTAACCCACATCAACTCCGTGTGGAAAGACCTTCTGGAAGACAATGTAAC
        ::: :::::  ::  ::::::::::::::::::: : ::::::::::: ::::::  :::
AY6510  CAGTAAGGCTATACGCCACATCAACTCCGTGTGGCAGGACCTTCTGGAGGACAATACAAC
           1680      1690      1700      1710      1720      1730

           1740      1750      1760      1770      1780      1790
HCV1    ACCAATAGACACTACCATCATGGCTAAGAACGAGGTTTTCTGCGTTCAGCCTGAGAAGGG
        ::: :::::::::::::::::::: ::::: :: :: ::::::::  :: : :: :: ::
AY6510  ACCTATAGACACTACCATCATGGCCAAGAATGAAGTCTTCTGCGTGAAGGCCGAAAAAGG
           1740      1750      1760      1770      1780      1790

           1800      1810      1820      1830      1840      1850
HCV1    GGGTCGTAAGCCAGCTCGTCTCATCGTGTTCCCCGATCTGGGCGTGCGCGTGTGCGAAAA
        :::::: ::::: ::::: :: ::::::: :::::: ::::: :::::::::::::: ::
AY6510  GGGTCGCAAGCCCGCTCGCCTTATCGTGTACCCCGACCTGGGGGTGCGCGTGTGCGAGAA
           1800      1810      1820      1830      1840      1850

           1860      1870      1880      1890      1900      1910
HCV1    GATGGCTTTGTACGACGTGGTTACAAAGCTCCCCTTGGCCGTGATGGGAAGCTCCTACGG
        ::  :::::::: ::::: :: : : :::::::: : ::::::::::::  :::::::::
AY6510  GAGAGCTTTGTATGACGTAGTCAAACAGCTCCCCATTGCCGTGATGGGACCCTCCTACGG
           1860      1870      1880      1890      1900      1910

           1920      1930      1940      1950      1960      1970
HCV1    ATTCCAATACTCACCAGGACAGCGGGTTGAATTCCTCGTGCAAGCGTGGAAGTCCAAGAA
         ::::: ::::: ::::  :::::::: :: :::::  :  : :::::::: :: :::::
AY6510  GTTCCAGTACTCGCCAGCGCAGCGGGTCGACTTCCTGCTTAACGCGTGGAAATCAAAGAA
           1920      1930      1940      1950      1960      1970

           1980      1990      2000      2010      2020      2030
HCV1    AACCCCAATGGGGTTCTCGTATGATACCCGCTGCTTTGACTCCACAGTCACTGAGAGCGA
        :: ::: :::::::: :: ::::: ::::: ::::::::::: ::::::::::::   ::
AY6510  AAACCCTATGGGGTTTTCCTATGACACCCGTTGCTTTGACTCAACAGTCACTGAGGCTGA
           1980      1990      2000      2010      2020      2030

           2040      2050      2060      2070      2080      2090
HCV1    CATCCGTACGGAGGAGGCAATCTACCAATGTTGTGACCTCGACCCCCAAGCCCGCGTGGC
         :::::::::::::: :   :::: :::: ::::::::: : :::  : ::::::: :::
AY6510  TATCCGTACGGAGGAAGACCTCTATCAATCTTGTGACCTGGTCCCTGAGGCCCGCGCGGC
           2040      2050      2060      2070      2080      2090

           2100      2110      2120      2130      2140      2150
HCV1    CATCAAGTCCCTCACCGAGAGGCTTTATGTTGGGGGCCCTCTTACCAATTCAAGGGGGGA
        ::: : ::: ::::: :::::::::::  : :::::::: ::::::::::: : :::  :
AY6510  CATAAGGTCTCTCACAGAGAGGCTTTACATCGGGGGCCCACTTACCAATTCTAAGGGACA
```

```
               2100      2110      2120      2130      2140      2150

               2160      2170      2180      2190      2200      2210
HCV1    GAACTGCGGCTATCGCAGGTGCCGCGCGAGCGGCGTACTGACAACTAGCTGTGGTAACAC
         ::::::::::::::  : ::::::: ::::::::: ::::: :::::::: ::::::::
AY6510  AAACTGCGGCTATCGGCGATGCCGCGCAAGCGGCGTGCTGACCACTAGCTGCGGTAACAC
              2160      2170      2180      2190      2200      2210

               2220      2230      2240      2250      2260      2270
HCV1    CCTCACTTGCTACATCAAGGCCCGGGCAGCCTGTCGAGCCGCAGGGCTCCAGGACTGCAC
        : : ::::::::: : :::::  : :: ::::::::::: :::  :::::::::::::::
AY6510  CATAACTTGCTACCTTAAGGCTAGTGCGGCCTGTCGAGCTGCAAAGCTCCAGGACTGCAC
              2220      2230      2240      2250      2260      2270

              2280      2290      2300      2310      2320      2330
HCV1    CATGCTCGTGTGTGGCGACGACTTAGTCGTTATCTGTGAAAGCGCGGGGGTCCAGGAGGA
        :::::::::::: ::::::::: : :::::::::::::::::::: :: ::: :::::::
AY6510  CATGCTCGTGTGCGGCGACGACCTCGTCGTTATCTGTGAAAGCGCCGGTGTCAAGGAGGA
              2280      2290      2300      2310      2320      2330

              2340      2350      2360      2370      2380      2390
HCV1    CGCGGCGAGCCTGAGAGCCTTCACGGAGGCTATGACCAGGTACTCCGCCCCCCCTGGGGA
        ::: :::::::::::::::::::: ::::::::::::::::::::::: ::::::: :: ::
AY6510  CGCTGCGAGCCTGAGAGCCTTCACCGAGGCTATGACCAGGTACTCCGGCCCCCCGGGAGA
              2340      2350      2360      2370      2380      2390

              2400      2410      2420      2430      2440      2450
HCV1    CCCCCCACAACCAGAATACGACTTGGAGCTCATAACATCATGCTCCTCCAACGTGTCAGT
        :::  : ::::::::::::::::::::::: :::::::: ::::::::::: ::::: ::
AY6510  CCCGGCTCAACCAGAATACGACTTGGAGCTTATAACATCCTGCTCCTCCAATGTGTCGGT
              2400      2410      2420      2430      2440      2450

              2460      2470      2480      2490      2500      2510
HCV1    CGCCCACGACGGCGCTGGAAAGAGGGTCTACTACCTCACCCGTGACCCTACAACCCCCCT
        ::: : ::::::::::::  : :::::::: :: :: :::::::: :::   :: :::::
AY6510  CGCGCGCGACGGCGCTGGCCAAAGGGTCTATTATCTGACCCGTGAACCTGAGACTCCCCT
              2460      2470      2480      2490      2500      2510

              2520      2530      2540      2550      2560      2570
HCV1    CGCGAGAGCTGCGTGGGAGACAGCAAGACACACTCCAGTCAATTCCTGGCTAGGCAACAT
        :::: : :: :: ::::::::::::::::::::::::::: :: ::::::::::::::::
AY6510  CGCGCGTGCCGCTTGGGAGACAGCAAGACACACTCCAGTGAACTCCTGGCTAGGCAACAT
              2520      2530      2540      2550      2560      2570

              2580      2590      2600      2610      2620      2630
HCV1    AATCATGTTTGCCCCCACACTGTGGGCGAGGATGATACTGATGACCCATTTCTTTAGCGT
         :::::::::::::::::: ::::::   ::::: : :: :::::::: : : ::   : :
AY6510  CATCATGTTTGCCCCCACTCTGTGGGTACGGATGGTCCTCATGACCCACTTATTCTCCAT
              2580      2590      2600      2610      2620      2630

              2640      2650      2660      2670      2680      2690
HCV1    CCTTATAGCCAGGGACCAGCTTGAACAGGCCCTCGATTGCGAGATCTACGGGGCCTGCTA
         :: ::::    ::: :: ::::: :::: :: ::::: :: ::::: : : :::    :
AY6510  ACTCATAGTTCAGGAGCACCTTGAAAAGGCTCTAGATTGTGAAATCTATGGAGCCACACA
              2640      2650      2660      2670      2680      2690

              2700      2710      2720      2730      2740      2750
```

```
HCV1   CTCCATAGAACCACTTGATCTACCTCCAATCATTCAAAGACTCCATGGCCTCAGCGCATT
       :::: :   :::  : :: ::::::  :::::::::::::::::::::::::::::: ::
AY6510 CTCCGTCCCACCGTTGGACCTACCTGAAATCATTCAAAGACTCCATGGCCTCAGCGCGTT
        2700      2710      2720      2730      2740      2750

        2760      2770      2780      2790      2800      2810
HCV1   TTCACTCCACAGTTACTCTCCAGGTGAAATTAATAGGGTGGCCGCATGCCTCAGAAAACT
       ::: ::::::::::::::::::::::::::: :::::::::::  :::::::::: :::::
AY6510 TTCGCTCCACAGTTACTCTCCAGGTGAAATCAATAGGGTGGCTTCATGCCTCAGGAAACT
        2760      2770      2780      2790      2800      2810

        2820      2830      2840      2850      2860      2870
HCV1   TGGGGTACCGCCCTTGCGAGCTTGGAGACACCGGGCCCGGAGCGTCCGCGCTAGGCTTCT
       :::::: :: :::::::::::::::::::::::::::::::::::::::: :  :: ::
AY6510 TGGGGTTCCACCCTTGCGAGCTTGGAGACACCGGGCCCGGAGCGTCCGCGCCACACTCCT
        2820      2830      2840      2850      2860      2870

        2880      2890      2900      2910      2920      2930
HCV1   GGCCAGAGGAGGCAGGGCTGCCATATGTGGCAAGTACCTCTTCAACTGGGCAGTAAGAAC
         ::   :: :: :   :: :::::::: :: ::::::::::::::::::: :: : :::
AY6510 ATCCCAGGGGGGGAAAGCCGCCATATGCGGTAAGTACCTCTTCAACTGGGCGGTGAAAAC
        2880      2890      2900      2910      2920      2930

        2940      2950      2960      2970      2980      2990
HCV1   AAAGCTCAAACTCACTCCAATAGCGGCCGCTGGCCAGCTGGACTTGTCCGGCTGGTTCAC
        :: :::::::::: :::: :: ::  :::     ::  :::::::::::   ::::::::
AY6510 CAAACTCAAACTCATTCCATTACCGCTCGCGTCTCATTTGGACTTGTCCAATTGGTTCAC
        2940      2950      2960      2970      2980      2990

        3000      3010      3020      3030      3040      3050
HCV1   GGCTGGCTACAGCGGGGGAGACATTTATCACAGCGTGTCTCATGCCCGGCCCCGCTGGAT
       ::  :::::::::::::::::::::::::::::::::::::::::::::::::: ::: :
AY6510 GGGCGGCTACAGCGGGGGAGACATTTATCACAGCGTGTCTCATGCCCGGCCCCGTTGGTT
        3000      3010      3020      3030      3040      3050

        3060      3070      3080      3090      3100      3110
HCV1   CTGGTTTTGCCTACTCCTGCTTGCTGCAGGGGTAGGCATCTACCTCCTCCCCAACCGA
           :   ::::::::::: ::   : : :::::::::::::::::::: :::::::::
AY6510 TCTCTGGTGCCTACTCCTACTCTCAGTAGGGGTAGGCATCTACCTCCTTCCCAACCGA
        3060      3070      3080      3090      3100      3110
```

Fig: 19

```
                 10        20
HCV1   GAAGGTTGGGGTAAACACTCC-GGCCT
       :: :::::::  :: :::::: :::::
AY6510 GACGGTTGGGC-AACCACTCCAGGCCT
                10        20
```

Fig 20

```
                  10        20        30        40        50        60
HCV1   MSTNPKPQKKNKRNTNRRPQDVKFPGGGQIVGGVYLLPRRGPRLGVRATRKTSERSQPRG
       ::::::::.:.:::::::::::::::::::::::::::::::::::::::::::::::::
Ay6510 MSTNPKPQRKTKRNTNRRPQDVKFPGGGQIVGGVYLLPRRGPRLGVRATRKTSERSQPRG
```

```
                 10        20        30        40        50        60

                 70        80        90       100       110       120
HCV1     RRQPIPKARRPEGRTWAQPGYPWPLYGNEGCGWAGWLLSPRGSRPSWGPTDPRRRSRNLG
         ::::::::::::::::::::::::::::::::::::::::::::::::::::::::::::
Ay6510   RRQPIPKARRPEGRTWAQPGYPWPLYGNEGCGWAGWLLSPRGSRPSWGPTDPRRRSRNLG
                 70        80        90       100       110       120

                130       140       150       160       170       180
HCV1     KVIDTLTCGFADLMGYIPLVGAPLGGAARALAHGVRVLEDGVNYATGNLPGCSFSIFLLA
         ::::::: ::::::::::::::::::::::::::::::::::::::::::::::::::::
Ay6510   KVIDTLTYGFADLMGYIPLVGAPLGGAARALAHGVRVLEDGVNYATGNLPGCSFSIFLLA
                130       140       150       160       170       180

                190
HCV1     LLSCLTVPASA
         :::::::::::
Ay6510   LLSCLTVPASA
                190
```

Fig 21

```
                 10        20        30        40        50        60
HCV1     VRNSTGLYHVTNDCPNSSIVYEAADAILHTPGCVPCVREGNASRCWVAMTPTVATRDGKL
         ::::.:.:::::::::.:.:::.   :.: :::::::::::.:::::...:::::..:  .
Ay6510   VRNSSGVYHVTNDCPNASVVYETDSLIIHLPGCVPCVREGNGSRCWVSLSPTVAAKDPGV
                 10        20        30        40        50        60

                 70        80        90       100       110       120
HCV1     PATQLRRHIDLLVGSATLCSALYVGDLCGSVFLVGQLFTFSPRRHWTTQGCNCSIYPGHI
         :....:::.::..:.:..:::.::: ::::.::::::::.::::::::: :::::::::.
Ay6510   PVNEIRRHVDLIAGAAAFCSAMYVGHLCGSIFLVGQLFTLSPRRHWTTQDCNCSIYPGHV
                 70        80        90       100       110       120

                130       140       150       160       170       180
HCV1     TGHRMAWDMMMNWSPTTALVMAQLLRIPQAILDMIAGAHWGVLAGIAYFSMVGNWAKVLV
         ::::::::::::::::::::.::::::::::::::::::::::::::::::::::.::::
Ay6510   TGHRMAWDMMMNWSPTTALVVAQLLRIPQAILDMIAGAHWGVLAGIAYFSMVGNWTKVLV
                130       140       150       160       170       180

                190
HCV1     VLLLPAGVDA
         ::::::::::
Ay6510   VLLLPAGVDA
                190
```

Fig 22

```
                 10        20        30        40        50        60
E2       THVTGGSAGHTVSGFVSLLAPGAKQNVQLINTNGSWHLNSTALNCNDSLNTGWLAGLFYH
         : :.:::::...:.:.:..:::.::.:::::::::::.: :::::::.:.:::.:::::
Ay6510   TIVSGGSAGRSTAGLVGLFSPGARQNIQLINTNGSWHINRTALNCNDTLQTGWVAGLFYT
                 10        20        30        40        50        60
```

Fig. 22 continued

```
               70        80        90       100       110       120
E2      HKFNSSGCPERLASCRPLTDFDQGWGPISYANGSGPDQRPYCWHYPPKPCGIVPAKSVCG
        .:::::::::::::::::.:::::::::::.:::::::::::::::::::::::::.::::
Ay6510  NKFNSSGCPERLASCRPLADFDQGWGPISYTNGSGPDQRPYCWHYPPKPCGIVPAESVCG
               70        80        90       100       110       120

              130       140       150       160       170       180
E2      PVYCFTPSPVVVGTTDRSGAPTYSWGENDTDVFVLNNTRPPLGNWFGCTWMNSTGFTKVC
        :::::::::::::::::::::::.::::.::::::::::: :::::: ::::::::::::
Ay6510  PVYCFTPSPVVVGTTDRSGAPTYNWGENETDVFVLNNTRPRLGNWFGGTWMNSTGFTKVC
              130       140       150       160       170       180

              190       200       210       220       230       240
E2      GAPPCVIGGAGNNTLHCPTDCFRKHPDATYSRCGSGPWITPRCLVDYPYRLWHYPCTINY
        :::::.:::.:::::.::::::::::.::::::::::::::::::. ::::::::::::::
Ay6510  GAPPCAIGGVGNNTLYCPTDCFRKHPEATYSRCGSGPWITPRCLIHYPYRLWHYPCTINY
              190       200       210       220       230       240

              250       260       270       280       290       300
E2      TIPKIRMYVGGVEHRLEAACNWTRGERCDLEDRDRSELSPLLLTTTQWQVLPCSFTTLPA
        :::::::.::::::::.:::::::::::::.::::.:::::::.::::::::::::::::
Ay6510  TIPKIRMFVGGVEHRLDAACNWTRGERCDLDDRDRAELSPLLLSTTQWQVLPCSFTTLPA
              250       260       270       280       290       300

              310       320       330       340       350       360
E2      LSTGLIHLHQNIVDVQYLYGVGSSIASWAIKWEYVVLLFLLLADARVCSCLWMMLLISQA
        ::::::::::::::::::::..:....::.:::::::::::::::::.:.::::::::::.
Ay6510  LSTGLIHLHQNIVDVQYLYGLSSAVTSWVIKWEYVVLLFLLLADARICACLWMMLLISQV
              310       320       330       340       350       360

              370       380       390       400       410       420
E2      EAALENLVILNAASLAGTHGLVSFLVFFCFAWYLKGKWVPGAVYTFYGMWPLLLLLLALP
        :::::::..::::::.::::.: :..::: :::::::.:: .:. ::::::::::::::
Ay6510  EAALENLIVLNAASLVGTHGIVPFFIFFCAAWYLKGKWAPGLAYSVYGMWPLLLLLLALP
              370       380       390       400       410       420

E2      QRAYA
        :::::
Ay6510  QRAYA
```

Fig 23

```
                10        20        30        40        50        60
HCV1    LDTEVAASCGGVVLVGLMALTLSPYYKRYISWCLWWLQYFLTRVEAQLHVWIPPLNVRGG
        :: :.:::::..:.. : .:::::::.:..   .:::::.:::.:: :.::.::::.:::
Ay6510  LDQELAASCGATVFICLAVLTLSPYYKQYMARGIWWLQYMLTRAEALLQVWVPPLNARGG
                10        20        30        40        50        60

                70        80        90       100       110       120
HCV1    RDAVILLMCAVHPTLVFDITKLLLAVFGPLWILQASLLKVPYFVRVQGLLRPCALARKMI
        ::.:.:: :..:: :.:.:::..:.::.::::::::::::::::::::::::.:::::::.
Ay6510  RDGVVLLTCVLHPHLLFEITKIMLAILGPLWILQASLLKVPYFVRVQGLLRICALARKMV
                70        80        90       100       110       120
```

Fig. 23 continued

```
              130       140       150       160       170       180
HCV1    GGHYVQMVIIKLGALTGTYVYNHLTPLRDWAHNGLRDLAVAVEPVVFSQMETKLITWGAD
        ::::::::  ::::::::::.::::::::::::::.::::::::::::::::::::::::
Ay6510  GGHYVQMVTIKLGALTGTYIYNHLTPLRDWAHNGLQDLAVAVEPVVFSQMETKLITWGAD
              130       140       150       160       170       180

              190
HCV1    TAACGDIINGLPVSARR
        :::::::::::::::::
Ay6510  TAACGDIINGLPVSARR
              190
```

Fig 24:

```
               10        20        30        40        50        60
HCV1    GREILLGPADGMVSKGWRLLAPITAYAQQTRGLLGCIITSLTGRDKNQVEGEVQIVSTAA
        :.:::::::::::.:.:::::::::::::::::::::::::::::::::::::::::::
Ay6510  GQEILLGPADGMASRGWRLLAPITAYAQQTRGLLGCIITSLTGRDKNQVEGEVQIVSTAA
               10        20        30        40        50        60

               70        80        90       100       110       120
HCV1    QTFLATCINGVCWTVYHGAGTRTIASPKGPVIQMYTNVDQDLVGWPAPQGSRSLTPCTCG
        :::::::::::::::::::::::::::: ::::: :::::::::::  :::    ::.::
Ay6510  QTFLATCINGVCWTVYHGAGTRTIASSKGPVILMYTNVDQDLGGWTAPQVLGSLTPWSCG
               70        80        90       100       110       120

              130       140       150       160       170       180
HCV1    SSDLYLVTRHADVIPVRRRGDSRGSLLSPRPISYLKGSSGGPLLCPAGHAVGIFRAAVCT
        :::::::::::::::::::::::..::::::::::::::::::::::::::::::::::
Ay6510  SSDLYLVTRHADVIPVPRRGETRGSLLSPRPISYLKGSSGGPLLCPMGHAVGIFRAAVCT
              130       140       150       160       170       180

              190       200       210       220       230       240
HCV1    RGVAKAVDFIPVENLETTMRSPVFTDNSSPPVVPQSFQVAHLHAPTGSGKSTKVPAAYAA
        ::::::::::.:::.:::::::::::::::   .::::.:::::::::::::::::::::
Ay6510  RGVAKAVDFVPVESLETTMRSPVFTDNSSPLTVPQSYQVAHLHAPTGSGKSTKVPAAYAA
              190       200       210       220       230       240

              250       260       270       280       290       300
HCV1    QGYKVLVLNPSVAATLGFGAYMSKAHGIDPNIRTGVRTITTGSPITYSTYGKFLADGGCS
        :::::::::::::::::::::::::::::::::::::::::::::::::::::::::::
Ay6510  QGYKVLVLNPSVAATLGFGAYMSKAHGIDPNIRTGVRTITTGSPITYSTYGKFLADGGCP
              250       260       270       280       290       300

              310       320       330       340       350       360
HCV1    GGAYDIIICDECHSTDATSILGIGTVLDQAETAGARLVVLATATPPGSVTVPHPNIEEVA
        :::::::::::::.::::::::::::::::::::.:::::::::::::::::: :::::
Ay6510  GGAYDIIICDECHSVDATSILGIGTVLDQAETAGVRLTVLATATPPGSVTVPHSNIEEVA
              310       320       330       340       350       360

              370       380       390       400       410       420
HCV1    LSTTGEIPFYGKAIPLEVIKGGRHLIFCHSKKKCDELAAKLVALGINAVAYYRGLDVSVI
        ::. :::::::::::::: . ::::::::::::::::::::::: . ::::::::::::::
Ay6510  LSADGEIPFYGKAIPLNYIKGGRHLIFCHSKKKCDELAAKLVGPGVNAVAFYRGLDVSVI
              370       380       390       400       410       420
```

Fig. 24 continued

```
                 430       440       450       460       470       480
HCV1    PTSGDVVVVATDALMTGYTGDFDSVIDCNTCVTQTVDFSLDPTFTIETITLPQDAVSRTQ
        ::.::::::::::::::.::::::::::::::.:::::::::  .::: :.:::::::.:
Ay6510  PTTGDVVVVATDALMTGFTGDFDSVIDCNTCVVQTVDFSLDPIPSIETSTVPQDAVSRSQ
                 430       440       450       460       470       480

                 490       500       510       520       530       540
HCV1    RRGRTGRGKPGIYRFVAPGERPSGMFDSSVLCECYDAGCAWYELTPAETTVRLRAYMNTP
        ::::::::: ::::.:.::::::::::: :::::::::::::::::::::::::::.:::
Ay6510  RRGRTGRGKHGIYRYVSPGERPSGMFDSVVLCECYDAGCAWYELTPAETTVRLRAYLNTP
                 490       500       510       520       530       540

                 550       560       570       580       590       600
HCV1    GLPVCQDHLEFWEGVFTGLTHIDAHFLSQTKQSGENLPYLVAYQATVCARAQAPPPSWDQ
        :::::::::::::.::::::::::::::::::::::.::::::::::::::.::::::::
Ay6510  GLPVCQDHLEFWESVFTGLTHIDAHFLSQTKQSGENFPYLVAYQATVCARARAPPPSWDQ
                 550       560       570       580       590       600

                 610       620       630       640       650
HCV1    MWKCLIRLKPTLHGPTPLLYRLGAVQNEITLTHPVTKYIMTCMSADLEVVT
        :::::::::::: : ::::::::.::::::::::.:.:::.::::::::::
Ay6510  MWKCLIRLKPTLTGATPLLYRLGSVQNEITLTHPITQYIMACMSADLEVVT
                 610       620       630       640       650
```

Fig 25

```
                  10        20        30        40        50        60
HCV1    STWVLVGGVLAALAAYCLSTGCVVIVGRVVLSGKPAIIPDREVLYREFDEMEECSQHLPY
        ::::::::::::::::::::: ::::::..:.::::.:::::::::::::::::. :.::
Ay6510  STWVLVGGVLAALAAYCLSTGSVVIVGRIILGGKPAVIPDREVLYREFDEMEECAAHVPY
                  10        20        30        40        50        60

                  70        80        90       100       110       120
HCV1    IEQGMMLAEQFKQKALGLLQTASRQAEVIAPAVQTNWQKLETFWAKHMWNFISGIQYLAG
        .:::: :::::::::::::::::.:.:.:.: ::.::::::.::::::::::.:::::::
Ay6510  LEQGMHLAEQFKQKALGLLQTASKQTETITPIVQSNWQKLESFWAKHMWNFVSGIQYLAG
                  70        80        90       100       110       120

                 130       140       150       160       170       180
HCV1    LSTLPGNPAIASLMAFTAAVTSPLTTSQTLLFNILGGWVAAQLAAPGAATAFVGAGLAGA
        ::::::::::::::.:::::::::::.:::::::::::.:::::::.:::::::::..::
Ay6510  LSTLPGNPAIASLMSFTAAVTSPLTTQQTLLFNILGGWLAAQLAAPAAATAFVGAGITGA
                 130       140       150       160       170       180

                 190       200       210       220       230       240
HCV1    AIGSVGLGKVLIDILAGYGAGVAGALVAFKIMSGEVPSTEDLVNLLPAILSPGALVVGVV
        ..:::::::::.:::::::::::::::::::::::.:.:::::::::::::::::::.::
Ay6510  VVGSVGLGKVLVDILAGYGAGVAGALVAFKIMSGETPTTEDLVNLLPAILSPGALVVAVV
                 190       200       210       220       230       240

                 250       260       270       280       290       300
HCV1    CAAILRRHVGPGEGAVQWMNRLIAFASRGNHVSPTHYVPESDAAARVTAILSSLTVTQLL
        :::::::::: :::::::::::::::::::::::::::::::::.:::: ::. :::::::
Ay6510  CAAILRRHVGLGEGAVQWMNRLIAFASRGNHVSPTHYVPESDASARVTPILTRLTVTQLL
```

```
               250       260       270       280       290       300

               310
HCV1    RRLHQWISSECTTPC
        . :: ::::.: .::
Ay6510  KGLHVWISSNCIAPC
               310
```

Fig 26

```
                10        20        30        40        50        60
HCV1    SGSWLRDIWDWICEVLSDFKTWLKAKLMPQLPGIPFVSCQRGYKGVWRVDGIMHTRCHCG
        ..:::.:.:.::::::::::.::::::.::::::::::::::::.:::: .::.:::: ::
Ay6510  ASSWLKDVWNWICEVLSDFKNWLKAKLVPQLPGIPFVSCQRGYRGVWRGEGIVHTRCPCG
                10        20        30        40        50        60

                70        80        90       100       110       120
HCV1    AEITGHVKNGTMRIVGPRTCRNMWSGTFPINAYTTGPCTPLPAPNYTFALWRVSAEEYVE
        :.::::::::.::::::.:: : : :.::::::::::::: :::::::::::::::::::
Ay6510  ANITGHVKNGSMRIVGPKTCSNTWRGSFPINAYTTGPCTPSPAPNYTFALWRVSAEEYVE
                70        80        90       100       110       120

               130       140       150       160       170       180
HCV1    IRQVGDFHYVTGMTTDNLKCPCQVPSPEFFTELDGVRLHRFAPPCKPLLREEVSFRVGLH
        .:..::::::::.:::.:::::::::::: ::.:::::::.:::::::::.::.: ::..
Ay6510  VRRLGDFHYVTGVTTDKLKCPCQVPSPEFSTEVDGVRLHRYAPPCKPLLRDEVTFSVGFN
               130       140       150       160       170       180

               190       200       210       220       230       240
HCV1    EYPVGSQLPCEPEPDVAVLTSMLTDPSHITAEAAGRRLARGSPPSVASSSASQLSAPSLK
        :: ::::::::::::::.:::::::::::::..:.::: ::::::.::::::::::::::
Ay6510  EYLVGSQLPCEPEPDVAALTSMLTDPSHITAKTAARRLKRGSPPSLASSSASQLSAPSLK
               190       200       210       220       230       240

               250       260       270       280       290       300
HCV1    ATCTANHDSPDAELIEANLLWRQEMGGNITRVESENKVVILDSFDPLVAEEDEREISVPA
        ::::..::::::.:::::::::.::::::::::::::.:.::::::::::::.::::.::
Ay6510  ATCTTHHDSPDADLIEANLLWRREMGGNITRVESENKIVVLDSFDPLVAEEDDREISIPA
               250       260       270       280       290       300

               310       320       330       340       350       360
HCV1    EILRKSRRFAQALPVWARPDYNPPLVETWKKPDYEPPVVHGCPLPPPKSPPVPPPRKKRT
        ::::: ..:  :.:.:::::::::::: ::.:: .::.::::::::::  ::::::::::
Ay6510  EILRKFKQFPPAMPIWARPDYNPPLVEPWKRPDCDPPLVHGCPLPPPKPTPVPPPRKKRT
               310       320       330       340       350       360

               370       380       390       400       410       420
HCV1    VVLTESTLSTALAELATRSFGSSSTSGITGDNTTTSSEPAPSGCPPDSDAESYSSMPPLE
        ::: :::.:.:::::::..::::.:::.:.  ...::         ::.:::::::::::
Ay6510  VVLDESTVSSALAELATKTFGSSTTSGVTSGEAAESSPALSCDGELDSEAESYSSMPPLE
               370       380       390       400       410       420

               430       440       450       460       470       480
HCV1    GEPGDPDLSDGSWSTVSSEANAEDVVCCSMSYSWTGALVTPCAAEEQKLPINALSNSLLR
        :::::::::::::::::::...:::::::::::::::::.::::::: ::::::::::::
```

Fig. 26 continued

```
Ay6510  GEPGDPDLSDGSWSTVSSDGGTEDVVCCSMSYSWTGALITPCAAEETKLPINALSNSLLR
                    430       440       450       460       470       480

                    490       500       510       520       530       540
HCV1    HHNLVYSTTSRSACQRQKKVTFDRLQVLDSHYQDVLKEVKAAASKVKANLLSVEEACSLT
        ::::::::::::: .::::::::::::::.::.:::::.:: :: :::.:::::::::::
Ay6510  HHNLVYSTTSRSAGKRQKKVTFDRLQVLDDHYRDVLKEAKAKASTVKAKLLSVEEACSLT
                    490       500       510       520       530       540

                    550       560       570       580       590       600
HCV1    PPHSAKSKFGYGAKDVRCHARKAVTHINSVWKDLLEDNVTPIDTTIMAKNEVFCVQPEKG
        :::::.:::::: :::: :. ::. ::::::.::::::.::::::::::::::::. :::
Ay6510  PPHSARSKFGYGPKDVRSHSSKAIRHINSVWQDLLEDNTTPIDTTIMAKNEVFCVKAEKG
                    550       560       570       580       590       600

                    610       620       630       640       650       660
HCV1    GRKPARLIVFPDLGVRVCEKMALYDVVTKLPLAVMGSSYGFQYSPGQRVEFLVQAWKSKK
        :::::::::.:::::::::: :::::: .::.:::: ::::::::.:::.::..::::::
Ay6510  GRKPARLIVYPDLGVRVCEKRALYDVVKQLPIAVMGPSYGFQYSPAQRVDFLLNAWKSKK
                    610       620       630       640       650       660

                    670       680       690       700       710       720
HCV1    TPMGFSYDTRCFDSTVTESDIRTEEAIYQCCDLDPQARVAIKSLTERLYVGGPLTNSRGE
        .:::::::::::::::::.:::::: .:: ::: :.::.::.:::::::.:::::::.:.
Ay6510  NPMGFSYDTRCFDSTVTEADIRTEEDLYQSCDLVPEARAAIRSLTERLYIGGPLTNSKGQ
                    670       680       690       700       710       720

                    730       740       750       760       770       780
HCV1    NCGYRRCRASGVLTTSCGNTLTCYIKARAACRAAGLQDCTMLVCGDDLVVICESAGVQED
        ::::::::::::::::::::.:::.:: :::::: ::::::::::::::::::::::.::
Ay6510  NCGYRRCRASGVLTTSCGNTITCYLKASAACRAAKLQDCTMLVCGDDLVVICESAGVKED
                    730       740       750       760       770       780

                    790       800       810       820       830       840
HCV1    AASLRAFTEAMTRYSAPPGDPPQPEYDLELITSCSSNVSVAHDGAGKRVYYLTRDPTTPL
        :::::::::::::::.::::: :::::::::::::::::::.::::.:::::::.: :::
Ay6510  AASLRAFTEAMTRYSGPPGDPAQPEYDLELITSCSSNVSVARDGAGQRVYYLTREPETPL
                    790       800       810       820       830       840

                    850       860       870       880       890       900
HCV1    ARAAWETARHTPVNSWLGNIIMFAPTLWARMILMTHFFSVLIARDQLEQALDCEIYGACY
        ::::::::::::::::::::::::::::.::.::::.::.::....::.::::::::: .
Ay6510  ARAAWETARHTPVNSWLGNIIMFAPTLWVRMVLMTHLFSILIVQEHLEKALDCEIYGATH
                    850       860       870       880       890       900

                    910       920       930       940       950       960
HCV1    SIEPLDLPPIIQRLHGLSAFSLHSYSPGEINRVAACLRKLGVPPLRAWRHRARSVRARLL
        :. ::::: :::::::::::::::::::::::::.:::::::::::::::::::::: ::
Ay6510  SVPPLDLPEIIQRLHGLSAFSLHSYSPGEINRVASCLRKLGVPPLRAWRHRARSVRATLL
                    910       920       930       940       950       960

                    970       980       990      1000      1010      1020
HCV1    ARGGRAAICGKYLFNWAVRTKLKLTPIAAAGQLDLSGWFTAGYSGGDIYHSVSHARPRWI
        ..::.:::::::::::::.::::: :.  :..::::.:::.::::::::::::::::::.
Ay6510  SQGGKAAICGKYLFNWAVKTKLKLIPLPLASHLDLSNWFTGGYSGGDIYHSVSHARPRWF
                    970       980       990      1000      1010      1020
```

Fig. 26 continued

```
              1030
HCV1    WFCLLLLAAGVGIYLLPNR
         .::::::..:::::::::::
Ay6510 LWCLLLLSVGVGIYLLPNR
              1030
```

Fig: 27

The sequence of the primers for the 5`UTR region were:

SEQ ID No. 19 HCV -1F : 5' - GCC AGC CCCCTG ATG GGG G 3'

SEQ ID No. 20HCV-383R: 5' - gtt tag gat tcg tgc tca tgg tgc 3'

The sequence of the primers for the Core region were:

SEQ ID No. 21 HCV – 340F: 5' gaccgtgcaccatgagcacgaatcc 3'

SEQ ID No. 22 HCV – 920R: 5' tcc gac ggc cga agc ggg ca 3'

The sequence of the primers for the E1 region were:

SEQ ID No. 23 HCV- 837F: 5' ccc ggt tgc tct ttc tct atc ttc 3'

SEQ ID No. 24 HCV-1262R: 5' gga tag atg gag caa ttg cag tct tg 3'

The sequence of the primers for the E1 and E2 region were:

SEQ ID No. 25 HCV-1233F: 5' caa gac tgc aat tgc tcc atc tat c 3'

SEQ ID No. 26 HCV-2248R: 5' agc ctg tgc tcg acc ccc ccc aca tac atc ct 3's

The sequence of the primers for the E2 and NS1 region were:

SEQ ID No. 27 HCV-2010F: 5' caa ctgg attc acc aag gtg 3'

SEQ ID No. 28 HCV-3040R: 5' gca gac tgg cct gca aga tc 3'

The sequence of the primers for the NS2 and NS3 region were:

SEQ ID No. 29 HCV-3000F: 5' aca tca cca aaa tca tgc t 3'

SEQ ID No. 30 HCV-4040R: 5' ccc agt ggg tgc gta atg 3'

The sequence of the primers for the NS3 region were:

SEQ ID No. 31 HCV-3891F - 5' cgc gga tcc gtg tgc acc cgt ggg gtt gca aag 3'

SEQ ID No. 32 HCV-5315R: 5' cga ggc ttc tag cta gtg acg acc tcc agg tcc gc 3'

The sequence of the primers for the NS4 region were:

SEQ ID No. 33 HCV-5477F: 5' cgc gga tcc gcc cac gtc ccc tac ctc gag cag 3'

SEQ ID No. 34 HCV-6260R: 5' cga agc ttc taa gca cac ggg gcg atg caa tcc ga 3'

The sequence of the primers for the NS5A region were:

SEQ ID No. 35 HCV-6281F: 5' ctg gga ctg gat atg cga ggt gct gag cg 3'

SEQ ID No. 36 HCV-7405R: 5' gag ctg cca agg tct tag tgg caa gct c 3'

Fig. 27 continued

The sequence of the primers for the NS5B region were:

SEQ ID No. 37 HCV – 7200F: 5` tat ggg cac ggc cgg att at 3`

SEQ ID No. 38 HCV – 8030R: 5` ttc att ctt ggc cat gat ggt a 3`

The sequence of the primers for the NS5B and 3`UTR region were:

SEQ ID No. 39 HCV-8000F: 5` ata gac act acc atc atg gcc a 3`

SEQ ID No. 40 HCV – 9414: 5`acg ggg cct aaa ggc ctg gag 3`

HEPATITIS C VIRUS VACCINE

CROSS-REFERENCE TO RELATED APPLICATIONS

This application is a division of U.S. application Ser. No. 11/447,049, filed Jun. 6, 2006, which issued as U.S. Pat. No. 7,348,011 on Mar. 25, 2008, which claims priority to U.S. Provisional Application No. 60/689,090, filed Jun. 10, 2005.

BACKGROUND

The present invention relates to isolation of a novel Hepatitis C virus. More particularly, the present invention relates to a viral class Hepatitis C, polypeptides, polynucleotide, vaccine and antibodies derived there from.

Viral hepatitis, caused by the six hepatotropic viruses, viz, hepatitis A virus (HAV) hepatitis B virus (HBV), Hepatitis D virus (HDV), hepatitis E virus (HEV) and hepatitis G virus (HGV), represents a major health problem world wide.

Hepatitis B Virus (HBV) and Hepatitis C Virus (HCV) are the major cause of devastating liver diseases all over the world. Recent estimates indicate that more than 500 million people appeared to have been infected by these liver-tropic viruses. With about 180 million people currently infected worldwide, HCV represents a daunting public health problem. Out of these, at least 15-20 million in India and about 4 million people in the USA suffer from chronic infection by HCV. In some countries like Egypt about 10 to 15 percent of general population appears to carry HCV. More than 30 to 40% of the infected people develop liver cirrhosis and/or hepatocellular carcinoma after suffering with chronic infection for a decade or two and therefore HCV infection is considered to be a silent killer. Although interferon $\alpha$ in combination with ribavirin work well with some patients infected by some genotypes, more than 50% of the patients are refractory to such treatment.

Non-A, Non-B hepatitis (NANBH) are transmissible diseases that are believed to be viral induced, and that are distinguishable from other forms of viral-associated liver diseases, including that caused by the known hepatitis viruses. Viral hepatitis, caused by the hepatotropic viruses, viz, hepatitis A virus (HAV) hepatitis B virus (HBV), Hepatitis D virus (HDV), hepatitis E virus (HEV) and hepatitis G virus (HGV), represents a major health problem world wide. Until recently there has been neither clarity nor agreement as to the identity or specificity of the antigen antibody systems associated with agents of NANBH. It is possible that NANBH is caused by more than one infectious agent and unclear what the serological assays detect in the serum of patients with NANBH.

In 1987, Houghton, et al. cloned the first virus definitively linked to NANBH. Houghton et al. described there in the cloning of an isolate from a new viral class, hepatitis C virus (HCV), the prototype isolate described therein being named "HCV1". HCV is a Flavi-like virus, with an RNA genome. They described the production of recombinant proteins from HCV sequences that are useful as diagnostic reagents, as well as polynucleotides useful in diagnostics hybridization assays and in cloning of additional HCV isolates.

Hepatitis C virus (HCV) has emerged in recent years as the leading cause of worldwide blood-transmitted chronic hepatitis, liver cirrhosis, and hepatocellular carcinoma. A vaccine to prevent HCV infection has not yet been available any where in the world and the existing antiviral treatments are ineffective in the majority of the HCV infected patients.

Despite significant progress in the field of biotechnology, reliable diagnostic procedures, an alternative animal model other than chimpanzee, efficient cell culture systems that can support long-term replication of the virus and effective therapeutic strategies are still lacking.

As with any disease, an accurate diagnosis of HCV infection is essential before patients are counseled and treatment is initiated. Since, the identification and molecular characterization of the HCV in 1989 by Choo and colleagues, a number of diagnostic tests based on the detection of either the anti HCV antibodies or HCV-RNA by PCR in patient sera have been developed.

Presently, a third generation ELISA that incorporates antigens from the Core, NS3, NS4 and NS5 proteins of HCV, representing about 60% of the total amino acid sequence of HCV polyprotein, is available in the market. Although, this ELISA is significantly sensitive, a major drawback of this assay is that it fails to differentiate between active and post infection cases. In addition to this, it is now well documented that the commercially available third generation ELISA can not be used to detect all the viral infections in Indian patients owing to genotype sequence variations.

It may be noted at this stage that the commercial $3^{rd}$ EIA is based on genotype 1 (other than Indian HCV strain) and genotype specific antibody response in this virus is now documented.

Hepatitis, Cirrhosis and Hepatocellular carcinoma, caused by Hepatitis C Virus remain a global health problem and development of a vaccine to prevent this silent killer is of utmost priority. Every major country's goal is to produce a therapeutic vaccine for those 180 million people who are already infected by HCV and a preventive vaccine to eradicate future HCV infections. Just a few years ago, there was a lot of skepticism about the possibility of developing a viable vaccine for HCV. The situation, however, has changed in the last two to three years mainly because i) about 40 to 50% of the patients spontaneously recover from infection, implying that their immune system can fight off the virus; ii) infected chimpanzees (the only animal model available for HCV produced viremia) and convalescent humans are protected against the re-exposure; and iii) chronically infected patients improved their immune response and liver functions when the viral envelope protein E1 was administered as therapeutic vaccine.

Luckily for Hepatitis B, there is a preventive vaccine available in most of the countries; thus, future infections can be prevented. A therapeutic vaccine for HBV to boost the immunity of the infected people may be forthcoming. Unfortunately such a vaccine is not available for HCV any where in the world. Because of the propensity of the virus to undergo genetic variation, resulting in the evolution of quasispecies, a vaccine developed in the western countries will not be effective in India. For that matter, a vaccine developed against the strain(s) prevalent in Northern India may not be effective in South India. Therefore, controlling HCV infection is a challenging task. With the recent breakthroughs in research and development on HCV, there is a lot of optimism now about the development of at least a therapeutic and a potential preventive vaccine.

The major problem, however, is that a single vaccine may not be suitable for every country as there are several different genotypes. In India genotypes 1 and 3 are more prevalent, which are quite different from genotypes existing in other regions of the world. Therefore, our major goal is to make the vaccine candidate proteins, E1 and E2 for both genotypes in yeast and/or animal cells and test for their efficacy as therapeutic and preventive vaccines. We already know the sequence of these genotypes and we have also completed cloning of the genes encoding E1 and E2 proteins. Now, the major goal of this project is to make these proteins in large quantities, purify and characterize, and carry out human trials.

There is an ever-increasing demand for sensitive and accurate tests for detection and screening of Hepatitis viral carriers. There is also a need for effective vaccines and therapeutic agents for preventing and treating viral hepatitis. Moreover, there is tremendous genetic variation among existing strains from each country and thus development of potential vaccines depend upon characterization of the strain(s) existing among Indian population.

To overcome the problems associated with the prior art, the applicant has cloned and sequenced the genome of a novel Indian strain of HCV. This sequence can be used to develop HCV antigens, diagnostic kits and therapeutic vaccines.

The principal objective of the present invention is to isolate a novel strain of Hepatitis C Virus from a pool of Indian patients.

Another objective of the present invention is to characterize the novel strain of Hepatitis C Virus.

Yet another objective of the present invention is to identify the polynucleotide sequence for the novel strain of Hepatitis C Virus.

Still another objective of the present invention is to identify the polypeptide sequence for the novel strain of Hepatitis C Virus.

Still another objective of the present invention is to identify the primers.

Still another objective of the present invention is to develop a therapeutic vaccine for immunizing a subject with Hepatitis C infection.

Still another objective of the present invention is to develop a kit for identifying a subject with Hepatitis C infection.

Still another objective of the present invention is to develop a method of diagnosing a patient with Hepatitis C infection.

Still another objective of the present invention is to immunize a subject with Hepatitis C infection.

SUMMARY

New isolates of HCV has been characterized from different parts of the world have been implicated as NANBH carriers. These isolates exhibit nucleotide and amino acid sequence heterogeneity with respect to the prototype isolate HCV1, in several viral domains. It is believed that these distinct sequences are of in importance, particularly in diagnostic assays and in vaccine development.

The invention relates to a novel class of Hepatitis C virus that has been isolated and characterized from an Indian infected host. The entire genomic structure and the nucleotide sequence of the novel HCV isolate have been deduced. The genome appears to be single-stranded RNA comprising about 9442 nucleotides. When compared with all known viral sequences, several distinct domains and sequences that are of much importance clinically, particularly for diagnostic purposes and for vaccine development have been observed. The said sequence has been deposited at the GenBank at accession number AY651061. The said novel strain has been designated as Khajal.

Indian HCV isolate has been characterized from a chronic hepatitis C patient. Blood was collected form this patient, the RNA and cDNA was isolated and the PCR reaction was set up using specific primers. The PCR amplicons were cloned and sequenced.

This isolate exhibits nucleotide and amino acid sequence heterogeneity with respective to prototype isolate in several viral domains. These distinct sequences are much in importance, particularly in diagnostic assays and in vaccine development.

In one aspect, the invention provides novel nucleotide sequences, obtained from the novel HCV strain resulting polynucleotide, polypeptides and antibodies derived there from. The invention also provides purified polypeptide sequences obtained from novel isolate, said sequence being distinct from that of currently known HCV isolates. The invention includes recombinant vectors comprising said sequences and host cells transformed with such vectors.

Further, the invention provides probes derived from the HCV cDNA useful for diagnose of the presence of HCV in samples, and to isolate naturally occurring variants of the virus.

The invention also provides antibodies, both polyclonal and monoclonal, directed against HCV epitopes contained within these polypeptide sequences are also useful for diagnostic tests, as therapeutic agents, for screening of antiviral agents.

Also included within scope of the invention is an monoclonal antibody directed against an HCV epitope and an anti-idiotype antibody comprising a region which mimics an HCV epitope.

Another aspect of the invention relates to kit for detection of HCV comprising: polynucleotides derived from the novel HCV isolate comprising a polynucleotide probe provided in a suitable container; an HCV antigen comprising an antibody directed against the HCV antigen to be detected, provided in a suitable container; antibodies directed against an HCV antigen comprising a polypeptide containing an HCV epitope present in the HCV antigen, provided in a suitable container.

Immunoassays are also included in the invention. These include an immunoassay for detecting an HCV antigen comprising incubating a sample suspected of containing an HCV antigen with a probe antibody directed against the HCV antigen to be detected under conditions which allow the formation of an antigen-antibody complex; and detecting an antigen-antibody complex containing the probe antibody. An immunoassay for detecting antibodies directed against an HCV antigen comprising incubating a sample suspected of containing anti-HCV antibodies with a probe polypeptide which contains an epitope of the HCV, under conditions which allow the formation of an antibody-antigen complex; and detecting the antibody-antigen complex containing the probe antigen.

Also included in the invention are vaccines for treatment of HCV infection comprising an immunogenic peptide containing an HCV epitope, or an inactivated preparation of HCV, or an attenuated preparation of HCV. These and other embodiments of the present invention will be readily apparent to those of ordinary skill in the art in view of the following description.

BRIEF DESCRIPTION OF THE DRAWINGS

FIG. 9: Nucleotide and polypeptide sequences of the HCV isolate AY651061 (SEQ ID NOS:3-18);

FIG. 10: Polypeptide and nucleotide sequences of the HCV isolate AY651061, complete sequence (SEQ ID NOS: 1 and 2);

FIG. 11: Nucleotide sequence comparison of HCV1 5'UTR (SEQ ID NO: 41) vs. AY651061 5'UTR (SEQ ID NO: 3);

FIG. 12: Nucleotide sequence comparison of HCV1 CORE (SEQ ID NO: 42) vs. AY651061 CORE (SEQ ID NO: 5);

FIG. 13: Nucleotide sequence comparison of HCV1 E1 (SEQ ID NO: 43) vs. AY651061 E1 (SEQ ID NO: 7);

FIG. 14: Nucleotide sequence comparison of HCV1 E2/NS1 (SEQ ID NO: 44) vs. AY651061 E2/NS1 (SEQ ID NO: 9);

FIG. 15: Nucleotide sequence comparison of HCV1 NS2 (SEQ ID NO: 45) vs. AY651061 NS2 (SEQ ID NO: 11);

FIG. 16: Nucleotide sequence comparison of HCV1 NS3 (SEQ ID NO: 46) vs. AY651061 NS3 (SEQ ID NO: 13);

FIG. 17: Nucleotide sequence comparison of HCV1 NS4 (SEQ ID NO: 47) vs. AY651061 NS4 (SEQ ID NO: 15);

FIG. 18: Nucleotide sequence comparison of HCV1 NS5 (SEQ ID NO: 48) vs. AY651061 NS5 (SEQ ID NO: 17);

FIG. 19: Nucleotide sequence comparison of HCV1 3'UTR (SEQ ID NO: 49) vs. AY651061 3'UTR (SEQ ID NO: 4);

FIG. 20: Amino acid comparison of HCV1 Core (SEQ ID NO: 50) vs. AY651061 Core (SEQ ID NO: 6);

FIG. 21: Amino acid comparison of HCV1 E1 (SEQ ID NO: 51) vs. AY651061 E1 (SEQ ID NO: 8);

FIG. 22: Amino acid comparison of HCV1 E2/NS1 (SEQ ID NO: 52) vs. AY651061 E2/NS1 (SEQ ID NO: 10);

FIG. 23: Amino acid comparison of HCV1 NS2 (SEQ ID NO: 53) vs. AY651061 NS2 (SEQ ID NO: 12);

FIG. 24: Amino acid comparison of HCV1 NS3 (SEQ ID NO: 54) vs. AY651061 NS3 (SEQ ID NO: 14);

FIG. 25: Amino acid comparison of HCV1 NS4 (SEQ ID NO: 55) vs. AY651061 NS4 (SEQ ID NO: 16);

FIG. 26: Amino acid comparison of HCV1 NS5 (SEQ ID NO: 56) vs. AY651061 NS5 (SEQ ID NO: 18); and FIG. 27: Nucleotide sequences for primers (SEQ ID NOS: 19-40).

DETAILED DESCRIPTION OF EMBODIMENTS

Figure 1:
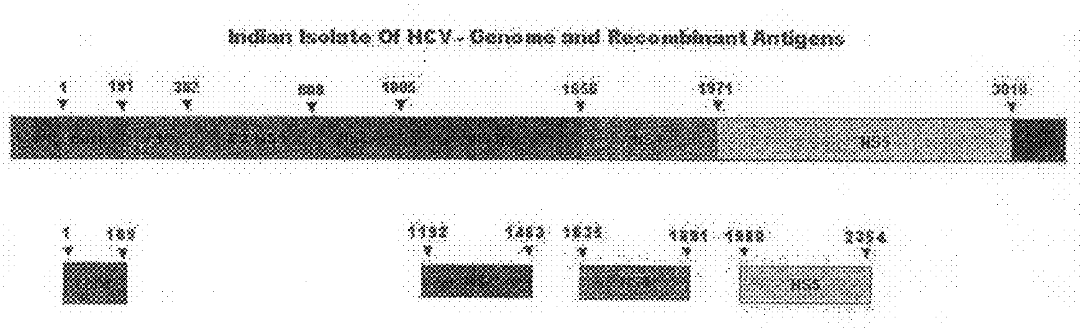
FIG. 1: Map of ORF of Hepatitis C virus isolate AY651061 and recombinant antigens.

The present invention is in relation to a hepatitis C virus polynucleotide sequence set forth in SEQ ID NO: 1 (FIG. 10) deposited at GenBank under accession number under AY651061.

Yet another embodiment of the present invention, wherein said sequence is isolated from Indian patient pool.

The present invention relates to a Hepatitis C virus polypeptide sequence set forth in SEQ ID NO: 2 (as shown in FIG. 10).

The present invention also relates to a polynucleotide sequence as set forth in SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, and SEQ ID NO: 17 encoding 5' untranslated region (UTR), 3' untranslated region (UTR), Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively.

The present invention further relates to a polypeptide sequence as set forth in SEQ ID No. 6, SEQ ID NO: 8, SEQ ID NO: 10, SEQ ID NO: 12, SEQ ID NO: 14, SEQ ID NO: 16, and SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively.

The present invention further relates to a Hepatitis C virus strain isolated from a Hepatitis C virus infected Indian patient pool.

The present invention furthermore relates to a pair of primers having sequences set forth in SEQ ID NOS: 19 and 20; SEQ ID NOS: 21 and 22; SEQ ID NOS: 23 and 24; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; SEQ ID NOS: 37 and 38; and SEQ ID NOS: 39 and 40.

The present invention further relates to a vaccine for immunizing a subject against hepatitis C virus comprising at least one protein having a polypeptide sequence as set forth in SEQ ID NO: 6, SEQ ID NO: 8, SEQ ID NO: 10, SEQ ID NO: 12, SEQ ID NO: 14, SEQ ID NO: 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively, optionally along with a pharmaceutically acceptable vaccine adjuvant.

Yet another embodiment of the present invention, wherein the subject is a mammal including humans.

In still another embodiment of the present invention, wherein said vaccine adjuvant is selected from a group comprising mineral salts (aluminum hydroxide and aluminum or calcium phosphate gels, oil emulsions and surfactant based formulations (MF59, micro-fluidized detergent stabilized oil-in-water emulsion)), particulate adjuvants (virosomes, polylactide co-glycolide, structured complex of saponins and lipids), microbial derivatives (natural and synthetic), endogenous human immunomodulators (hGM-CSF or hIL-12, Immudaptin) and inert vehicles such as gold particles.

The present invention relates to a kit for identifying hepatitis C virus comprising at least one antigenic peptide selected from a polypeptide sequence as set forth in SEQ ID NO: 6, SEQ ID NO: 8, SEQ ID NO: 10, SEQ ID NO: 12, SEQ ID NO: 14, SEQ ID NO: 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively, capable of reacting specifically with antibodies directed against said virus.

Yet another embodiment of the present invention, wherein said kit further comprises control standards and instructions for use of the kit.

The present invention relates to a method for detecting the presence of hepatitis C virus comprises contacting sera with at least one antigenic polypeptide selected from a polypeptide sequence as set forth in SEQ ID NO: 6, SEQ ID NO: 8, SEQ ID NO: 10, SEQ ID NO: 12, SEQ ID NO: 14, SEQ ID NO: 16, or SEQ ID NO: 18 corresponding to Core protein, Envelope glycoprotein (E1), Envelope glycoprotein (E2)/Non-structural protein NS1, Non-structural protein NS2, Non-structural protein NS3, Non-structural protein NS4, and Non-structural protein NS5, respectively, wherein formation of an immunogenic complex confirms detection of said virus.

The present invention relates to a method of immunization against hepatitis C virus in a subject in need thereof, wherein said method comprises administering a pharmaceutically effective immunizing dose of the vaccine.

Retrieved from "http://www.biology-online.org/dictionary/Therapeutic_vaccine"

This page has been accessed 34 times. This page was last modified 21:16, 3 Oct. 2005.

The practice of the present invention will employ, unless otherwise indicated, conventional techniques of molecular biology, microbiology, recombinant DNA techniques and immunology, which are within the skill of the art.

The term "hepatitis C virus" has been reserved by workers in the field for an unknown etiologic agent of NANBH. Accordingly, as used "hepatitis C virus" refers to an agent causative of NANBH, which was formerly referred to as NANBV and/or BB-NANBV from the class of the prototype isolate, HCV1 described by Houghton et al. HCV is a Flavi-like virus. The morphology and composition of flavivirus particle are known, and are discussed by Brinton (1986). Generally, with respect to morphology, Flaviviruses contain a central nucleocapsid surrounded by a lipid bilayer. Virions are spherical and have a diameter of about 40-50 nm. Their cores are about 25-30 nm in diameter. Along the outer surface of the virion envelope are projections that are about 5-10 nm long with terminal knobs about 2 nm in diameter.

In one of the embodiment, the HCV genome is comprised of RNA. It is known that RNA containing viruses have relatively high rates of spontaneous mutation, i.e., reportedly on the order of $10^{-3}$ to $10^{-4}$ per incorporated nucleotide. Therefore, there are multiple strains, which may be virulent or avirulent, within the HCV class of species. It is believed that the genome of HCV isolates is comprised of a single ORF of approximately 9,000 nucleotides to approximately 12,000 nucleotides encoding a polyprotein similar hydrophobic and antigenic character to that of HCV1. In addition, the genome is believed to be a positive stranded RNA.

Yet another embodiment comprises isolates of HCV comprise epitopes that are immunologically cross-reactive with epitopes in the HCV1 genome. At least some of these are epitopes unique to HCV when compared to other known Flaviviruses. The uniqueness of the epitope may be determined by its immunological reactivity with anti-HCV antibodies and lack of immunological reactivity with antibodies to other Flavivirus species. Methods for determining immunological reactivity are known in the art, such as, for example, radioimmunoassays, ELISAs, hemagglutination, and the several examples of suitable techniques provided herein.

In still another embodiment it is expected that the overall homology of HCV isolates and HCV1 genomes at the nucleotide level probably will be about 40% or greater, probably about 60% or greater, and even more probably about 80% to about 90% or greater. In addition that there are many corresponding contiguous sequences of at least 13 nucleotides that are fully homologous. The correspondence between the sequence from a new isolate and the HCV1 sequence can be determined by techniques known in the art. For example they can be determined by a direct comparison of the sequence information of the polynucleotide from the new isolate and HCV1 sequences. Alternatively homology can be determined by hybridization of the poly nucleotides under conditions which form stable duplexes between homologous regions.

In still another embodiment the evolutionary relationship strains or isolates of HCV the putative HCV strains or isolates are identifiable by their homology at the polypeptide level. Thus, new HCV isolates are expected to be more than about 40% homologous. probably more than about 70% homologous. and even more probably more than about 80% homologous, and possibly even more than about 90% homologous at the polypeptide level. The techniques for determining amino acid sequence homology are known in the art. For example, the amino acid sequence may be determined directly and compared to the sequences provided. Alternatively the nucleotide sequence of the genomic material of the putative HCV may be determined, the amino acid sequence encoded therein can be determined and the corresponding regions compared.

In still another embodiment the non-structural core and envelope domains of the polyprotein have been predicted for HCV1. The "C", or core, polypeptide is believed to be encoded from the 5' terminus to about nucleotide 345 of HCV1. The putative "E", or envelope, domain is believed to be encoded from about nucleotide 346 to about nucleotide 1050. Putative NS1, or non-structural one domain, is thought to be encoded from about nucleotide 1051 to about nucleotide 1953. For the remaining domains, putative NS2 is thought to be encoded from about nucleotide 1954 to about nucleotide, 3018, putative NS3 from about nucleotide 3019 to about nucleotide, 4950, putative NS4 from about nucleotide 4951 to about nucleotide 6297, and putative NS5 from about nucleotide 6298 to the 3' terminus.

In still another embodiment the portions of the cDNA sequences derived from HCV are useful as probes to diagnose the presence of virus in HCV infected individuals, and to isolate naturally occurring variants of the virus. These cDNAs also make available polypeptide sequences of HCV antigens encoded within the HCV genome(s) and permits the production of polypeptides which are useful as standards or reagents in diagnostic tests and are components as vaccines. Antibodies, including for example both polyclonal and monoclonal, directed against HCV epitopes contained within these polypeptide sequences are also useful for diagnostic tests, as therapeutic agents, for screening of antiviral agents, and for the isolation of the NANBH virus agent which these cDNAs derive. In addition, by utilizing probes derived from these cDNAs it is possible to isolate and sequence other portions of the HCV genome, thus giving rise to additional probes and polypeptides which are useful in the diagnosis and/or treatment, both prophylactic therapeutic, of NANBH.

In still another embodiment it is with respect to polynucleotides, some aspects of the invention are: a purified HCV polynucleotide; a recombinant HCV polynucleotide; a recombinant polynucleotide comprising a sequence derived from an HCV genome or from HCV cDNA; a recombinant polynucleotide encoding an epitope of HCV; a recombinant vector containing any of the above recombinant polynucleotides, and a host cell transformed with any of these vectors.

In still another embodiments of the invention: a recombinant expression system comprising an open reading frame (ORF) of DNA derived from an HCV genome or from HCV cDNA, wherein the ORF is operably linked to a control sequence compatible with a desired host, a cell transformed with the recombinant expression system, and a polypeptide produced by the transformed cell. Still other aspects of the invention are: a preparation of polypeptides from the purified HCV; a purified HCV polypeptide; a purified polypeptide comprising an epitope which is immunologically identifiable with an epitope contained in HCV.

In still another embodiment invention immunoassays are also included. These include an immunoassay for detecting an HCV antigen comprising incubating a sample suspected of containing an HCV antigen with a probe antibody directed against the HCV antigen to be detected under conditions which allow the formation of an antigen-antibody complex; and detecting an antigen-antibody complex containing the probe antibody. An immunoassay for detecting antibodies directed against an HCV antigen comprising incubating a sample suspected of containing anti-HCV antibodies with a probe polypeptide which contains an epitope of the HCV, under conditions which allow the formation of an antibody-antigen complex; and detecting the antibody-antigen complex containing the probe antigen.

In still another embodiment the term "polypeptide" is used referring to a polymeric form of nucleotide of any length, either ribonucleotides or deoxyribonucleotides. It also includes the known types of modifications, for example, labels which are known in the art, methylation, "caps", substitution of one or more of the naturally occurring nucleotides with an analog, internucleotide modifications, such as, for example, those with unchanged linkages, e.g., methyl phosphates, phosphotriesters, phosphoamidates, carbamates, etc. and with charged linkages. "Purified polypeptide" refers to a composition comprising a specified polypeptide that is substantially free of other components, such composition typically comprising at least about 70% of the specified polypeptide, more typically at least about 80%, 90% or even 95% to 99% of the specified polypeptide.

In still another embodiment the "recombinant host cells", "host cells", "cells", "cell lines", "cell cultures", and other such terms denote microorganisms or higher eukaryotic cell lines cultured as unicellular entities that can be, or have been, used as recipients for a recombinant vector or other transfer DNA, and include the progeny of the original cell which has been transformed. It is understood that the progeny of a single parental cell may not necessarily be completely identical in morphology or in genomic or total DNA complement as the original parent due to natural, accidental, or deliberate mutation.

In still another embodiment the term "replicon" is any genetic element, e.g., a plasmid, a chromosome, a virus, a cosmid, etc. that behaves as an autonomous unit of polynucleotide replication within a cell, i.e., capable of replication under its own control. A "cloning vector" is a replicon that can transform a selected host cell and in which another polynucleotide segment is attached, so as to bring about the replication and/or expression of the attached segment. Typically, cloning vectors include plasmids, virus, e.g., bacteriophage vector, and cosmids. An "integrating vector" is a vector that does not behave as a replicon in a selected host cell, but has the ability to integrate into a replicon (typically a chromosome) resident in the selected host to stably transform the host. An "expression vector" is a construct that can transform a selected host cell and provides for 30 expression of a heterologous coding sequence in the selected host. Expression vectors can be either a cloning vector or an integrating vector.

In still another embodiment the "coding sequence" is a polynucleotide sequence which is transcribed into, RNA and/or translated into a polypeptide when placed under the control of appropriate regulatory sequences. The boundaries of the coding sequence are determined by a translation start codon at the 5' terminus and a translation stop codon at the 3' terminus. A coding sequence can include, but is not limited to mRNA, cDNA and recombinant polynucleotide sequences. "Control sequence" refers to polynucleotide regulatory sequences which are necessary to affect the expression of coding sequences to which they are ligated. The nature of such control sequences differs depending upon the host organism. In prokaryotes, control sequences generally include promoter, ribosomal binding site and terminators. In eukaryotes generally control sequences include promoters, terminators and, in some instances, enhancers. The term "control sequences" is intended to include, at a minimum, all components the presence of which are necessary for expression and may also include additional advantageous components. "Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In still another embodiment an open reading frame or ORF is a region of a polynucleotide sequence which encodes a polypeptide: this region may represent a portion of a coding sequence or a total coding sequence.

In still another embodiment the term "immunologically cross-reactive" refers to two or more epitopes or polypeptides that are bound by the same antibody. Cross-reactivity can be determined by any of a number of immunoassay techniques, such as a competition assay. As used, the term "antibody" refers to a polypeptide or group of polypeptides which comprise at least one epitope. An "antigen binding site" is formed from the folding of the variable domains of an antibody molecule(s) to form three-dimensional binding sites with an internal surface shape and charge distribution complementary to the features of an epitope of an antigen, which allows for specific binding to form an antibody-antigen complex. An antigen binding site may be formed from a heavy- and/or light-chain domain (VH and VL, respectively), which form hypervariable loops which contribute to antigen binding.

In still another embodiment the term "epitope" refers to an antibody binding site usually defined by a polypeptide, but also by non-amino acid haptens. An epitope could comprise 3 amino acids in a spatial conformation which is unique to the epitope, generally an epitope consists of at least 5 such amino acids and more usually consists of at least 8-10 such amino acids. "Antigen-antibody complex" refers to the complex formed by an antibody that is specifically bound to an epitope on an antigen. "Immunogenic polypeptide" refers to a polypeptide that elicits a cellular and/or humoral immune response in a mammal whether alone or linked to a carrier in the presence or absence of an adjuvant. "Polypeptide" refers to a polymer of amino acids and does not refer to a specific length of the molecule. Thus peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art both naturally occurring and non-naturally occurring. "Transformation", as used refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid or alternatively, it may be integrated into the host genome. A "transformed" host cell refers to both the immediate cell that has undergone transformation and its progeny that maintain the originally exogenous polynucleotide. "Treatment" as used refers to prophylaxis and/or therapy. "Sense strand" refers to the strand of a double-stranded DNA molecule that is homologous to a mRNA transcript thereof. The "anti-sense strand" contains a sequence which is complementary to that of the "sense strand".

In still another embodiment an “antibody-containing body component” refers to a component of an individual’s body which is a source of the antibodies of interest. Antibody-containing body components are known in the art, and include, but are not limited to, whole blood and components thereof, plasma, serum, spinal fluid, lymph fluid, the external secretions of the respiratory, intestinal, and genitourinary tracts, tears, saliva, milk, white blood cells, and myelomas. “Purified HCV” isolate refers to a preparation of HCV particles which have been isolated from the cellular constituents with which the virus is normally associated, and from other types of viruses which may be present in the infected tissue. The techniques for isolating viruses are known to those of skill in the art, and include, for example centrifugation and affinity chromatography.

In still another embodiment an HCV “particle” is an entire virion, as well as particles which are intermediates in virion formation. HCV particles generally have one or more HCV proteins associated with the HCV nucleic acid. “Probe” refers to a polynucleotide which forms a hybrid structure with a sequence in a target polynucleotide, due to complementarity of at least one region in the probe with a region in the target. “Biological sample” refers to a sample of tissue or fluid isolated from an individual, including but not limited to, for example, whole blood and components thereof, plasma, serum, spinal fluid, and lymph fluid. The external secretions of the skin and respiratory, intestinal, and genitourinary tracts, tears, saliva, milk, blood cells, tumors, organs and samples of in vitro cell culture constituents (including, but not limited to, conditioned medium resulting from the growth of cells in cell culture medium, putatively virally infected cells, recombinant cells, and cell components).

In still another embodiment the present invention pertains to the isolation and characterization of a newly discovered isolate of HCV Indian isolate (AY651061), its nucleotide sequence, protein sequences and resulting polynucleotides, polypeptides and antibodies derived. Isolate Indian isolate (AY651061) is novel in its nucleotide and amino acid sequences and is believed to characteristic of HCV isolates from Indonesia.

In still another embodiment the nucleotide sequences derived from Indian isolate (AY651061) are useful as probes to diagnose the presence of virus in samples, and to isolate other naturally occurring variants of the virus. These nucleotide sequences also make available polypeptide sequences of HCV antigens encoded within the Indian isolate (AY651061) genome and permit the production of polypeptides which are useful as standards or reagents in diagnostic tests and/or as components of vaccines. Antibodies, both polyclonal and monoclonal, directed against HCV epitopes contained within these polypeptide sequences are also useful for diagnostic tests, as therapeutic agents, for screening of antiviral agents, and for isolating the NANBH virus. In addition, by utilizing probes derived from the sequences disclosed herein, it is possible to isolate and sequence other portions of the Indian isolate (AY651061) genome, thus giving rise to, additional probes and polypeptides which are useful in the diagnosis and/or treatment, both prophylactic and therapeutic, of NANB Hepatitis.

In still another embodiment the availability of the Indian isolate (AY651061) nucleotide sequences enable the construction of polynucleotide probes and polypeptides useful in diagnosing NANBH due to HCV infection and in screening blood donors as well as donated blood and blood products for infection. The Indian isolate (AY651061) sequences also allow the design and production of HCV specific polypeptides which are useful as diagnostic reagents for the presence of antibodies raised during NANBH. Antibodies to purified polypeptides derived from the Indian isolate (AY651061) sequences may also be used to detect viral antigens in infected individuals and in blood.

The knowledge of the Indian isolate (AY651061) sequences also enables the design and production of polypeptides which may be used as vaccines against HCV and also for the production of antibodies, which in turn may be used for protection against the disease and/or for therapy of HCV infected individuals. Moreover, the disclosed Indian isolate (AY651061) sequences enable further characterization of the HCV genome. Polynucleotide probes derived from these sequences, as well as from the HCV genome, may be used to screen cDNA libraries for additional viral cDNA sequences.

The Indian isolate (AY651061) polynucleotide sequences, the polypeptides derived and the antibodies directed against these polypeptides, are useful in the isolation and identification of the BBNANBV agent(s). For example, antibodies directed against HCV epitopes contained in polypeptides derived from the Indian isolate (AY651061) sequences may be used in processes based upon affinity chromatography to isolate the virus. Alternatively, the antibodies may be used to identify viral particles isolated by other techniques. The viral antigens and the genomic material within the isolated viral particles may then be further characterized.

The information obtained from further sequencing of the Indian isolate (AY651061) genome, as well as from further characterization of the Indian isolate (AY651061) antigens and characterization of the genomes enable the design and synthesis of additional probes and polypeptides and antibodies which may be used for diagnosis, for prevention, and for therapy of HCV induced NANB Hepatitis and for screening for infected blood and blood-related products.

In still another embodiment the DNA encoding the desired polypeptide, whether in fused or mature form, and whether or not it contains a signal sequence to permit secretion, may be ligated into expression vectors suitable for any convenient host. Both eukaryotic and prokaryotic host systems are presently used in forming recombinant polypeptides, and a summary of some of the more common control systems and host cells is given below. The polypeptide produced in such host cells is then isolated from lysed cells or from the culture medium and purified to the extent needed for its intended use. Such recombinant or synthetic HCV polypeptides can be used as diagnostics or those which give rise to neutralizing antibodies may be formulated into vaccines. Antibodies raised against these polypeptides can also be used as diagnostics or for passive immunotherapy. In addition, antibodies to these polypeptides are useful for isolating and identifying HCV particles.

In still another embodiment the observed relationship of the putative polyproteins of HCV and the Flaviviruses allows a predictor of the putative domains of the HCV “non-structural” (NS) proteins. The locations of the individual NS proteins in the putative Flavivirus precursor polyprotein are fairly well-known. Moreover, these also coincide with observed gross fluctuations in the hydrophobicity profile of the polyprotein. It is established that NS5 of Flaviviruses encodes the virion polymerase, and that NSI corresponds with a complement fixation antigen which has been shown to be an effective vaccine in animals. Recently, it has been shown that a Flavivirus protease function resides in NS3. Due to the observed similarities between HCV and the Flaviviruses, deductions concerning the approximate locations of the corresponding protein domains and functions in the HCV polyprotein are possible. The expression of polypeptides containing these domains in a variety of recombinant host cells including, for example, bacteria, yeast, insect and vertebrate cells, should give rise to important immunological reagents which can be used for diagnosis, detection and vaccines.

In still another embodiment although the non-structural protein region of the putative polyproteins of the HCV isolate described herein and of Flaviviruses appears to be generally similar, there is less similarity between the putative structural regions which are towards the N-terminus. In this region, there is a greater divergence in sequence, and in addition the hydrophobic profile of the two regions show less similarity. This "divergence" begins in the N-terminal region of the putative NS1 domain in HCV and extends to the presumed N-terminus. Nevertheless, it is still possible to predict the approximate locations of the putative nucleocapsid (N-terminal basic domain) and E (generally hydrophobic) domains within the HCV polyprotein.

In still another embodiment from these predictions it may be possible to identify approximate regions of the HCV polyprotein that could correspond with useful immunological reagents. For example, the E and NS1 proteins of Flaviviruses are known to have efficacy as protective vaccines. These regions, as well as some which are shown to be antigenic in the HCV1, for example those within putative NS3, C, and NS5, etc. should also provide diagnostic reagents.

In still another embodiment the immunogenicity of the HCV sequences may also be enhanced by preparing the sequences fused to or assembled with particle-forming proteins. In addition, all of the vectors prepared include epitopes specific to HCV having various degrees of immunogenicity such as, for example, the pre-S peptide. Thus, particles constructed from particle forming protein which includes HCV sequences are immunogenic with respect to HCV and particle-form protein.

In still another embodiment therapeutic vaccine may be prepared from one or more immunogenic polypeptides derived from Indian isolate (AY651061). The observed homology between HCV and Flaviviruses provides information concerning the polypeptides which are likely to be most effective as vaccines as well as the regions of the genome in which they are encoded. The general structure of the Flavivirus genome is discussed in Rice et al. (1986) in THE VIRUSES: THE TOGAVIRIDAE AND FLAVIVIRIDAE (Series eds. Fraenkel-Conrat and Wagner. Vol eds. Schlesinger and Schlesinger. Plenum Press). It is known that major neutralizing epitopes for Flaviviruses reside in the E (envelope) protein. Roehrig (1986) in THE VIRUSES: THE TOGAVIRIDAE AND FLAVIVIRIDAE, (Series eds. Fraenkel-Conrat and Wagner, Vol eds. Schlesinger and Schlesinger, Plenum Press). The corresponding HCV E gene and polypeptide encoding region may be predicted, based upon the homology to Flaviviruses. Thus, vaccines may be comprised of recombinant polypeptides containing epitopes of HCV E. These polypeptides may be expressed in bacteria, yeast, or mammalian cells, or alternatively may be isolated from viral preparations. It is also anticipated that the other structural proteins may also contain epitopes which give rise to protective anti-HCV antibodies. Thus, polypeptides containing the epitopes of E, C, and M may also be used, whether singly or in combination, in HCV vaccines.

In still another embodiment it has been shown that immunization with NS1 (non-structural protein 1), results in protection against yellow fever. Schlesinger et al. (1986) J. Virol. 60: 115-123. This is true even though the immunization does not give rise to neutralizing antibodies. Thus, particularly because this protein appears to be highly conserved among Flaviviruses, it is likely that HCV NS1 will also be protective against HCV infection. Moreover, it also shows that non-structural proteins may provide protection against viral pathogenicity, even if they do not cause the production of neutralizing antibodies.

In still another embodiment multivalent vaccines against HCV may be comprised of one or more epitopes from one or more structural proteins, and/or one or more epitopes from one or more non structural proteins.

In still another embodiment the vaccines may be comprised of, for example, recombinant HCV polypeptides and/or polypeptides isolated from the virions. In particular, vaccines are contemplated comprising one or more of the following HCV proteins, or subunit antigens derived therefrom: E, NS1, C, NS2, NS3, NS4 and NS5. Particularly preferred are vaccines comprising E and/or NS1, or subunits thereof. In addition, it may be possible to use inactivated HCV in vaccines: inactivation may be by the preparation of viral lysates, or by other means known in the art to cause inactivation of Flaviviruses, for example, treatment with organic solvents or detergents, or treatment with formalin. Moreover, vaccines may also be prepared from attenuated HCV strains or from hybrid viruses such as vaccinia vectors known in the art [Brown et al. Nature 319: 549-550].

In still another embodiment the proteins may be formulated into the vaccine as neutral or salt forms. Pharmaceutically acceptable salts include the acid addition salts (formed with free amino groups of the peptide) and which are formed with inorganic acids such as for example hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Generally, it is expected that the HCV genome sequence will be present in serum of infected individuals at relatively low levels i.e., at approximately $10^2$-$10^3$ chimp infectious doses (CID) per ml. This level may require that amplification techniques be used in hybridization assays.

In still another embodiment the Flavivirus model for HCV allows predictions regarding the likely location of diagnostic epitopes for the virion structural proteins. Similarly, domains of the non-structural proteins are expected to contain important diagnostic epitopes, e.g., NS5 encoding a putative polymerase and NS1 encoding a putative complement-binding antigen. Recombinant polypeptides, or viral polypeptides, which include epitopes from these specific domains may be useful for the detection of viral antibodies in infectious blood donors and infected patients. Moreover, these antibodies may be extremely useful in detecting acute-phase donors and patients.

In still another embodiment the antigenic regions of the putative polyprotein can be mapped and identified by screening the antigenicity of bacterial expression products of HCV cDNAs which encode portions of the polyprotein. Other antigenic regions of HCV may be detected by expressing the portions of the HCV cDNAS in other expression systems, including yeast systems and cellular systems derived from insects and vertebrates. In addition, studies giving rise to an antigenicity index and hydrophobicity/hydrophilicity profile give rise to information concerning the probability of a region's antigenicity. Efficient detection systems may include the use of panels of epitopes. The epitopes in the panel may be constructed into one or multiple polypeptides.

In still another embodiment kits suitable for immunodiagnosis and containing the appropriate labeled reagents are constructed by packaging the appropriate materials, including the polypeptides of the invention containing HCV epitopes or antibodies directed against HCV epitopes in suitable containers along with the remaining reagents materials required for the conduct of the assay (e.g., wash buffers, detection means like labeled anti human Ig, labeled anti-HCV, or labeled HCV antigen), as well as a suitable set of assay instructions.

The Indian isolate (AY651061) nucleotide sequence information described herein may be used to gain information about the sequence of the HCV genomes, and for identifying and isolating additional HCV isolates related to this isolate. This information, in turn, can lead to additional polynucleotide probes, polypeptides derived from the HCV genome, and antibodies directed against HCV epitopes which would be useful for the diagnosis and/or treatment of HCV caused NANB Hepatitis.

The current standard-of-care therapy for chronically infected HCV patients is a combination of pegylated IFN and ribavirin, which is costly, lengthy (6-12 months), associated with significant side effects and results in sustained viral response in only 50% of patients. In patients infected with genotype 1, the most common form, response rates are even lower. With an estimated 170 million HCV carriers worldwide, it is clearly important to develop better therapeutic options. With our increasing knowledge of the virus encoded enzymes and genetic elements vital to the life-cycle of HCV, much attention is now being focused on the development of HCV protease, replicase, helicase, antisense, silencing RNA and other specific inhibitors. However, preliminary data have directly linked responses to IFN-a and ribavirin with pretreatment titers of viral antibodies (presumed to be against the envelope glycoproteins), peripheral $T_H$ cell responses to the HCY core and other antigens, as well as to intrahepatic CDS+ CTL responses to the virus. Total pretreatment CDS+T-cell counts in the liver have also been correlated with sustained responses to standard-of-care therapy. Therefore, it may be possible to boost such immune responses in patients by appropriate vaccination and thereby improve the response rate to the standard-of-care therapy. Such immunotherapy may also help control the emergence of escape mutants that would be predicted to arise from any future use of HCV protease or replicase inhibitors, for example, given the extreme fluidity and heterogeneity of the HCV genome.

In still another embodiment provides many therapeutic vaccine trials are planned or are already in progress and use diverse delivery methods and formulations but little information is available about their efficacy at present. What is known, however, is that use of an alum-adjuvanted recombinant gpE1 antigen was able to boost humoral and cellular immune responses to gpE1 in viraemic patients, providing encouragement that vaccination can increase immune responses in pre-existing carriers. It remains to be seen whether boosting viral-neutralizing antibody titres or broad CD4+$T_H$ responses or broad CDS"I-cell responses will have the greatest impact on reducing viral load and in the response to antiviral therapy. But, as may be the case for optimal prophylaxis, boosting of these immune responses may be ideal for immunotherapy.

In still another embodiment the general techniques used in extracting the genome from a virus preparing and probing a cDNA library, sequencing clones. constructing expression vectors, transforming cells, performing immunological assays such as radioimmunoassays and ELISA assays, for growing cells in culture, and the like are known in the art and laboratory manuals are available describing these techniques. However, as a general guide the following sets forth some sources currently available for such procedures. and for materials useful in carrying them out.

In still another embodiment both prokaryotic and eukaryotic host cells may be used for expression of desired coding sequences when appropriate control sequences which are compatible with the designated host are used. Among prokaryotic hosts, *E. coli* is most frequently used. Transfer vectors compatible with prokaryotic hosts are commonly derived from, for example, pBA322, a plasmid containing operons conferring ampicillin and tetracycline resistance, and the various pUC vectors, which also contain sequences conferring antibiotic resistance markers. These markers may be used to obtain successful transform ants by selection. The foregoing systems are particularly compatible with *E. coli*; if desired, other prokaryotic hosts such as strains of *Bacillus* or *Pseudomonas* may be used, with corresponding control sequences.

In still another embodiment a vector construction employs techniques which are known in the art. Site-specific DNA cleavage is performed by treating with suitable restriction enzymes under conditions which generally are specified by the manufacturer of these commercially available enzymes. The cleaved fragments may be separated using polyacrylamide or agarose gel electrophoresis techniques, according to the general procedures found in Methods in Enzymology (1980) 65:499-560. Sticky ended cleavage fragments may be blunt ended using *E. coli* DNA polymerase I (Klenowfln) in the presence of the appropriate deoxynucleotide triphosphates (dNTPS) present in the mixture. Treatment with S1 nuclease may also be used, resulting in the hydrolysis of any single stranded DNA portions.

In still another embodiment, ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation. Ligation mixtures are transformed into suitable cloning posts. such as *E. coli*, and successful transform ants selected by, for example, antibiotic resistance, and screened for the correct construction.

In still another embodiment the present invention describes the cloning of the Indian isolate (AY651061) nucleotide sequences. Blood sample was used as a source of HCV virions was found to be positive in an anti HCV antibody assay. The HCV isolate from these samples were named Indian isolate (AY651061). The infectivity of the blood sample containing the Indian isolate (AY651061) isolate was confirmed by a prospective study of blood transfusion recipients. Dr. C. M. Habibullah from the Department of Gastroenterology at Owaisi Hospital, Hyderabad, India collected blood from patients who have contracted post-transfusion non-A, non-B hepatitis. He also collected blood samples from the respective blood donors of these patients. Next, these samples were assayed for antibodies to the 3$^{rd}$ EIA and blood from one of the donors was found to be positive.

In still another embodiment, isolation of the RNA from the blood samples began by pelleting virions in the blood sample by ultracentrifugation [Bradley, O W, McCaustland, K. A., Cook E. H., Schable C. A., Ebert. J W. and Maynard, J. E. (1985) Gastroenterology 88, 773-779]. RNA was then extracted from the pellet by the guanidinium/cesium chloride method [Maniatis T., Fritsch, E. F., and Sambrook J. (1982) “Molecular Cloning: A Laboratory Manual”, Cold Spring Harbor Laboratory. Cold Spring Harbor] and further purified by 35 phenol/chloroform extraction in the presence of urea,

[Berk. A. J. Lee. F. Harrison, T. Williams, J. and Sharp, P. A. (1979) Cell 17, 935-944]. Eleven pairs of Synthetic oligonucleotide primers were designed from the 5'UTR, C, E1, E2, P7, NS2, NS3, NS4 and N55 domains of the nucleotide sequence of Indian isolate (AY651061) to isolate fragments from AY051292 and HCV-1 genome. The first set of primers was to isolate the sequence from the 5'UTR and a bit of core, the second set was core, third set envelope domain, fourth set envelope domain, fifth set of primers were to isolate a fragment which overlapped the putative envelope and non-structural one, NS1 domains, sixth set was NS2 domain, seventh set of primers was NS3, eighth set of primers was NS4, ninth set of primers was NS5A, tenth set of primers was a part of NS5B, eleventh set of primers was a part of NS5B and 3'UTR. The sequences for the various primers are shown in FIG. 27.

In still another embodiment, about 1 μg of the anti-sense primers was added to 10 units of reverse transcriptase (Promega) to synthesize cDNA fragments from the isolated RNA as the template. The cDNA fragments were then amplified by a standard polymerase chain reaction [Saiki, R. K., Scharf, S., Faloona, F., Mullis, K. B., Horn G. T., Erlich, H. A., and Arnheim, N. (1985) Science 230, 1350-1354]—after 1 μg of the appropriate sense primers was added. The cDNA fragments amplified by the PCR method were gel isolated and cloned pGMT EASSY vector. Clones which contain the fragments of the viral domains were successfully constructed. From the PCR reaction of the Indian isolate (AY651061), three independent clones from each region, C/E, E, E1NS1, NS3, and NS5, have been sequenced by the dideoxy chain termination method. Sequence from all regions has been isolated from the Indian isolate (AY651061). However, there is heterogeneity between clones containing sequence from the same region. Consequently, a consensus sequence was constructed for each of the domains. These differences may be explained as artifacts which occur randomly during the PCR amplification [Saiki, R. K., Scharf, S., Faloona, F., Mullis, K. B., Horn, G. T., Erlich, H A, and Arnheim, N. (1985) Science 230, 1350-1354]. Another explanation is that more than one virus genome is present in the plasma of a single healthy carrier and that these genomes are heterogeneous at the nucleotide level.

In still another embodiment, it was determined how many of these nucleotide differences would lead to amino acid changes, using the sequence from the NS3 domain of the HCV 1 isolate as an example. Out of the five nucleotide differences, three fall on the third position' of the amino acid codon and do not change the amino acid sequence. Both of the remaining two nucleotide changes fall on the first position of the amino acid codon and generate amino acid changes of threonine to alanine and proline to alanine all of which are small, neutral amino acid residues. Similarly, when analyzing the nucleotide differences in other domains, many silent and conserved mutations are found. These results suggest that nucleotide sequences of the HCV genomes in the plasma of a single healthy donor are heterogeneous at the nucleotide level. In addition, once the consensus sequences for each of the fragments were compiled each sequence was compared to the HCV 1 isolate in FIGS. 11 through 19. The invention is further elaborated with the help of following example(s). However, these example(s) should not be construed to limit the scope of the invention.

EXAMPLE: 1

Selection and HCV RNA Isolation from HCV Infected Patient

A single chronic Hepatitis C virus infected patient was selected for sequence and characterization of complete genome of hepatitis C virus. Twenty ml of intravenous blood was collected and serum was separated and stored at −70° C.

HCV RNA isolation: HCV RNA was isolated from the serum by the guanidinium isothicynate (GITC) acid-phenol method (Chomeczynski and Saachi 1987).

200 μl of serum was mixed with 500 μl lysis buffer (4M GITC, 0.75 M Sodium acetate, 0.5% Sarkosyl, 0.1M β-meracapto ethanol), 50 μl of 3M sodium acetate (Ph 5.2), 500 μl water saturated phenol and 200 μl cholorofrom: Iso amyl alcohol (24:1 v/v).

The tubes were vortexed in each step and finally kept in ice for 15 min. The tubes were centrifuged at 12000 rpm for 30 min in refrigerated centrifuge.

The aqueous phase (approx. 500 μl) was collected very carefully, mixed with equal volume of isopropanol and kept at −70° C. over night.

The over night kept solutions were centrifuged at 12000 rpm for 30 min at 4° C. and pellets were washed with 1 ml of 70% ethanol. The tubes were dried in heat block at 55° C. for 10 min and each pellet was re-suspended in 20 μl DEPC treated water.

Many sets of primers were designed to construct cDNA followed by PCR.

(The list of primers is attached (SEQ ID NOS: 19-40)).

EXAMPLE: 2 cDNA Synthesis cDNA synthesis was carried out by adding 6 μl of the isolated HCV RNA to a final 20 μl of reaction mix composed of 40 picomoles of reverse primer, 4 μl of 5× reverse transcriptase buffer, 1 μl of 10 mM dNTPs, 7 μl of DEPC-treated water, 100 U of reverse transcriptase (MMLV supplied by promega). The mixture was incubated at 42° C. for 60 min. The reaction was terminated by heating at 70° C. for 15 min, and then chilled the mixture on ice.

Polymerase Chain Reaction:

For amplification by PCR, a 50 μl mixture containing 10 μl of the c DNA, 1×PCR buffer, 1 μl 10 mM dNTPs, 1.5 μl MgCl2, 2 U Taq polymerase and 1 μl of each forward and reverse primers was denatured at 95° C. for 3 minutes and amplified for 36 cycles under the following conditions: 94° C. for 1 minutes (denaturation), 54° C. for 1.5 minutes (annealing), and 72° C. for 2 minutes (extension), followed by a final extension at 72° C. for 5 minutes. PCR products were analyzed on 2% agarose gels followed by staining with ethidium bromide and visualized under a UV illuminator. A 100 bp ladder (Promega, Madison, Wis.) was used as a size marker.

The PCR product was purified by Quiagen PCR clean up kit as per the protocol described by the supplier (Quiagen, Germany).

EXAMPLE: 3

Cloning of the PCR Product

The purified PCR product was ligated with pGEM-T easy vector. The ligation mix included 2× rapid ligation buffer, T4 DNA ligase (3 Weiss units/μl), PCR product and the final reaction volume made upto 10 μl with deionized water. The reaction mixture was incubated at 16° C. overnight.

Competent cells were prepared by picking a single bacterial colony from a plate that has been incubated for 16-20 hours at 37° C. Transfer the colony into 100 ml of LB broth in a 1 liter flask. Incubate the culture for 3 hours at 37° C. with vigorous agitation, monitoring the growth of the culture. As a guideline, 1 $OD_{600}$ of a culture of *E. coli* strain TOP 10 F' contains ~$10^9$ bacteria/ml. Transfer the bacterial cells to sterile, disposable, ice-cold 50 ml polypropylene tubes. Cool the cultures to 0° C. by storing the tube on ice for 10 minutes. Recover the cells by centrifugation at 5000 rpm for 10 minutes at 4° C. Decant the medium from the cell pellets. Stand the tubes in an inverted position on a pad of paper towels for 1 minute to allow the last traces of media to drain away. Resuspend each pellet by swirling or gentle vortexing in 30 ml of ice-cold $CaCl_2$ ($CaCl_2.2H_2O$ (1M )) solution and kept on ice for one hour. Recover the cells by centrifugation at 5000 rpm for 10 minutes at 4° C. Decant the medium from the cell pellets. Stand the tubes in an inverted position on a pad of paper towels for 1 minute to allow the last traces of media to drain away. Resuspend the pellet by swirling or gentle vortexing in 2 ml of ice-cold 0.1 M $CaCl_2$ for each 50 ml of original culture. At this point, either use the cells directly for transformation or dispense into aliquots contain each 200 μl and freeze at −70° C. To transform the $CaCl_2$—treated cells, thaw cells on ice for 15 minutes. Add DNA (no more than 50 ng in a volume of 10 μl or less) to each tube. Mix the contents of the tube by swirling gently. Store the tubes on ice for 30 minutes. Transfer the tubes to a rack placed in a preheated 42° C. circulating water bath. Store the tubes in the rack for exactly 90 seconds. Do not shake the tube. Rapidly transfer the tubes to an ice bath. Allow the cells to chill for 1-2 minutes. Add 800 μl of LB medium to each tube. Incubate the cultures for 45 minutes in a water bath set at 37° C. to allow the bacteria to recover and to express the antibiotic resistance markers encoded by the plasmid. Recover the cells by centrifugation at 5000 rpm for 5 minutes, resuspend each pellet by swirling or gentle vortexing in 100 μl of LB medium, IM IPTG and X-gal for blue white screening. Transfer the appropriate volume of transformed competent cells on LB agar medium containing the appropriate antibiotic. Store the plates at room temperature until the liquid has been absorbed. Invert the plates and incubate at 37° C. Transformed colonies should appear in 12-16 hours. Remove the plates from the incubator and store them for several hours at 4° C. to allow blue color to develop. Identify colonies carrying recombinant plasmids, colonies that carry wild-type plasmids contain active β-Galactosidase. These colonies are pale blue in the center and dense blue at their periphery. Colonies that carry recombinant plasmids do not contain active β-Galactosidase. These colonies are creamy white or eggshell blue, sometimes with a faint blue spot in the center. Select and culture colonies carrying recombinant plasmids.

Plasmid DNA was prepared by Alkaline Lysis method. Inoculate 5 ml of LB medium containing the appropriate antibiotic with a single colony of transformed bacteria. Incubate the culture overnight at 37° C. with vigorous shaking. Pour 1.5 ml of the culture into a microfuge tube. Centrifuge at maximum speed for 30 seconds at 4° C. in a microfuge. Store the unused portion of the original culture at 4° C. When centrifugation is complete, remove the medium by aspiration, leaving the bacterial pellet as dry as possible. Resuspend the bacterial pellet in 100 μl of ice-cold Alkaline Lysis Solution 1 (50 mM glucose, 25 mM Tris-Cl (pH 8.0), 10 mM EDTA (pH 8.0)) by vigorous vortexing. Add 200 μl of freshly prepared Alkaline Lysis Solution II (0.2N NaOH, 1% (w/v) SDS) to each bacterial suspension. Close the tube tightly, and mix the contents by inverting the tube rapidly five times. Do not vortex! Store the tube on ice. Add 150 μl of ice-cold Alkaline Lysis Solution III. Close the tube and disperse Alkaline Lysis Solution III (5M potassium acetate, glacial acetic acid) through the viscous bacterial lysate by inverting the tube several times. Store the tube on ice for 3-5 minutes. Centrifuge the bacterial lysate at maximum speed for 5 minutes at 4° C. in a microfuge. Transfer the supernatant to a fresh tube. Add an equal volume of phenol:chloroform. Mix organic and aqueous phases by vortexing and then centrifuge the emulsion at maximum speed for 2 minutes at 4° C. in a microfuge. Transfer the aqueous upper layer to a fresh tube. Precipitate nucleic acids from the supernatant by adding 2 volumes of ethanol at room temperature. Mix the solution by vortexing and then allow the mixture to stand for 2 minutes at room temperature. Collect the precipitated nucleic acids by centrifugation at maximum speed for 5 minutes at 4° C. in a microfuge. Remove the supernatant by gently standing the tube in an inverted position on a paper towel to allow all of the fluid to drain away. Add 1 ml of 70% ethanol to the pellet and invert the closed tube several times. Recover the DNA by centrifugation at maximum speed for 2 minutes at 4° C. in a microfuge. Again remove all of the supernatant by gently and store the open tube at room temperature until the ethanol has evaporated and no fluid is visible in the tube (5-10 minutes). Dissolve the nucleic acids in 50 μl of TE (pH 8.0). Vortex the solution gently for a few seconds. Store the DNA solution at −20° C. All the clones were digested with EcoRI to excise the fragment and were checked on the gel for confirmation analysis. The gel picture shows us the results of the clones of all AY651061.

Detection of antibody to HCV has become the principal method for the diagnosis of HCV infection in individuals with chronic hepatitis and for the screening of blood donors. The original assay based upon the recombinant proteins derived from NS4 showed non-specificity and insensitivity, the more recently developed assays that use recombinant proteins from the core and NS3 regions of the HCV genome (second generation) and the NS5 region of the HCV genome (third generation) have proved to be more effective.

HCV can be classified into at least into six major genotypes, whose nucleotide and inferred amino acid sequences over the whole genome differ by approximately 30%. Significant antigenic differences have been documented and form the basis of their classification into serotypes. We wanted to measure serological reactivities to the individual component antigens core, NS3, NS4 and NS5. ORF of Hepatitis C virus whole genome (9441 base pairs) is shown in FIG. 1.

The entire genome of Hepatitis C virus genotype predominant in India was cloned, sequenced and submitted to GenBank (Accession Number AY651061). DNA fragments of all the four antigens viz., Core, NS3, NS4 and NS5 used in the $3^{rd}$ generation diagnostic kits were cloned into pET21 vectors and expressed in *E. coli* BL21 (DE3) strain.

EXAMPLE: 4

Core

Figure 2:
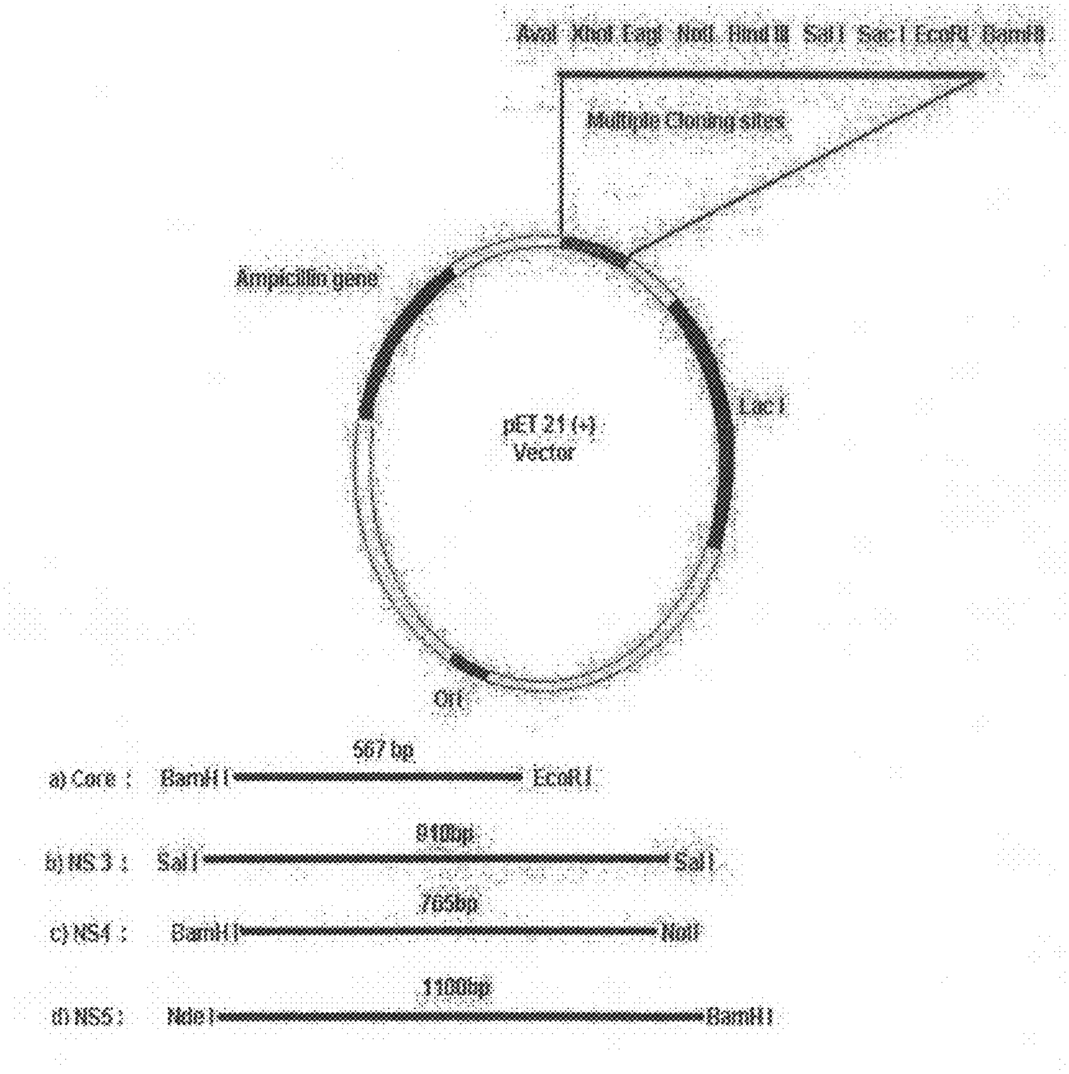
FIG. 2: Hepatitis C virus isolate AY651061 restriction enzyme map.

Cloning and Characterization: The sequencing encoding the core protein is highly conserved among all the Hepatitis C viral subtypes and is localized to nucleotides 342 to 915. The corresponding protein has 191 amino acids and with a molecular weight of about 22 kDa. The coding sequence of core was amplified by Polymerase Chain Reaction (PCR) using gene specific primers. The forward primer contains a BamH1 site and the reverse primer contains an EcoRI site. The amplified 567 bp DNA fragment was then inserted between the BamHI and EcoRI sites of the expression vector pET21a (FIG. 2*a*). This DNA was transferred in to *E. coli* BL21(DE3) cells and individual clones expressing high levels of core were selected. The core sequence was confirmed by sequencing.

Figure 3:
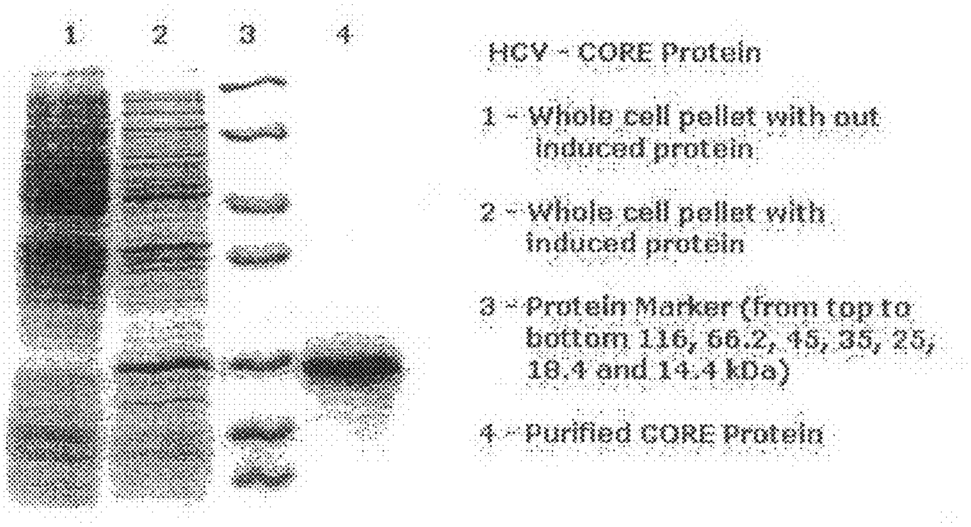
FIG. 3: Photograph of the SDS PAGE gel for the core protein of HCV isolate AY651061.
Figure 4:
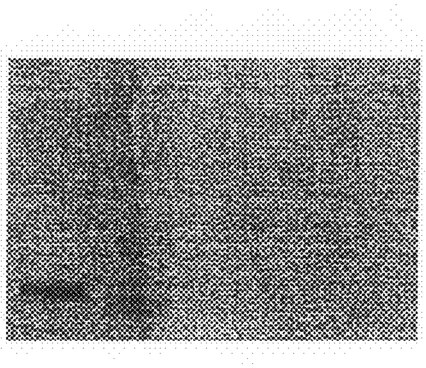
FIG. 4: Photograph of the Western Blot analysis showing the presence of the core protein of HCV isolate AY651061.

Protein purification: *E. coli* cells expressing core were induced by isopropyl-thiogalactoside (IPTG) and pelleted by centrifugation. The pellet was resuspended in lysis buffer and the inclusion bodies were isolated as described (Sambrook et al., 2001). Following solubilization of inclusion bodies with detergents, the protein was purified to homogeneity either by preparative electro-elution or ion exchange chromatography. Purity of the protein was assessed by SDS-polyacrylamide gel electrophoresis (PAGE) (FIG. 3) SDS PAGE gel for the core protein, and a western blot picture of Core protein is shown in FIG. 4.

EXAMPLE: 5

NS3

Cloning and Characterization: The DNA sequence encoding the NS4 region (nucleotides 5246 to 6015; SEQ ID NO: 1) was amplified by PCR using the gene specific forward and reverse primers. Thus amplified 765 bp DNA is digested with BamHI and NotI at 5' and 3' ends respectively and inserted into the BamHI and NotI sites in pET21a (+) vector (FIG. 2*c*) and transferred into *E. coli* BL21 (DE3) cells. The clone expressing highest levels of NS4 was selected and the DNA was sequenced. It should be pointed out that in this clone about of 83 amino acids at the COOH-end was missing. Subsequently we cloned this additional sequence also to give to produce full-length protein (~305 amino acids (SEQ ID NO: 16)). It should be pointed out that both truncated and the full-length proteins are equally efficient in detecting positive patients' sera.

Figure 5:
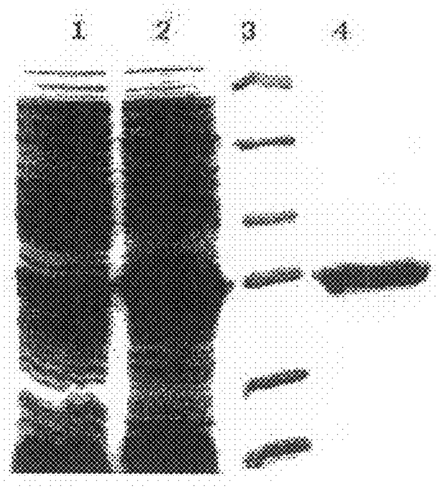
FIG. 5: Photograph of the SDS PAGE gel for the NS3 protein of HCV isolate AY651061.

Protein Purification: The bacterial clone carrying NS3 gene was induced by IPTG, collected cells by centrifugation and inclusion bodies were prepared as described for Core. Following solubilization of inclusion bodies the protein was purified to homogeneity either by preparative gel electro-elution or ion exchange chromatography. Purity of NS3 protein was checked by SDS-PAGE (FIG. 5).

EXAMPLE: 6

NS4

Cloning and Characterization: The DNA sequence encoding the NS4 region (nucleotides 5246 to 6015) was amplified by PCR using the gene specific forward and reverse primers. Thus amplified 765 bp DNA is digested with BamHI and NotI at 5' and 3' ends respectively and inserted into the BamH I and NotI sites in pET21a (+) vector (FIG. 2*c*) and transferred into *E. coli* BL21(DE3) cells. The clone expressing highest levels of NS4 was selected and the DNA was sequenced. It should be pointed out that in this clone about of 83 amino acids at the COOH-end was missing. Subsequently we cloned this additional sequence also to give to produce full length protein (~305 amino acids). It should be pointed out that both truncated and the full length proteins are equally efficient in detecting positive patients' sera.

Figure 6:
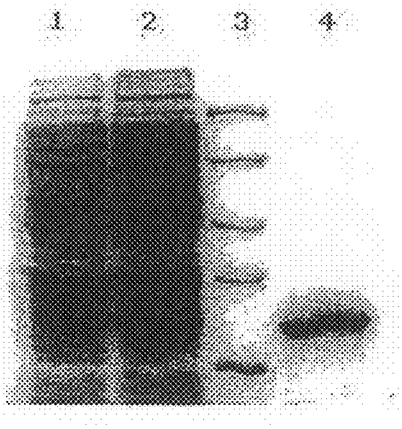
FIG. 6: Photograph of the SDS PAGE gel for the NS4 protein of HCV isolate AY651061.

Protein purification: Standard purification protocol described above for Core and NS3 was used to purify NS4 to homogeneity which was verified by SDS-PAGE (FIG. 6)

EXAMPLE: 7

NS5: Cloning and Characterization

The NS5A region extends from nucleotides 6281 to 7403 (SEQ ID NO: 1) (374 amino acids; SEQ ID NO: 2) and mass of about 45 kDa. The region was amplified by PCR using the gene specific primers containing NdeI and BamHI sites in the forward and reverse primers, respectively. The amplified 1100 bp DNA was digested with NdeI and BamHI and inserted at the NdeI and BamHI sites of pET21a (+) vector (FIG. 2*d*), which was then transferred into *E. coli* BL21(DE3) cells. The bacterial clone carrying the NS5 gene was confirmed by DNA sequencing.

Figure 7:
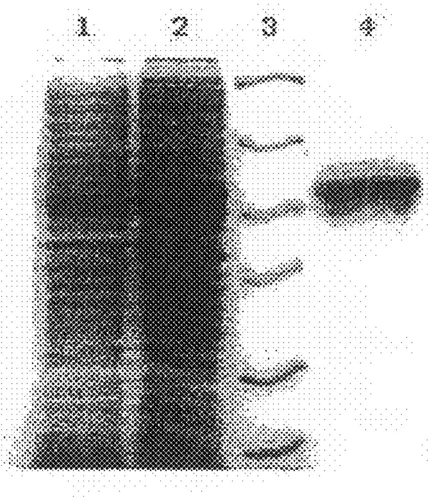
FIG. 7: Photograph of the SDS PAGE gel for the NS5 protein of HCV isolate AY651061.
Figure 8:
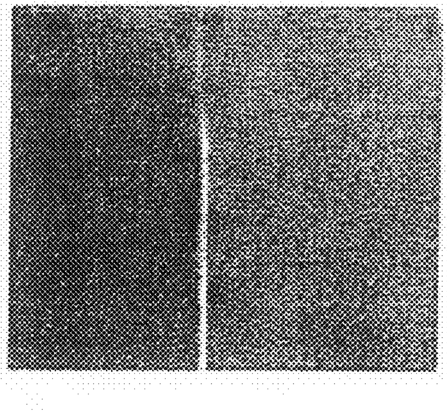
FIG. 8: Photograph of the Western blot analysis showing the presence of the NS5 protein of HCV isolate AY651061.

Protein purification: Induction, isolation of inclusion bodies and solubilization were as described for Core and NS3. Purity was checked by SDS-PAGE (FIG. 7). SDS-PAGE gel for the NS5 protein, Western blot analysis showing the presence of the NS5 protein is shown in FIG. 8.

Results

A total number of 532 patients were screened for HCV infection. A total of 218 patients were found to be positive by RT-PCR. Among the 218 samples, 211 were positive by $3^{rd}$ EIA where as all the 218 were positive by the Core, NS3, NS4, NS5 proteins derived from our Indian isolate (AY651061). Further competitive analysis for each antigen showed the following results:

About 98 samples were positive by all the four proteins and 38 samples were reactive with core, NS3, NS4, but were not picked by NS5. Similarly, 29 samples were not detected by NS4 and NS5 and 12 samples were not detected by core protein EIA. 10 samples were not picked by NS5 and Core, 16 samples were not picked by NS4, 8 samples were not picked by NS4 and core.

The interesting observation of the present analysis was that 7 samples were not picked by $3^{rd}$ EIA but were picked by our purified proteins. A total of 4 samples were picked by core and NS3, 2 samples were picked by core, NS3 and NS4, and 1 sample was picked by core. About 315 samples were negative by all the methods that were used.

| Core | NS3 | NS4 | NS5 | Total No. Samples | RT-PCR | Abbott $3^{rd}$ EIA |
|---|---|---|---|---|---|---|
| + | + | + | + | 98 | + | + |
| + | + | + | − | 38 | + | + |
| + | + | − | − | 29 | + | + |
| − | + | + | + | 12 | + | + |
| − | + | + | − | 10 | + | + |
| + | + | − | + | 16 | + | + |
| − | + | − | + | 08 | + | + |

-continued

| Core | NS3 | NS4 | NS5 | Total No. Samples | RT-PCR | Abbott $3^{rd}$ EIA |
|---|---|---|---|---|---|---|
| + | + | − | − | 04 | + | − |
| + | + | + | − | 02 | + | − |
| + | − | − | − | 01 | + | − |
| − | − | − | − | 314 | − | − |
| | | | | 532 | | |

The findings of significant antigenic variability of antigens used for serological screening will form the basis for a number of future investigations. It will be possible to carryout screening of our population infected with genotype 1. This may reveal the frequency with which anti-HCV samples are being missed therefore, assays developed from purified proteins from our isolate may be more effective for the detection of antibody elicited by infection with a specific genotype that is more prevalent.

Our recent progress on HCV gave us a lot of new information on the genetic variation of the strains floating in Indian population. This will provide the basis for developing an effective vaccine.

EXAMPLE: 8

Transformation

About 10 μl of ligation mixture was added to the competent *E. coli* Top10F' cells and incubated on ice for 20 minutes. Following a 90 sec incubation at 42° C., 1000 μl of LB medium was added to the tube and incubated for 45 min at 37° C. Cells were centrifuged at 5000 rpm for 5 min, dissolved the pellet in 100 μl LB medium and plated on a LB plate with appropriate antibiotic and IPTG/X-gal. Plates were incubated overnight at 37° C. Colonies and selected and grown in a 5 ml LB broth overnight at 37° C. with shaking. DNA was isolated from a 1.5 ml culture in 1.5 ml Eppendoff using Quiagen plasmid DNA kit. After plasmid DNA isolation, DNA was digested with EcoRI enzyme to check the insert and the DNA was sent for sequencing.

EXAMPLE: 9

DNA Sequencing

The cloned HCV sequences were amplified using M13 primers both forward and reverse. The re-amplified PCR products were sequenced by the direct sequencing method in an automated sequencer (Applied Biosystems, Inc., Foster City, Calif., USA). Sequences of all clones of the HCV genome were analyzed and checked with NCBI Blast software program. All the sequences from different clones of the HCV genome were joined using CHROMAS and CHROMAS-PRO software programs. This complete Indian isolate of the HCV genome was submitted to GenBank.

EXAMPLE: 10

Comparative Analysis of New Isolate (Indian Strain: AY 651061) with the Prototype HCV1

The HCV genome organized into several regions which code for various viral proteins-5' untranslated region (UTR), core gene, genes for two envelope glycoproteins (E1 & E2/NS1) genes for seven nonstructural proteins (NS2, NS3A, NS3B, NS4A, NS4B, NS5A & NS5B) and 3'UTR. The nucleotide comparison of various viral proteins are shown in FIG. 11 to FIG. 19, and amino acid comparison with various viral proteins are shown in FIG. 20 to FIG. 26.

The complete genome of new Indian isolate shows 82.9% nucleotide homology with prototype HCV1 strain.

The 5'UTR is highly conserved among all the strains, 99.1% nucleotide homology was observed in new Indian isolate compared HCV1.

The new Indian isolate of HCV Core gene was showing 97.6% nucleotide homology compared with prototype HCV1.

The new Indian isolate of HCV E1 gene was showing 80.8% nucleotide homology compared with prototype HCV1.

The new Indian isolate of HCV E2/NS1 gene was showing 84.7% nucleotide homology compared with prototype HCV1.

The new Indian isolate of HCV NS2 gene was showing 81.9% nucleotide homology compared with prototype HCV1.

The new Indian isolate of HCV NS3 gene was showing 82.4% nucleotide homology compared with prototype HCV1.

The new Indian isolate of HCV NS4 gene was showing 79.3% nucleotide homology compared with prototype HCV1.

The new Indian isolate of HCV NS5 gene was showing 80% nucleotide homology compared with prototype HCV1.

The new Indian isolate of HCV 3'UTR gene was showing 81.5% nucleotide homology compared with prototype HCV.

The complete genome of new Indian isolate shows 86.3% amino acid homology with prototype HCV1 strain.

The new Indian isolate of HCV Core gene was showing 98.4% amino acid homology compared with prototype HCV1.

The new Indian isolate of HCV E1 gene was showing 80.5% amino acid homology compared with prototype HCV1.

The new Indian isolate of HCV E2/NS1 gene was showing 86.2% amino acid homology compared with prototype HCV1.

The new Indian isolate of HCV NS2 gene was showing 80.7% amino acid homology compared with prototype HCV1.

The new Indian isolate of HCV NS3 gene was showing 91.4% amino acid homology compared with prototype HCV1.

The new Indian isolate of HCV NS4 gene was showing 87% amino acid homology compared with prototype HCV1.

The new Indian isolate of HCV NS5 gene was showing 83.1% amino acid homology compared with prototype HCV1.

What is claimed is:

1. An isolated hepatitis C virus polynucleotide sequence comprising SEQ ID NO:1.

2. The isolated hepatitis C virus polynucleotide sequence as claimed in claim 1, wherein said sequence is isolated from Indian patient pool. 3. An isolated polynucleotide sequence comprising SEQ ID NO:3, SEQ ID NO:4, SEQ ID NO:5, SEQ ID NO:7, SEQ ID NO:9, SEQ ID NO:11, SEQ ID NO:13, SEQ ID NO:15, or SEQ ID NO:17 encoding 5' untranslated region (UTR), 3' untranslated region (UTR), Core protein, Envelope glycoprotein (E1), Envelop glycoprotein (E2)/Non-structural protein NS1, Non-structural protein NS2, Non-structural protein NS3, Non-structural protein NS4 and Non-structural protein NS5 respectively.

4. A pair of primers comprising sequences consisting of SEQ ID NOs: 19 and 20 for amplification of SEQ ID NO:3; SEQ ID NOs:21 and 22 for amplification of SEQ ID NO:5; SEQ ID NOs:23 and 24 for amplification of SEQ ID NO:7; SEQ ID NOs:25 and 26 for amplification of SEQ ID NO:7 and SEQ ID NO:9; SEQ ID NOs:27 and 28 for amplification of SEQ ID NO:9; SEQ ID NOs:29 and 30 for amplification of SEQ ID NO:11 and SEQ ID NO:13; SEQ ID NOs:31 and 32 for amplification of SEQ ID NO:13; SEQ ID NOs:33 and 34 for amplification SEQ ID NO:15; SEQ ID NOs:35 and 36 for amplification of SEQ ID NO:17; SEQ ID NOs:37 and 38 for amplification of SEQ ID NO:17; or SEQ ID NOs:39 and 40 for amplification of SEQ ID NO:17 and SEQ ID NO:4.

5. An *E. coil* strain TOP10F'HCV-AY651061 having accession No. MTCC 5350, deposited at Microbial Type Culture Collection and Gene Bank (MTCC), Chandigarh, India.

* * * * *

SEQUENCE LISTING

<160> NUMBER OF SEQ ID NOS: 56

<210> SEQ ID NO 1
<211> LENGTH: 9441
<212> TYPE: DNA
<213> ORGANISM: Hepatitis C virus

<400> SEQUENCE: 1

```
gccagccccc tgatgggggc gacactccgc catgaatcac tcccctgtga ggaactactg     60
tcttcacgca gaaagcgtct agccatggcg ttagtatgag tgtcgtgcag cctccaggac    120
ccccccctccc gggagagcca tagtggtctg cggaaccggt gagtacaccg gaattgccag    180
gacgaccggg tcctttcttg gataaacccg ctcaacgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggacagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtacccttgg cccctctatg    600
gcaatgaggg ctgcgggtgg gcgggatggc tcctgtctcc ccgcggctct cggcctagtt    660
ggggccccac agacccccgg cgtagatcgc gcaatttggg taaggtcatc gataccctta    720
cgtatggctt cgccgacctc atggggtaca taccgctcgt cggcgccccc cttgggggcg    780
ctgccagggc cctggcgcac ggcgtccggg tcctggaaga cggcgtgaac tatgcaacag    840
ggaaccttcc tggttgctct ttctctatct tccttctggc cctgctctct tgcttgactg    900
tgcccgcttc ggccgtcgga gtgcgcaact cttcgggggt gtaccatgtc accaatgatt    960
gccccaatgc gtctgttgtg tacgagacag atagcttgat catacatctg ccggggtgtg   1020
tgccctgcgt acgcgagggc aacggttcga ggtgctgggt ctcccttagt cctactgttg   1080
ccgctaagga tccgggcgtc ccggtcaacg agattcggcg tcacgtcgac ctgattgccg   1140
gggccgctgc attctgttcg gctatgtatg tagggcactt atgcggttcc atcttcctcg   1200
ttggccagct tttcaccctc tcccctaggc gccactggac aacacaagac tgtaattgct   1260
ccatctaccc aggacatgtg acaggccatc gaatggcttg ggacatgatg atgaactggt   1320
cccctacgac ggcgctggta gtagcccagc tgctccggat cccacaagcc atcttggaca   1380
tgatcgctgg tgctcactgg ggagtcctgg cgggcatagc gtatttctcc atggtgggga   1440
actggacgaa ggtcctggta gtgctgctgc tatttgccgg cgtcgacgcg acgaccatcg   1500
tctccggggg aagtgccggc cgcagcacgg ctggacttgt tgggctcttc tcaccaggcg   1560
cccggcagaa catccagctg atcaacacca acggcagttg gcacatcaac cgcacggccc   1620
tgaactgcaa tgataccctt caaaccggct gggtagcagg gcttttctat accaacaaat   1680
tcaactcttc gggttgcccc gagaggttgg ccagctgccg accccttgcc gactttgacc   1740
agggctgggg ccctatcagt tataccaacg gaagcggccc cgaccaacgc ccctactgct   1800
ggcactaccc cccaaaacct tgtggtattg tgcccgcaga gagcgtgtgt ggcccagtat   1860
actgcttcac tcccagcccc gtggtggtgg gaacgaccga caggtcgggc gcgcccacct   1920
acaactgggg tgaaaatgaa acggacgttt tcgtcctcaa caacaccagg ccacggctgg   1980
gcaattggtt cggtggtacc tggatgaact caactggatt caccaaggtg tgcggagcgc   2040
```

-continued

```
ccccttgtgc catcggaggg gtgggcaaca acaccttgta ctgccccact gattgtttcc   2100
gcaaacatcc ggaagccacg tactctcggt gcggctccgg tccttggatt acacccaggt   2160
gcttgatcca ctacccgtat aggctttggc attatccttg taccatcaat tacaccatat   2220
tcaagatcag gatgtttgtg ggcggggttg agcacaggct cgacgccgcg tgcaactgga   2280
cgcggggaga gcgctgcgac ttggacgaca gggatcgggc cgagttgagc cctctgttgc   2340
tgtccactac gcaatggcag gtcctcccct gctcattcac aacactgccc gccctgtcaa   2400
ctggcctgat acatctccac cagaacatcg tggacgtgca gtacctctat gggttgagct   2460
cggcagtcac atcctgggtc ataaagtggg agtacgttgt gctcctcttc ttgctgctag   2520
cagatgctcg catttgtgcc tgcttgtgga tgatgcttct catatctcag gtagaggcgg   2580
cgctggagaa cttgatagtt ctcaacgctg cttccctagt cgggacacat ggcatcgtcc   2640
ccttcttcat ctttttttgt gcagcttggt acctaaaagg caagtgggcc cctggactcg   2700
cctattccgt ctatgggatg tggccactgc tcctgcttct cctggcgttg ccccaacggg   2760
catacgcctt ggatcaggag ttggccgcgt cgtgtggggc cacggtcttc atctgcctag   2820
cggtgctcac tctatcgcca tattacaaac agtacatggc ccgcggcatc tggtggctgc   2880
agtacatgct gaccagagca gaggcgctcc tacaggtttg ggtcccccg ctcaacgccc   2940
gaggagggcg cgacggagtc gtactgctca cgtgtgtgct ccacccgcac ttgctctttg   3000
aaatcaccaa gatcatgctg gccattctcg ggcctttgtg gatcttgcag gccagtctgc   3060
tcaaggtacc gtacttcgtg cgcgttcagg gccttctccg gatctgcgcg ctagcgcgga   3120
agatggtcgg aggccattac gtgcaaatgg tcaccatcaa gttaggggcg ctcactggca   3180
cctatattta taaccatctc actcctcttc gggactgggc gcacaacggc ttgcaagacc   3240
tagccgtagc tgtggagcca gtcgtcttct cccaaatgga gaccaagctc atcacgtggg   3300
gggcagacac agccgcgtgt ggtgacatca tcaacggctt gcccgtctcc gcccgcaggg   3360
gccaggagat actgctcgga ccagccgatg gaatggcctc taggggatgg aggttgctgg   3420
cgcccatcac ggcgtacgct cagcagacaa ggggcctcct agggtgtata atcaccagcc   3480
tgactggccg ggacaagaac caagtggagg gtgaagtcca gattgtgtca actgctgccc   3540
aaacgttctt ggcgacgtgc atcaacgggg tatgctggac tgtctaccac ggggccggaa   3600
ccaggaccat tgcatcatcc aagggtcctg ttattctaat gtataccaat gtagaccaag   3660
acctcggggg ctggaccgct cctcaagtgc tcggctcact gacaccctgg agctgcggct   3720
cctcggacct ttacctggtc acgaggcatg ccgatgtcat tcccgtgccg cggcgaggtg   3780
aaaccagggg cagcctgctt tcgccccggc ccatttccta tctaaaggga tcctcgggag   3840
gccccctgct ctgtcccatg ggacatgccg tgggcatttt cagggccgcg gtgtgcaccc   3900
gtggggtcgc aaaggcggtc gactttgtgc ccgttgagtc cttagagacc accatgaggt   3960
ccccagtgtt tactgacaat tccagccctc taacagtgcc ccagagttac caggtggcgc   4020
atctacatgc acccactggg agtggcaaga gcacgaaggt gccggccgct tacgcagctc   4080
aggggtacaa ggtacttgtg ctgaacccgt ctgttgctgc caccttaggg ttcggtgctt   4140
atatgtcaaa ggcccatggg atcgacccaa acatcaggac cggcgtgagg accatcacca   4200
caggctcccc catcacctac tccacctacg gcaaattttt ggctgatggc ggatgcccag   4260
gaggtgcgta cgacatcata atatgtgacg aatgtcactc agtggacgcc acctcgattc   4320
tgggcatagg gaccgtcttg gaccaagcgg agacggcggg ggtcaggctc actgtcctcg   4380
```

-continued

```
ccaccgctac accacctggt tccgtcaccg tgccacattc caacatcgag gaagttgcac   4440
tgtccgctga cggggaaata ccattttatg gtaaggccat cccccctaaac tacatcaagg   4500
gggggaggca cctcattttc tgccactcca agaagaagtg cgacgagctc gctgcaaagc   4560
tggtcggtcc gggcgtcaac gcggtggcct tttaccgtgg cctcgacgta tctgtcattc   4620
caactacagg agacgtcgtt gttgtagcga ccgacgcctt gatgactggc ttcaccggag   4680
atttcgactc tgtgatagac tgcaacacct gtgtcgtcca gacagtcgac ttcagcctag   4740
accctatatt ctctattgag acttccaccg tgccccagga cgccgtgtcc cgctcccaac   4800
ggaggggtag gaccggtcga gggaagcatg gtatttacag atatgtgtca cccggggagc   4860
ggccgtctgg catgttcgac tccgtggtcc tctgtgagtg ctatgacgcg ggttgtgctt   4920
ggtacgagct tacacccgcc gagaccacag tcaggctacg ggcatacctc aacaccccag   4980
gattgcccgt gtgccaggac cacttggagt tctgggagag tgtcttcacc ggcctcaccc   5040
acatagatgc ccacttcctg tcccagacga aacagagtgg ggagaacttc ccctacctag   5100
tcgcatacca agccaccgtg tgcgctagag ctagagctcc tcccccgtca tgggaccaaa   5160
tgtggaagtg cctgatacgg ctcaagccca ccctcactgg ggctacccca ttactataca   5220
gactgggtag tgtacagaat gagatcacct taacacaccc aatcacccaa tacatcatgg   5280
cttgcatgtc ggcggacctg gaggtcgtca ctagcacgtg ggtgttggtg ggcggcgtcc   5340
tagccgcttt ggccgcttac tgcctgtcca caggcagcgt ggtcatagtg ggcaggataa   5400
tcctaggtgg gaagccggca gtcatacctg acagggaggt tctctaccga gagtttgatg   5460
agatggagga gtgcgccgcc cacgtcccct acctcgagca ggggatgcat ttggcggagc   5520
agttcaagca gaaagctctt gggttgctcc agacggcatc caaacaaaca gagacgatca   5580
ctcccattgt ccagtctaat tggcagaagc tcgagtcttt ctgggctaaa cacatgtgga   5640
acttcgttag cgggatacaa tatctggcgg gcctatcaac gctgcccggg aaccccgcta   5700
tagcatcgct gatgtcgttt acggccgcag tgacgagtcc actaaccact cagcagaccc   5760
tcctctttaa catcttgggg gggtggctgg ctgcccagct tgccgcccca gccgccgcca   5820
cagccttcgt tggcgcaggc attactggcg ccgttgttgg cagtgtgggc ctagggaagg   5880
tcctggtgga cattcttgcc ggctacgggg ctggtgtggc cggggccctc gtggctttca   5940
aaatcatgag cggggagacc cccaccacgg aggatctagt caaccttctg cctgccatcc   6000
tatcgccagg agctctcgtt gtcgccgtgg tgtgcgcagc aatactacgc cggcacgtgg   6060
gccttggcga gggcgccgtg cagtggatga accggctgat agcgtttgct tctcggggta   6120
accacgtctc ccctacacac tacgtgccgg agagcgacgc gtcggctcgt gtcacaccaa   6180
ttctcaccag gctcactgtt actcagcttc tgaaagggct ccacgtgtgg ataagctcga   6240
attgcatcgc cccgtgtgct agttcttggc ttaaagatgt ctggaactgg atatgcgagg   6300
tgctgagcga cttcaagaat tggctgaagg ccaaacttgt accacaactg cccgggatcc   6360
cattcgtatc ctgccaacgc gggtaccgtg gggtctggcg gggcgagggc atcgtgcaca   6420
ctcgttgccc gtgtggggcc aatataactg gacatgtcaa gaacggttcg atgagaatcg   6480
tcgggcctaa gacttgcagc aacacctggc gtgggtcgtt ccccattaac gcttacacta   6540
caggcccgtg cacgccctcc ccggcgccga actatacgtt cgcgctatgg agggtgtctg   6600
cagaggagta tgtggaggta aggcggctgg gggacttcca ttacgtcacg gggtgacca   6660
ctgataaact caagtgtcca tgccaggtcc cctcacccga gttctccaca gaggtggacg   6720
gggtgcgcct gcataggtac gcccctccct gcaaacccct gctacgggat gaggtgacgt   6780
```

-continued

```
ttagcgtcgg gttcaatgaa tacctggtgg ggtcccagtt gccctgcgag cccgagccag   6840
acgtagcagc attaacatca atgcttacag acccttccca catcactgca aagacggcgg   6900
cgcgtaggct gaagcggggg tctccccct ccctggccag ttcttctgcc agccagctgt   6960
ccgcgccgtc actgaaagca acatgcacca ctcaccatga ctctccagac gccgacctca   7020
tagaagccaa cctcctgtgg agacgggaga tggggggaa catcaccaga gtggagtcgg   7080
agaacaagat tgttgttctg gattctttcg acccgctcgt ggcagaggag gatgaccggg   7140
agatttctat tccagctgag attctgcgga aatttaagca gtttcccccc gccatgccca   7200
tatgggcacg gccggattat aatcctcccc ttgtggaacc gtggaagcgc ccggactgtg   7260
atccaccctt agtccacggg tgcccccta cacctcccaa gccgactccg gtgccgccac   7320
cccggaaaaa gaggacggtg gtgctggacg agtctacagt atcatctgct ctggctgagc   7380
ttgccactaa gaccttcggc agctctacaa cctcaggcgt gacaagtggt gaagcggccg   7440
aatcgtcccc ggcgctttcc tgcgacggtg agctggactc cgaagctgaa tcttactcct   7500
ccatgccccc tctcgagggg gaaccggggg accccgatct cagcgacggg tcttggtcta   7560
ccgtgagcag tgatggcggt acggaggatg tcgtgtgctg ctcgatgtcc tactcgtgga   7620
cgggcgcctt aattacgccc tgtgccgcag aggaaaccaa actccccatc aacgcactga   7680
gtaactcgct gctgcgccac cacaatttgg tgtattccac cacctctcgc agcgctggca   7740
agaggcagaa aaaagtcaca tttgacaggc tgcaggtcct ggacgatcat taccgggacg   7800
tgctcaagga ggctaaggcc aaggcatcca cagtgaaggc taaattgcta tccgtagagg   7860
aggcatgtag cctgacgccc ccgcactccg ccagatcaaa atttggctat gggccgaagg   7920
atgtccgaag ccattccagt aaggctatac gccacatcaa ctccgtgtgg caggaccttc   7980
tggaggacaa tacaacacct atagacacta ccatcatggc caagaatgaa gtcttctgcg   8040
tgaaggccga aaaagggggt cgcaagcccg ctcgccttat cgtgtacccc gacctggggg   8100
tgcgcgtgtg cgagaagaga gctttgtatg acgtagtcaa acagctcccc attgccgtga   8160
tgggaccctc ctacgggttc cagtactcgc cagcgcagcg ggtcgacttc ctgcttaacg   8220
cgtggaaatc aaagaaaaac cctatggggt tttcctatga cacccgttgc tttgactcaa   8280
cagtcactga ggctgatatc cgtacggagg aagacctcta tcaatcttgt gacctggtcc   8340
ctgaggcccg cgcggccata aggtctctca cagagaggct ttacatcggg ggcccactta   8400
ccaattctaa gggacaaaac tgcggctatc ggcgatgccg cgcaagcggc gtgctgacca   8460
ctagctgcgg taacaccata acttgctacc ttaaggctag tgcggcctgt cgagctgcaa   8520
agctccagga ctgcaccatg ctcgtgtgcg gcgacgacct cgtcgttatc tgtgaaagcg   8580
ccggtgtcaa ggaggacgct gcgagcctga gagccttcac cgaggctatg accaggtact   8640
ccggcccccc gggagacccg gctcaaccag aatacgactt ggagcttata acatcctgct   8700
cctccaatgt gtcggtcgcg cgcgacggcg ctggccaaag ggtctattat ctgacccgtg   8760
aacctgagac tcccctcgcg cgtgccgctt gggagacagc aagacacact ccagtgaact   8820
cctggctagg caacatcatc atgtttgccc ccactctgtg ggtacggatg gtcctcatga   8880
cccacttatt ctccatactc atagttcagg agcaccttga aaaggctcta gattgtgaaa   8940
tctatggagc cacacactcc gtcccaccgt tggacctacc tgaaatcatt caaagactcc   9000
atggcctcag cgcgttttcg ctccacagtt actctccagg tgaaatcaat agggtggctt   9060
catgcctcag gaaacttggg gttccaccct tgcgagcttg gagacaccgg gcccggagcg   9120
```

-continued tccgcgccac actcctatcc caggggggga aagccgccat atgcggtaag tacctcttca 9180
actgggcggt gaaaaccaaa ctcaaactca ttccattacc gctcgcgtct catttggact 9240
tgtccaattg gttcacgggc ggctacagcg ggggagacat ttatcacagc gtgtctcatg 9300
cccggccccg ttggtttctc tggtgcctac tcctactctc agtaggggta ggcatctacc 9360
tccttcccaa ccgatagacg gttgggcaac cactccaggc ctttaggccc tatttaaaca 9420
ctccaggcct ttaggccccg t 9441

<210> SEQ ID NO 2
<211> LENGTH: 3011
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Tyr
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Val
180 185 190

Gly Val Arg Asn Ser Ser Gly Val Tyr His Val Thr Asn Asp Cys Pro
195 200 205

Asn Ala Ser Val Val Tyr Glu Thr Asp Ser Leu Ile Ile His Leu Pro
210 215 220

Gly Cys Val Pro Cys Val Arg Glu Gly Asn Gly Ser Arg Cys Trp Val
225 230 235 240

Ser Leu Ser Pro Thr Val Ala Ala Lys Asp Pro Gly Val Pro Val Asn
245 250 255

Glu Ile Arg Arg His Val Asp Leu Ile Ala Gly Ala Ala Ala Phe Cys
260 265 270

Ser Ala Met Tyr Val Gly His Leu Cys Gly Ser Ile Phe Leu Val Gly
275 280 285

Gln Leu Phe Thr Leu Ser Pro Arg Arg His Trp Thr Thr Gln Asp Cys
290 295 300

Asn Cys Ser Ile Tyr Pro Gly His Val Thr Gly His Arg Met Ala Trp
305 310 315 320

-continued

```
Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Thr Lys Val Leu Val Val Leu Leu Leu Phe Ala Gly Val Asp Ala Thr
    370                 375                 380

Thr Ile Val Ser Gly Gly Ser Ala Gly Arg Ser Thr Ala Gly Leu Val
385                 390                 395                 400

Gly Leu Phe Ser Pro Gly Ala Arg Gln Asn Ile Gln Leu Ile Asn Thr
                405                 410                 415

Asn Gly Ser Trp His Ile Asn Arg Thr Ala Leu Asn Cys Asn Asp Thr
            420                 425                 430

Leu Gln Thr Gly Trp Val Ala Gly Leu Phe Tyr Thr Asn Lys Phe Asn
        435                 440                 445

Ser Ser Gly Cys Pro Glu Arg Leu Ala Ser Cys Arg Pro Leu Ala Asp
    450                 455                 460

Phe Asp Gln Gly Trp Gly Pro Ile Ser Tyr Thr Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Glu Ser Val Cys Gly Pro Val Tyr Cys Phe Thr Pro Ser
            500                 505                 510

Pro Val Val Val Gly Thr Thr Asp Arg Ser Gly Ala Pro Thr Tyr Asn
        515                 520                 525

Trp Gly Glu Asn Glu Thr Asp Val Phe Val Leu Asn Asn Thr Arg Pro
    530                 535                 540

Arg Leu Gly Asn Trp Phe Gly Gly Thr Trp Met Asn Ser Thr Gly Phe
545                 550                 555                 560

Thr Lys Val Cys Gly Ala Pro Pro Cys Ala Ile Gly Gly Val Gly Asn
                565                 570                 575

Asn Thr Leu Tyr Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Ile His Tyr Pro Tyr Arg Leu Trp His Tyr Pro Cys Thr Ile Asn Tyr
    610                 615                 620

Thr Ile Phe Lys Ile Arg Met Phe Val Gly Gly Val Glu His Arg Leu
625                 630                 635                 640

Asp Ala Ala Cys Asn Trp Thr Arg Gly Glu Arg Cys Asp Leu Asp Asp
                645                 650                 655

Arg Asp Arg Ala Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Leu Ser Ser Ala Val Thr Ser Trp Val Ile Lys Trp Glu Tyr Val Val
705                 710                 715                 720

Leu Leu Phe Leu Leu Leu Ala Asp Ala Arg Ile Cys Ala Cys Leu Trp
                725                 730                 735
```

-continued

```
Met Met Leu Leu Ile Ser Gln Val Glu Ala Ala Leu Glu Asn Leu Ile
            740                 745                 750

Val Leu Asn Ala Ala Ser Leu Val Gly Thr His Gly Ile Val Pro Phe
        755                 760                 765

Phe Ile Phe Phe Cys Ala Ala Trp Tyr Leu Lys Gly Lys Trp Ala Pro
    770                 775                 780

Gly Leu Ala Tyr Ser Val Tyr Gly Met Trp Pro Leu Leu Leu Leu Leu
785                 790                 795                 800

Leu Ala Leu Pro Gln Arg Ala Tyr Ala Leu Asp Gln Glu Leu Ala Ala
                805                 810                 815

Ser Cys Gly Ala Thr Val Phe Ile Cys Leu Ala Val Leu Thr Leu Ser
            820                 825                 830

Pro Tyr Tyr Lys Gln Tyr Met Ala Arg Gly Ile Trp Trp Leu Gln Tyr
        835                 840                 845

Met Leu Thr Arg Ala Glu Ala Leu Leu Gln Val Trp Val Pro Pro Leu
    850                 855                 860

Asn Ala Arg Gly Gly Arg Asp Gly Val Val Leu Leu Thr Cys Val Leu
865                 870                 875                 880

His Pro His Leu Leu Phe Glu Ile Thr Lys Ile Met Leu Ala Ile Leu
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Met
        915                 920                 925

Val Gly Gly His Tyr Val Gln Met Val Thr Ile Lys Leu Gly Ala Leu
    930                 935                 940

Thr Gly Thr Tyr Ile Tyr Asn His Leu Thr Pro Leu Arg Asp Trp Ala
945                 950                 955                 960

His Asn Gly Leu Gln Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                1005

Glu Ile  Leu Leu Gly Pro Ala  Asp Gly Met Ala Ser  Arg Gly Trp
    1010                1015                1020

Arg Leu  Leu Ala Pro Ile Thr  Ala Tyr Ala Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Ala Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Ser Lys Gly  Pro Val Ile
    1085                1090                1095

Leu Met  Tyr Thr Asn Val Asp  Gln Asp Leu Gly Gly  Trp Thr Ala
    1100                1105                1110

Pro Gln  Val Leu Gly Ser Leu  Thr Pro Trp Ser Cys  Gly Ser Ser
    1115                1120                1125

Asp Leu  Tyr Leu Val Thr Arg  His Ala Asp Val Ile  Pro Val Pro
    1130                1135                1140

Arg Arg  Gly Glu Thr Arg Gly  Ser Leu Leu Ser Pro  Arg Pro Ile
```

-continued

```
    1145                1150                1155

Ser Tyr  Leu Lys Gly Ser Ser  Gly Gly Pro Leu Leu  Cys Pro Met
    1160                1165                1170

Gly His  Ala Val Gly Ile Phe  Arg Ala Ala Val Cys  Thr Arg Gly
    1175                1180                1185

Val Ala  Lys Ala Val Asp Phe  Val Pro Val Glu Ser  Leu Glu Thr
    1190                1195                1200

Thr Met  Arg Ser Pro Val Phe  Thr Asp Asn Ser Ser  Pro Leu Thr
    1205                1210                1215

Val Pro  Gln Ser Tyr Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260

Phe Gly  Ala Tyr Met Ser Lys  Ala His Gly Ile Asp  Pro Asn Ile
    1265                1270                1275

Arg Thr  Gly Val Arg Thr Ile  Thr Thr Gly Ser Pro  Ile Thr Tyr
    1280                1285                1290

Ser Thr  Tyr Gly Lys Phe Leu  Ala Asp Gly Gly Cys  Pro Gly Gly
    1295                1300                1305

Ala Tyr  Asp Ile Ile Ile Cys  Asp Glu Cys His Ser  Val Asp Ala
    1310                1315                1320

Thr Ser  Ile Leu Gly Ile Gly  Thr Val Leu Asp Gln  Ala Glu Thr
    1325                1330                1335

Ala Gly  Val Arg Leu Thr Val  Leu Ala Thr Ala Thr  Pro Pro Gly
    1340                1345                1350

Ser Val  Thr Val Pro His Ser  Asn Ile Glu Glu Val  Ala Leu Ser
    1355                1360                1365

Ala Asp  Gly Glu Ile Pro Phe  Tyr Gly Lys Ala Ile  Pro Leu Asn
    1370                1375                1380

Tyr Ile  Lys Gly Gly Arg His  Leu Ile Phe Cys His  Ser Lys Lys
    1385                1390                1395

Lys Cys  Asp Glu Leu Ala Ala  Lys Leu Val Gly Pro  Gly Val Asn
    1400                1405                1410

Ala Val  Ala Phe Tyr Arg Gly  Leu Asp Val Ser Val  Ile Pro Thr
    1415                1420                1425

Thr Gly  Asp Val Val Val Val  Ala Thr Asp Ala Leu  Met Thr Gly
    1430                1435                1440

Phe Thr  Gly Asp Phe Asp Ser  Val Ile Asp Cys Asn  Thr Cys Val
    1445                1450                1455

Val Gln  Thr Val Asp Phe Ser  Leu Asp Pro Ile Phe  Ser Ile Glu
    1460                1465                1470

Thr Ser  Thr Val Pro Gln Asp  Ala Val Ser Arg Ser  Gln Arg Arg
    1475                1480                1485

Gly Arg  Thr Gly Arg Gly Lys  His Gly Ile Tyr Arg  Tyr Val Ser
    1490                1495                1500

Pro Gly  Glu Arg Pro Ser Gly  Met Phe Asp Ser Val  Val Leu Cys
    1505                1510                1515

Glu Cys  Tyr Asp Ala Gly Cys  Ala Trp Tyr Glu Leu  Thr Pro Ala
    1520                1525                1530

Glu Thr  Thr Val Arg Leu Arg  Ala Tyr Leu Asn Thr  Pro Gly Leu
    1535                1540                1545
```

-continued

```
Pro Val Cys Gln Asp His Leu Glu Phe Trp Glu Ser Val Phe Thr
    1550                1555                1560

Gly Leu Thr His Ile Asp Ala His Phe Leu Ser Gln Thr Lys Gln
    1565                1570                1575

Ser Gly Glu Asn Phe Pro Tyr Leu Val Ala Tyr Gln Ala Thr Val
    1580                1585                1590

Cys Ala Arg Ala Arg Ala Pro Pro Pro Ser Trp Asp Gln Met Trp
    1595                1600                1605

Lys Cys Leu Ile Arg Leu Lys Pro Thr Leu Thr Gly Ala Thr Pro
    1610                1615                1620

Leu Leu Tyr Arg Leu Gly Ser Val Gln Asn Glu Ile Thr Leu Thr
    1625                1630                1635

His Pro Ile Thr Gln Tyr Ile Met Ala Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Ser Thr Gly Ser Val Val Ile Val
    1670                1675                1680

Gly Arg Ile Ile Leu Gly Gly Lys Pro Ala Val Ile Pro Asp Arg
    1685                1690                1695

Glu Val Leu Tyr Arg Glu Phe Asp Glu Met Glu Glu Cys Ala Ala
    1700                1705                1710

His Val Pro Tyr Leu Glu Gln Gly Met His Leu Ala Glu Gln Phe
    1715                1720                1725

Lys Gln Lys Ala Leu Gly Leu Leu Gln Thr Ala Ser Lys Gln Thr
    1730                1735                1740

Glu Thr Ile Thr Pro Ile Val Gln Ser Asn Trp Gln Lys Leu Glu
    1745                1750                1755

Ser Phe Trp Ala Lys His Met Trp Asn Phe Val Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ser Phe Thr Ala Ala Val Thr Ser Pro Leu Thr Thr
    1790                1795                1800

Gln Gln Thr Leu Leu Phe Asn Ile Leu Gly Gly Trp Leu Ala Ala
    1805                1810                1815

Gln Leu Ala Ala Pro Ala Ala Ala Thr Ala Phe Val Gly Ala Gly
    1820                1825                1830

Ile Thr Gly Ala Val Val Gly Ser Val Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Thr Pro Thr Thr Glu Asp
    1865                1870                1875

Leu Val Asn Leu Leu Pro Ala Ile Leu Ser Pro Gly Ala Leu Val
    1880                1885                1890

Val Ala Val Val Cys Ala Ala Ile Leu Arg Arg His Val Gly Leu
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935
```

-continued

```
Asp Ala  Ser Ala Arg Val Thr  Pro Ile Leu Thr Arg  Leu Thr Val
    1940                 1945                 1950

Thr Gln  Leu Leu Lys Gly Leu  His Val Trp Ile Ser  Ser Asn Cys
    1955                 1960                 1965

Ile Ala  Pro Cys Ala Ser Ser  Trp Leu Lys Asp Val  Trp Asn Trp
    1970                 1975                 1980

Ile Cys  Glu Val Leu Ser Asp  Phe Lys Asn Trp Leu  Lys Ala Lys
    1985                 1990                 1995

Leu Val  Pro Gln Leu Pro Gly  Ile Pro Phe Val Ser  Cys Gln Arg
    2000                 2005                 2010

Gly Tyr  Arg Gly Val Trp Arg  Gly Glu Gly Ile Val  His Thr Arg
    2015                 2020                 2025

Cys Pro  Cys Gly Ala Asn Ile  Thr Gly His Val Lys  Asn Gly Ser
    2030                 2035                 2040

Met Arg  Ile Val Gly Pro Lys  Thr Cys Ser Asn Thr  Trp Arg Gly
    2045                 2050                 2055

Ser Phe  Pro Ile Asn Ala Tyr  Thr Thr Gly Pro Cys  Thr Pro Ser
    2060                 2065                 2070

Pro Ala  Pro Asn Tyr Thr Phe  Ala Leu Trp Arg Val  Ser Ala Glu
    2075                 2080                 2085

Glu Tyr  Val Glu Val Arg Arg  Leu Gly Asp Phe His  Tyr Val Thr
    2090                 2095                 2100

Gly Val  Thr Thr Asp Lys Leu  Lys Cys Pro Cys Gln  Val Pro Ser
    2105                 2110                 2115

Pro Glu  Phe Ser Thr Glu Val  Asp Gly Val Arg Leu  His Arg Tyr
    2120                 2125                 2130

Ala Pro  Pro Cys Lys Pro Leu  Leu Arg Asp Glu Val  Thr Phe Ser
    2135                 2140                 2145

Val Gly  Phe Asn Glu Tyr Leu  Val Gly Ser Gln Leu  Pro Cys Glu
    2150                 2155                 2160

Pro Glu  Pro Asp Val Ala Ala  Leu Thr Ser Met Leu  Thr Asp Pro
    2165                 2170                 2175

Ser His  Ile Thr Ala Lys Thr  Ala Ala Arg Arg Leu  Lys Arg Gly
    2180                 2185                 2190

Ser Pro  Pro Ser Leu Ala Ser  Ser Ser Ala Ser Gln  Leu Ser Ala
    2195                 2200                 2205

Pro Ser  Leu Lys Ala Thr Cys  Thr Thr His His Asp  Ser Pro Asp
    2210                 2215                 2220

Ala Asp  Leu Ile Glu Ala Asn  Leu Leu Trp Arg Arg  Glu Met Gly
    2225                 2230                 2235

Gly Asn  Ile Thr Arg Val Glu  Ser Glu Asn Lys Ile  Val Val Leu
    2240                 2245                 2250

Asp Ser  Phe Asp Pro Leu Val  Ala Glu Glu Asp Asp  Arg Glu Ile
    2255                 2260                 2265

Ser Ile  Pro Ala Glu Ile Leu  Arg Lys Phe Lys Gln  Phe Pro Pro
    2270                 2275                 2280

Ala Met  Pro Ile Trp Ala Arg  Pro Asp Tyr Asn Pro  Pro Leu Val
    2285                 2290                 2295

Glu Pro  Trp Lys Arg Pro Asp  Cys Asp Pro Pro Leu  Val His Gly
    2300                 2305                 2310

Cys Pro  Leu Pro Pro Pro Lys  Pro Thr Pro Val Pro  Pro Pro Arg
    2315                 2320                 2325

Lys Lys  Arg Thr Val Val Leu  Asp Glu Ser Thr Val  Ser Ser Ala
```

-continued

```
    2330                2335                2340

Leu Ala  Glu Leu Ala Thr Lys  Thr Phe Gly Ser Ser  Thr Thr Ser
    2345                2350                2355

Gly Val  Thr Ser Gly Glu Ala  Ala Glu Ser Ser Pro  Ala Leu Ser
    2360                2365                2370

Cys Asp  Gly Glu Leu Asp Ser  Glu Ala Glu Ser Tyr  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Ser  Asp Gly Gly Thr Glu  Asp Val Val
    2405                2410                2415

Cys Cys  Ser Met Ser Tyr Ser  Trp Thr Gly Ala Leu  Ile Thr Pro
    2420                2425                2430

Cys Ala  Ala Glu Glu Thr Lys  Leu Pro Ile Asn Ala  Leu Ser Asn
    2435                2440                2445

Ser Leu  Leu Arg His His Asn  Leu Val Tyr Ser Thr  Thr Ser Arg
    2450                2455                2460

Ser Ala  Gly Lys Arg Gln Lys  Lys Val Thr Phe Asp  Arg Leu Gln
    2465                2470                2475

Val Leu  Asp Asp His Tyr Arg  Asp Val Leu Lys Glu  Ala Lys Ala
    2480                2485                2490

Lys Ala  Ser Thr Val Lys Ala  Lys Leu Leu Ser Val  Glu Glu Ala
    2495                2500                2505

Cys Ser  Leu Thr Pro Pro His  Ser Ala Arg Ser Lys  Phe Gly Tyr
    2510                2515                2520

Gly Pro  Lys Asp Val Arg Ser  His Ser Ser Lys Ala  Ile Arg His
    2525                2530                2535

Ile Asn  Ser Val Trp Gln Asp  Leu Leu Glu Asp Asn  Thr Thr Pro
    2540                2545                2550

Ile Asp  Thr Thr Ile Met Ala  Lys Asn Glu Val Phe  Cys Val Lys
    2555                2560                2565

Ala Glu  Lys Gly Gly Arg Lys  Pro Ala Arg Leu Ile  Val Tyr Pro
    2570                2575                2580

Asp Leu  Gly Val Arg Val Cys  Glu Lys Arg Ala Leu  Tyr Asp Val
    2585                2590                2595

Val Lys  Gln Leu Pro Ile Ala  Val Met Gly Pro Ser  Tyr Gly Phe
    2600                2605                2610

Gln Tyr  Ser Pro Ala Gln Arg  Val Asp Phe Leu Leu  Asn Ala Trp
    2615                2620                2625

Lys Ser  Lys Lys Asn Pro Met  Gly Phe Ser Tyr Asp  Thr Arg Cys
    2630                2635                2640

Phe Asp  Ser Thr Val Thr Glu  Ala Asp Ile Arg Thr  Glu Glu Asp
    2645                2650                2655

Leu Tyr  Gln Ser Cys Asp Leu  Val Pro Glu Ala Arg  Ala Ala Ile
    2660                2665                2670

Arg Ser  Leu Thr Glu Arg Leu  Tyr Ile Gly Gly Pro  Leu Thr Asn
    2675                2680                2685

Ser Lys  Gly Gln Asn Cys Gly  Tyr Arg Arg Cys Arg  Ala Ser Gly
    2690                2695                2700

Val Leu  Thr Thr Ser Cys Gly  Asn Thr Ile Thr Cys  Tyr Leu Lys
    2705                2710                2715

Ala Ser  Ala Ala Cys Arg Ala  Ala Lys Leu Gln Asp  Cys Thr Met
    2720                2725                2730
```

-continued

```
Leu Val  Cys Gly Asp Asp Leu  Val Val Ile Cys Glu  Ser Ala Gly
    2735                 2740                 2745

Val Lys  Glu Asp Ala Ala Ser  Leu Arg Ala Phe Thr  Glu Ala Met
    2750                 2755                 2760

Thr Arg  Tyr Ser Gly Pro Pro  Gly Asp Pro Ala Gln  Pro Glu Tyr
    2765                 2770                 2775

Asp Leu  Glu Leu Ile Thr Ser  Cys Ser Ser Asn Val  Ser Val Ala
    2780                 2785                 2790

Arg Asp  Gly Ala Gly Gln Arg  Val Tyr Tyr Leu Thr  Arg Glu Pro
    2795                 2800                 2805

Glu Thr  Pro Leu Ala Arg Ala  Ala Trp Glu Thr Ala  Arg His Thr
    2810                 2815                 2820

Pro Val  Asn Ser Trp Leu Gly  Asn Ile Ile Met Phe  Ala Pro Thr
    2825                 2830                 2835

Leu Trp  Val Arg Met Val Leu  Met Thr His Leu Phe  Ser Ile Leu
    2840                 2845                 2850

Ile Val  Gln Glu His Leu Glu  Lys Ala Leu Asp Cys  Glu Ile Tyr
    2855                 2860                 2865

Gly Ala  Thr His Ser Val Pro  Pro Leu Asp Leu Pro  Glu Ile Ile
    2870                 2875                 2880

Gln Arg  Leu His Gly Leu Ser  Ala Phe Ser Leu His  Ser Tyr Ser
    2885                 2890                 2895

Pro Gly  Glu Ile Asn Arg Val  Ala Ser Cys Leu Arg  Lys Leu Gly
    2900                 2905                 2910

Val Pro  Pro Leu Arg Ala Trp  Arg His Arg Ala Arg  Ser Val Arg
    2915                 2920                 2925

Ala Thr  Leu Leu Ser Gln Gly  Gly Lys Ala Ala Ile  Cys Gly Lys
    2930                 2935                 2940

Tyr Leu  Phe Asn Trp Ala Val  Lys Thr Lys Leu Lys  Leu Ile Pro
    2945                 2950                 2955

Leu Pro  Leu Ala Ser His Leu  Asp Leu Ser Asn Trp  Phe Thr Gly
    2960                 2965                 2970

Gly Tyr  Ser Gly Gly Asp Ile  Tyr His Ser Val Ser  His Ala Arg
    2975                 2980                 2985

Pro Arg  Trp Phe Leu Trp Cys  Leu Leu Leu Leu Ser  Val Gly Val
    2990                 2995                 3000

Gly Ile  Tyr Leu Leu Pro Asn  Arg
    3005                 3010


<210> SEQ ID NO 3
<211> LENGTH: 341
<212> TYPE: DNA
<213> ORGANISM: Hepatitis C virus

<400> SEQUENCE: 3

gccagccccc tgatgggggc gacactccgc catgaatcac tcccctgtga ggaactactg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag    180

gacgaccggg tcctttcttg gataaacccg ctcaacgcct ggagatttgg gcgtgccccc    240

gcaagactgc tagccgagta gtgttgggtc gcgaaaggcc ttgtggtact gcctgatagg    300

gtgcttgcga gtgccccggg aggtctcgta gaccgtgcac c                        341
```

-continued

<210> SEQ ID NO 4
<211> LENGTH: 67
<212> TYPE: DNA
<213> ORGANISM: Hepatitis C virus

<400> SEQUENCE: 4
tagacggttg ggcaaccact ccaggccttt aggccctatt taaacactcc aggcctttag 60
gccccgt 67

<210> SEQ ID NO 5
<211> LENGTH: 573
<212> TYPE: DNA
<213> ORGANISM: Hepatitis C virus

<400> SEQUENCE: 5
atgagcacga atcctaaacc tcaaagaaaa accaaacgta acaccaaccg tcgcccacag 60
gacgtcaagt tcccgggtgg cggacagatc gttggtggag tttacttgtt gccgcgcagg 120
ggccctagat tgggtgtgcg cgcgacgagg aagacttccg agcggtcgca acctcgaggt 180
agacgtcagc ctatccccaa ggcacgtcgg cccgagggca ggacctgggc tcagcccggg 240
tacccttggc ccctctatgg caatgagggc tgcgggtggg cgggatggct cctgtctccc 300
cgcggctctc ggcctagttg gggccccaca gacccccggc gtagatcgcg caatttgggt 360
aaggtcatcg ataccttac gtatggcttc gccgacctca tggggtacat accgctcgtc 420
ggcgcccccc ttgggggcgc tgccagggcc ctggcgcacg gcgtccgggt cctggaagac 480
ggcgtgaact atgcaacagg gaaccttcct ggttgctctt tctctatctt ccttctggcc 540
ctgctctctt gcttgactgt gcccgcttcg gcc 573

<210> SEQ ID NO 6
<211> LENGTH: 191
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Tyr
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

-continued

```
Phe Leu Leu Ala Leu Leu Ser Cys Leu Thr Val Pro Ala Ser Ala
            180                 185                 190
```

<210> SEQ ID NO 7
<211> LENGTH: 576
<212> TYPE: DNA
<213> ORGANISM: Hepatitis C virus

<400> SEQUENCE: 7

```
gtcggagtgc gcaactcttc gggggtgtac catgtcacca atgattgccc caatgcgtct      60

gttgtgtacg agacagatag cttgatcata catctgccgg ggtgtgtgcc ctgcgtacgc     120

gagggcaacg gttcgaggtg ctgggtctcc cttagtccta ctgttgccgc taaggatccg     180

ggcgtcccgg tcaacgagat tcggcgtcac gtcgacctga ttgccggggc cgctgcattc     240

tgttcggcta tgtatgtagg gcacttatgc ggttccatct tcctcgttgg ccagcttttc     300

accctctccc ctaggcgcca ctggacaaca caagactgta attgctccat ctacccagga     360

catgtgacag gccatcgaat ggcttgggac atgatgatga actggtcccc tacgacggcg     420

ctggtagtag cccagctgct ccggatccca caagccatct tggacatgat cgctggtgct     480

cactggggag tcctggcggg catagcgtat ttctccatgg tggggaactg gacgaaggtc     540

ctggtagtgc tgctgctatt tgccggcgtc gacgcg                               576
```

<210> SEQ ID NO 8
<211> LENGTH: 192
<212> TYPE: PRT
<213> ORGANISM: Hepatitis C virus

<400> SEQUENCE: 8

```
Val Gly Val Arg Asn Ser Ser Gly Val Tyr His Val Thr Asn Asp Cys
1               5                   10                  15

Pro Asn Ala Ser Val Val Tyr Glu Thr Asp Ser Leu Ile Ile His Leu
            20                  25                  30

Pro Gly Cys Val Pro Cys Val Arg Glu Gly Asn Gly Ser Arg Cys Trp
        35                  40                  45

Val Ser Leu Ser Pro Thr Val Ala Ala Lys Asp Pro Gly Val Pro Val
    50                  55                  60

Asn Glu Ile Arg Arg His Val Asp Leu Ile Ala Gly Ala Ala Ala Phe
65                  70                  75                  80

Cys Ser Ala Met Tyr Val Gly His Leu Cys Gly Ser Ile Phe Leu Val
                85                  90                  95

Gly Gln Leu Phe Thr Leu Ser Pro Arg Arg His Trp Thr Thr Gln Asp
            100                 105                 110

Cys Asn Cys Ser Ile Tyr Pro Gly His Val Thr Gly His Arg Met Ala
        115                 120                 125

Trp Asp Met Met Met Asn Trp Ser Pro Thr Thr Ala Leu Val Val Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Thr Lys Val Leu Val Val Leu Leu Leu Phe Ala Gly Val Asp Ala
            180                 185                 190
```

<210> SEQ ID NO 9
<211> LENGTH: 1278

-continued

<212> TYPE: DNA
<213> ORGANISM: Hepatitis C virus

<400> SEQUENCE: 9

```
acgaccatcg tctccggggg aagtgccggc cgcagcacgg ctggacttgt tgggctcttc     60

tcaccaggcg cccggcagaa catccagctg atcaacacca acggcagttg gcacatcaac    120

cgcacggccc tgaactgcaa tgataccctt caaaccggct gggtagcagg gcttttctat    180

accaacaaat tcaactcttc gggttgcccc gagaggttgg ccagctgccg acccccttgcc   240

gactttgacc agggctgggg ccctatcagt tataccaacg gaagcggccc cgaccaacgc    300

ccctactgct ggcactaccc cccaaaacct tgtggtattg tgcccgcaga gagcgtgtgt    360

ggcccagtat actgcttcac tcccagcccc gtggtggtgg gaacgaccga caggtcgggc    420

gcgcccacct acaactgggg tgaaaatgaa acggacgttt tcgtcctcaa caacaccagg    480

ccacggctgg gcaattggtt cggtggtacc tggatgaact caactggatt caccaaggtg    540

tgcggagcgc ccccttgtgc catcggaggg gtgggcaaca acaccttgta ctgccccact    600

gattgtttcc gcaaacatcc ggaagccacg tactctcggt gcggctccgg tccttggatt    660

acacccaggt gcttgatcca ctacccgtat aggctttggc attatccttg taccatcaat    720

tacaccatat tcaagatcag gatgtttgtg ggcggggttg agcacaggct cgacgccgcg    780

tgcaactgga cgcggggaga gcgctgcgac ttggacgaca gggatcgggc cgagttgagc    840

cctctgttgc tgtccactac gcaatggcag gtcctcccct gctcattcac aacactgccc    900

gccctgtcaa ctggcctgat acatctccac cagaacatcg tggacgtgca gtacctctat    960

gggttgagct cggcagtcac atcctgggtc ataaagtggg agtacgttgt gctcctcttc   1020

ttgctgctag cagatgctcg catttgtgcc tgcttgtgga tgatgcttct catatctcag   1080

gtagaggcgg cgctggagaa cttgatagtt ctcaacgctg cttccctagt cgggacacat   1140

ggcatcgtcc ccttcttcat cttttttgt gcagcttggt acctaaaagg caagtgggcc    1200

cctggactcg cctattccgt ctatgggatg tggccactgc tcctgcttct cctggcgttg   1260

ccccaacggg catacgcc                                                 1278
```

<210> SEQ ID NO 10
<211> LENGTH: 426
<212> TYPE: PRT
<213> ORGANISM: Hepatitis C virus

<400> SEQUENCE: 10

```
Thr Thr Ile Val Ser Gly Gly Ser Ala Gly Arg Ser Thr Ala Gly Leu
1               5                   10                  15

Val Gly Leu Phe Ser Pro Gly Ala Arg Gln Asn Ile Gln Leu Ile Asn
            20                  25                  30

Thr Asn Gly Ser Trp His Ile Asn Arg Thr Ala Leu Asn Cys Asn Asp
        35                  40                  45

Thr Leu Gln Thr Gly Trp Val Ala Gly Leu Phe Tyr Thr Asn Lys Phe
    50                  55                  60

Asn Ser Ser Gly Cys Pro Glu Arg Leu Ala Ser Cys Arg Pro Leu Ala
65                  70                  75                  80

Asp Phe Asp Gln Gly Trp Gly Pro Ile Ser Tyr Thr Asn Gly Ser Gly
                85                  90                  95

Pro Asp Gln Arg Pro Tyr Cys Trp His Tyr Pro Pro Lys Pro Cys Gly
            100                 105                 110

Ile Val Pro Ala Glu Ser Val Cys Gly Pro Val Tyr Cys Phe Thr Pro
```

-continued

```
        115                 120                 125

Ser Pro Val Val Val Gly Thr Thr Asp Arg Ser Gly Ala Pro Thr Tyr
    130                 135                 140

Asn Trp Gly Glu Asn Glu Thr Asp Val Phe Val Leu Asn Asn Thr Arg
145                 150                 155                 160

Pro Arg Leu Gly Asn Trp Phe Gly Gly Thr Trp Met Asn Ser Thr Gly
                165                 170                 175

Phe Thr Lys Val Cys Gly Ala Pro Pro Cys Ala Ile Gly Gly Val Gly
            180                 185                 190

Asn Asn Thr Leu Tyr Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Leu Ile His Tyr Pro Tyr Arg Leu Trp His Tyr Pro Cys Thr Ile Asn
225                 230                 235                 240

Tyr Thr Ile Phe Lys Ile Arg Met Phe Val Gly Gly Val Glu His Arg
                245                 250                 255

Leu Asp Ala Ala Cys Asn Trp Thr Arg Gly Glu Arg Cys Asp Leu Asp
            260                 265                 270

Asp Arg Asp Arg Ala Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Leu Ser Ser Ala Val Thr Ser Trp Val Ile Lys Trp Glu Tyr Val
                325                 330                 335

Val Leu Leu Phe Leu Leu Leu Ala Asp Ala Arg Ile Cys Ala Cys Leu
            340                 345                 350

Trp Met Met Leu Leu Ile Ser Gln Val Glu Ala Ala Leu Glu Asn Leu
        355                 360                 365

Ile Val Leu Asn Ala Ala Ser Leu Val Gly Thr His Gly Ile Val Pro
    370                 375                 380

Phe Phe Ile Phe Phe Cys Ala Ala Trp Tyr Leu Lys Gly Lys Trp Ala
385                 390                 395                 400

Pro Gly Leu Ala Tyr Ser Val Tyr Gly Met Trp Pro Leu Leu Leu Leu
                405                 410                 415

Leu Leu Ala Leu Pro Gln Arg Ala Tyr Ala
            420                 425


<210> SEQ ID NO 11
<211> LENGTH: 591
<212> TYPE: DNA
<213> ORGANISM: Hepatitis C virus

<400> SEQUENCE: 11

ttggatcagg agttggccgc gtcgtgtggg gccacggtct tcatctgcct agcggtgctc      60

actctatcgc catattacaa acagtacatg gcccgcggca tctggtggct gcagtacatg     120

ctgaccagag cagaggcgct cctacaggtt tgggtccccc cgctcaacgc ccgaggaggg     180

cgcgacggag tcgtactgct cacgtgtgtg ctccacccgc acttgctctt tgaaatcacc     240

aagatcatgc tggccattct cgggcctttg tggatcttgc aggccagtct gctcaaggta     300

ccgtacttcg tgcgcgttca gggccttctc cggatctgcg cgctagcgcg gaagatggtc     360
```

-continued

```
ggaggccatt acgtgcaaat ggtcaccatc aagttagggg cgctcactgg cacctatatt    420

tataaccatc tcactcctct tcgggactgg gcgcacaacg gcttgcaaga cctagccgta    480

gctgtggagc cagtcgtctt ctcccaaatg gagaccaagc tcatcacgtg gggggcagac    540

acagccgcgt gtggtgacat catcaacggc ttgcccgtct ccgcccgcag g             591
```

<210> SEQ ID NO 12
<211> LENGTH: 197
<212> TYPE: PRT
<213> ORGANISM: Hepatitis C virus

<400> SEQUENCE: 12

```
Leu Asp Gln Glu Leu Ala Ala Ser Cys Gly Ala Thr Val Phe Ile Cys
1               5                   10                  15

Leu Ala Val Leu Thr Leu Ser Pro Tyr Tyr Lys Gln Tyr Met Ala Arg
            20                  25                  30

Gly Ile Trp Trp Leu Gln Tyr Met Leu Thr Arg Ala Glu Ala Leu Leu
        35                  40                  45

Gln Val Trp Val Pro Pro Leu Asn Ala Arg Gly Gly Arg Asp Gly Val
    50                  55                  60

Val Leu Leu Thr Cys Val Leu His Pro His Leu Leu Phe Glu Ile Thr
65                  70                  75                  80

Lys Ile Met Leu Ala Ile Leu Gly Pro Leu Trp Ile Leu Gln Ala Ser
            85                  90                  95

Leu Leu Lys Val Pro Tyr Phe Val Arg Val Gln Gly Leu Leu Arg Ile
            100                 105                 110

Cys Ala Leu Ala Arg Lys Met Val Gly Gly His Tyr Val Gln Met Val
        115                 120                 125

Thr Ile Lys Leu Gly Ala Leu Thr Gly Thr Tyr Ile Tyr Asn His Leu
    130                 135                 140

Thr Pro Leu Arg Asp Trp Ala His Asn Gly Leu Gln Asp Leu Ala Val
145                 150                 155                 160

Ala Val Glu Pro Val Val Phe Ser Gln Met Glu Thr Lys Leu Ile Thr
            165                 170                 175

Trp Gly Ala Asp Thr Ala Ala Cys Gly Asp Ile Ile Asn Gly Leu Pro
            180                 185                 190

Val Ser Ala Arg Arg
        195
```

<210> SEQ ID NO 13
<211> LENGTH: 1953
<212> TYPE: DNA
<213> ORGANISM: Hepatitis C virus

<400> SEQUENCE: 13

```
ggccaggaga tactgctcgg accagccgat ggaatggcct ctaggggatg gaggttgctg     60

gcgcccatca cggcgtacgc tcagcagaca aggggcctcc tagggtgtat aatcaccagc    120

ctgactggcc gggacaagaa ccaagtggag ggtgaagtcc agattgtgtc aactgctgcc    180

caaacgttct tggcgacgtg catcaacggg gtatgctgga ctgtctacca cggggccgga    240

accaggacca ttgcatcatc caagggtcct gttattctaa tgtataccaa tgtagaccaa    300

gacctcgggg gctggaccgc tcctcaagtg ctcggctcac tgacaccctg gagctgcggc    360

tcctcggacc tttacctggt cacgaggcat gccgatgtca ttcccgtgcc gcggcgaggt    420

gaaaccaggg gcagcctgct ttcgccccgg cccatttcct atctaaaggg atcctcggga    480
```

-continued

```
ggccccctgc tctgtcccat gggacatgcc gtgggcattt tcagggccgc ggtgtgcacc    540
cgtggggtcg caaaggcggt cgactttgtg cccgttgagt ccttagagac caccatgagg    600
tccccagtgt ttactgacaa ttccagccct ctaacagtgc cccagagtta ccaggtggcg    660
catctacatg cacccactgg gagtggcaag agcacgaagg tgccggccgc ttacgcagct    720
caggggtaca aggtacttgt gctgaacccg tctgttgctg ccaccttagg gttcggtgct    780
tatatgtcaa aggcccatgg gatcgaccca aacatcagga ccggcgtgag gaccatcacc    840
acaggctccc ccatcaccta ctccacctac ggcaaatttt tggctgatgg cggatgccca    900
ggaggtgcgt acgacatcat aatatgtgac gaatgtcact cagtggacgc cacctcgatt    960
ctgggcatag ggaccgtctt ggaccaagcg gagacggcgg gggtcaggct cactgtcctc   1020
gccaccgcta caccacctgg ttccgtcacc gtgccacatt ccaacatcga ggaagttgca   1080
ctgtccgctg acggggaaat accattttat ggtaaggcca tcccccctaaa ctacatcaag   1140
ggggggaggc acctcatttt ctgccactcc aagaagaagt gcgacgagct cgctgcaaag   1200
ctggtcggtc cgggcgtcaa cgcggtggcc ttttaccgtg gcctcgacgt atctgtcatt   1260
ccaactacag gagacgtcgt tgttgtagcg accgacgcct tgatgactgg cttcaccgga   1320
gatttcgact ctgtgataga ctgcaacacc tgtgtcgtcc agacagtcga cttcagccta   1380
gaccctatat tctctattga gacttccacc gtgccccagg acgccgtgtc ccgctcccaa   1440
cggaggggta ggaccggtcg agggaagcat ggtatttaca gatatgtgtc acccggggag   1500
cggccgtctg gcatgttcga ctccgtggtc ctctgtgagt gctatgacgc gggttgtgct   1560
tggtacgagc ttacacccgc cgagaccaca gtcaggctac gggcatacct caacacccca   1620
ggattgcccg tgtgccagga ccacttggag ttctgggaga gtgtcttcac cggcctcacc   1680
cacatagatg cccacttcct gtcccagacg aaacagagtg ggagaacttt cccctaccta   1740
gtcgcatacc aagccaccgt gtgcgctaga gctagagctc ctcccccgtc atgggaccaa   1800
atgtggaagt gcctgatacg gctcaagccc accctcactg ggctacccc attactatac   1860
agactgggta gtgtacagaa tgagatcacc ttaacacacc caatcaccca atacatcatg   1920
gcttgcatgt cggcggacct ggaggtcgtc act                                1953
```

<210> SEQ ID NO 14
<211> LENGTH: 651
<212> TYPE: PRT
<213> ORGANISM: Hepatitis C virus

<400> SEQUENCE: 14

```
Gly Gln Glu Ile Leu Leu Gly Pro Ala Asp Gly Met Ala Ser Arg Gly
1               5                   10                  15

Trp Arg Leu Leu Ala Pro Ile Thr Ala Tyr Ala Gln Gln Thr Arg Gly
            20                  25                  30

Leu Leu Gly Cys Ile Ile Thr Ser Leu Thr Gly Arg Asp Lys Asn Gln
        35                  40                  45

Val Glu Gly Glu Val Gln Ile Val Ser Thr Ala Ala Gln Thr Phe Leu
    50                  55                  60

Ala Thr Cys Ile Asn Gly Val Cys Trp Thr Val Tyr His Gly Ala Gly
65                  70                  75                  80

Thr Arg Thr Ile Ala Ser Ser Lys Gly Pro Val Ile Leu Met Tyr Thr
                85                  90                  95

Asn Val Asp Gln Asp Leu Gly Gly Trp Thr Ala Pro Gln Val Leu Gly
            100                 105                 110
```

-continued

```
Ser Leu Thr Pro Trp Ser Cys Gly Ser Ser Asp Leu Tyr Leu Val Thr
        115                 120                 125

Arg His Ala Asp Val Ile Pro Val Pro Arg Arg Gly Glu Thr Arg Gly
    130                 135                 140

Ser Leu Leu Ser Pro Arg Pro Ile Ser Tyr Leu Lys Gly Ser Ser Gly
145                 150                 155                 160

Gly Pro Leu Leu Cys Pro Met Gly His Ala Val Gly Ile Phe Arg Ala
                165                 170                 175

Ala Val Cys Thr Arg Gly Val Ala Lys Ala Val Asp Phe Val Pro Val
            180                 185                 190

Glu Ser Leu Glu Thr Thr Met Arg Ser Pro Val Phe Thr Asp Asn Ser
        195                 200                 205

Ser Pro Leu Thr Val Pro Gln Ser Tyr Gln Val Ala His Leu His Ala
    210                 215                 220

Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255

Gly Phe Gly Ala Tyr Met Ser Lys Ala His Gly Ile Asp Pro Asn Ile
            260                 265                 270

Arg Thr Gly Val Arg Thr Ile Thr Thr Gly Ser Pro Ile Thr Tyr Ser
        275                 280                 285

Thr Tyr Gly Lys Phe Leu Ala Asp Gly Gly Cys Pro Gly Gly Ala Tyr
    290                 295                 300

Asp Ile Ile Ile Cys Asp Glu Cys His Ser Val Asp Ala Thr Ser Ile
305                 310                 315                 320

Leu Gly Ile Gly Thr Val Leu Asp Gln Ala Glu Thr Ala Gly Val Arg
                325                 330                 335

Leu Thr Val Leu Ala Thr Ala Thr Pro Pro Gly Ser Val Thr Val Pro
            340                 345                 350

His Ser Asn Ile Glu Glu Val Ala Leu Ser Ala Asp Gly Glu Ile Pro
        355                 360                 365

Phe Tyr Gly Lys Ala Ile Pro Leu Asn Tyr Ile Lys Gly Gly Arg His
    370                 375                 380

Leu Ile Phe Cys His Ser Lys Lys Lys Cys Asp Glu Leu Ala Ala Lys
385                 390                 395                 400

Leu Val Gly Pro Gly Val Asn Ala Val Ala Phe Tyr Arg Gly Leu Asp
                405                 410                 415

Val Ser Val Ile Pro Thr Thr Gly Asp Val Val Val Val Ala Thr Asp
            420                 425                 430

Ala Leu Met Thr Gly Phe Thr Gly Asp Phe Asp Ser Val Ile Asp Cys
        435                 440                 445

Asn Thr Cys Val Val Gln Thr Val Asp Phe Ser Leu Asp Pro Ile Phe
    450                 455                 460

Ser Ile Glu Thr Ser Thr Val Pro Gln Asp Ala Val Ser Arg Ser Gln
465                 470                 475                 480

Arg Arg Gly Arg Thr Gly Arg Gly Lys His Gly Ile Tyr Arg Tyr Val
                485                 490                 495

Ser Pro Gly Glu Arg Pro Ser Gly Met Phe Asp Ser Val Val Leu Cys
            500                 505                 510

Glu Cys Tyr Asp Ala Gly Cys Ala Trp Tyr Glu Leu Thr Pro Ala Glu
        515                 520                 525

Thr Thr Val Arg Leu Arg Ala Tyr Leu Asn Thr Pro Gly Leu Pro Val
```

-continued

```
    530                 535                 540

Cys Gln Asp His Leu Glu Phe Trp Glu Ser Val Phe Thr Gly Leu Thr
545                 550                 555                 560

His Ile Asp Ala His Phe Leu Ser Gln Thr Lys Gln Ser Gly Glu Asn
                565                 570                 575

Phe Pro Tyr Leu Val Ala Tyr Gln Ala Thr Val Cys Ala Arg Ala Arg
            580                 585                 590

Ala Pro Pro Pro Ser Trp Asp Gln Met Trp Lys Cys Leu Ile Arg Leu
        595                 600                 605

Lys Pro Thr Leu Thr Gly Ala Thr Pro Leu Leu Tyr Arg Leu Gly Ser
    610                 615                 620

Val Gln Asn Glu Ile Thr Leu Thr His Pro Ile Thr Gln Tyr Ile Met
625                 630                 635                 640

Ala Cys Met Ser Ala Asp Leu Glu Val Val Thr
                645                 650


<210> SEQ ID NO 15
<211> LENGTH: 945
<212> TYPE: DNA
<213> ORGANISM: Hepatitis C virus

<400> SEQUENCE: 15

agcacgtggg tgttggtggg cggcgtccta gccgctttgg ccgcttactg cctgtccaca     60

ggcagcgtgg tcatagtggg caggataatc ctaggtggga agccggcagt catacctgac    120

agggaggttc tctaccgaga gtttgatgag atggaggagt gcgccgccca cgtcccctac    180

ctcgagcagg ggatgcattt ggcggagcag ttcaagcaga aagctcttgg gttgctccag    240

acggcatcca aacaaacaga gacgatcact cccattgtcc agtctaattg gcagaagctc    300

gagtctttct gggctaaaca catgtggaac ttcgttagcg ggatacaata tctggcgggc    360

ctatcaacgc tgcccgggaa ccccgctata gcatcgctga tgtcgtttac ggccgcagtg    420

acgagtccac taaccactca gcagaccctc ctctttaaca tcttgggggg gtggctggct    480

gcccagcttg ccgccccagc cgccgccaca gccttcgttg gcgcaggcat tactggcgcc    540

gttgttggca gtgtgggcct agggaaggtc ctggtggaca ttcttgccgg ctacggggct    600

ggtgtggccg gggccctcgt ggctttcaaa atcatgagcg gggagacccc caccacggag    660

gatctagtca accttctgcc tgccatccta tcgccaggag ctctcgttgt cgccgtggtg    720

tgcgcagcaa tactacgccg gcacgtgggc cttggcgagg gcgccgtgca gtggatgaac    780

cggctgatag cgtttgcttc tcggggtaac cacgtctccc ctacacacta cgtgccggag    840

agcgacgcgt cggctcgtgt cacaccaatt ctcaccaggc tcactgttac tcagcttctg    900

aaagggctcc acgtgtggat aagctcgaat tgcatcgccc cgtgt                    945


<210> SEQ ID NO 16
<211> LENGTH: 315
<212> TYPE: PRT
<213> ORGANISM: Hepatitis C virus

<400> SEQUENCE: 16

Ser Thr Trp Val Leu Val Gly Gly Val Leu Ala Ala Leu Ala Ala Tyr
1               5                   10                  15

Cys Leu Ser Thr Gly Ser Val Val Ile Val Gly Arg Ile Ile Leu Gly
            20                  25                  30

Gly Lys Pro Ala Val Ile Pro Asp Arg Glu Val Leu Tyr Arg Glu Phe
        35                  40                  45
```

-continued

```
Asp Glu Met Glu Glu Cys Ala Ala His Val Pro Tyr Leu Glu Gln Gly
    50                  55                  60

Met His Leu Ala Glu Gln Phe Lys Gln Lys Ala Leu Gly Leu Leu Gln
65                  70                  75                  80

Thr Ala Ser Lys Gln Thr Glu Thr Ile Thr Pro Ile Val Gln Ser Asn
                85                  90                  95

Trp Gln Lys Leu Glu Ser Phe Trp Ala Lys His Met Trp Asn Phe Val
            100                 105                 110

Ser Gly Ile Gln Tyr Leu Ala Gly Leu Ser Thr Leu Pro Gly Asn Pro
        115                 120                 125

Ala Ile Ala Ser Leu Met Ser Phe Thr Ala Ala Val Thr Ser Pro Leu
    130                 135                 140

Thr Thr Gln Gln Thr Leu Leu Phe Asn Ile Leu Gly Gly Trp Leu Ala
145                 150                 155                 160

Ala Gln Leu Ala Ala Pro Ala Ala Ala Thr Ala Phe Val Gly Ala Gly
                165                 170                 175

Ile Thr Gly Ala Val Val Gly Ser Val Gly Leu Gly Lys Val Leu Val
            180                 185                 190

Asp Ile Leu Ala Gly Tyr Gly Ala Gly Val Ala Gly Ala Leu Val Ala
        195                 200                 205

Phe Lys Ile Met Ser Gly Glu Thr Pro Thr Thr Glu Asp Leu Val Asn
    210                 215                 220

Leu Leu Pro Ala Ile Leu Ser Pro Gly Ala Leu Val Val Ala Val Val
225                 230                 235                 240

Cys Ala Ala Ile Leu Arg Arg His Val Gly Leu Gly Glu Gly Ala Val
                245                 250                 255

Gln Trp Met Asn Arg Leu Ile Ala Phe Ala Ser Arg Gly Asn His Val
            260                 265                 270

Ser Pro Thr His Tyr Val Pro Glu Ser Asp Ala Ser Ala Arg Val Thr
        275                 280                 285

Pro Ile Leu Thr Arg Leu Thr Val Thr Gln Leu Leu Lys Gly Leu His
    290                 295                 300

Val Trp Ile Ser Ser Asn Cys Ile Ala Pro Cys
305                 310                 315


<210> SEQ ID NO 17
<211> LENGTH: 3117
<212> TYPE: DNA
<213> ORGANISM: Hepatitis C virus

<400> SEQUENCE: 17

gctagttctt ggcttaaaga tgtctggaac tggatatgcg aggtgctgag cgacttcaag     60

aattggctga aggccaaact tgtaccacaa ctgcccggga tcccattcgt atcctgccaa    120

cgcgggtacc gtggggtctg gcggggcgag ggcatcgtgc acactcgttg cccgtgtggg    180

gccaatataa ctggacatgt caagaacggt tcgatgagaa tcgtcgggcc taagacttgc    240

agcaacacct ggcgtgggtc gttccccatt aacgcttaca ctacaggccc gtgcacgccc    300

tccccggcgc cgaactatac gttcgcgcta tggagggtgt ctgcagagga gtatgtggag    360

gtaaggcggc tgggggactt ccattacgtc acgggggtga ccactgataa actcaagtgt    420

ccatgccagg tcccctcacc cgagttctcc acagaggtgg acggggtgcg cctgcatagg    480

tacgcccctc cctgcaaacc cctgctacgg gatgaggtga cgtttagcgt cgggttcaat    540

gaatacctgg tggggtccca gttgccctgc gagcccgagc cagacgtagc agcattaaca    600
```

-continued

```
tcaatgctta cagacccttc ccacatcact gcaaagacgg cggcgcgtag gctgaagcgg    660
gggtctcccc cctccctggc cagttcttct gccagccagc tgtccgcgcc gtcactgaaa    720
gcaacatgca ccactcacca tgactctcca gacgccgacc tcatagaagc caacctcctg    780
tggagacggg agatgggggg gaacatcacc agagtggagt cggagaacaa gattgttgtt    840
ctggattctt tcgacccgct cgtggcagag gaggatgacc gggagatttc tattccagct    900
gagattctgc ggaaatttaa gcagtttccc cccgccatgc ccatatgggc acggccggat    960
tataatcctc cccttgtgga accgtggaag cgcccggact gtgatccacc cttagtccac   1020
gggtgccccc taccacctcc caagccgact ccggtgccgc caccccggaa aaagaggacg   1080
gtggtgctgg acgagtctac agtatcatct gctctggctg agcttgccac taagaccttc   1140
ggcagctcta caacctcagg cgtgacaagt ggtgaagcgg ccgaatcgtc cccggcgctt   1200
tcctgcgacg gtgagctgga ctccgaagct gaatcttact cctccatgcc ccctctcgag   1260
ggggaaccgg gggaccccga tctcagcgac gggtcttggt ctaccgtgag cagtgatggc   1320
ggtacggagg atgtcgtgtg ctgctcgatg tcctactcgt ggacgggcgc cttaattacg   1380
ccctgtgccg cagaggaaac caaactcccc atcaacgcac tgagtaactc gctgctgcgc   1440
caccacaatt tggtgtattc caccacctct cgcagcgctg gcaagaggca gaaaaaagtc   1500
acatttgaca ggctgcaggt cctggacgat cattaccggg acgtgctcaa ggaggctaag   1560
gccaaggcat ccacagtgaa ggctaaattg ctatccgtag aggaggcatg tagcctgacg   1620
cccccgcact ccgccagatc aaaatttggc tatgggccga aggatgtccg aagccattcc   1680
agtaaggcta tacgccacat caactccgtg tggcaggacc ttctggagga caatacaaca   1740
cctatagaca ctaccatcat ggccaagaat gaagtcttct gcgtgaaggc cgaaaaaggg   1800
ggtcgcaagc ccgctcgcct tatcgtgtac cccgacctgg gggtgcgcgt gtgcgagaag   1860
agagctttgt atgacgtagt caaacagctc cccattgccg tgatgggacc ctcctacggg   1920
ttccagtact cgccagcgca gcgggtcgac ttcctgctta acgcgtggaa atcaaagaaa   1980
aaccctatgg ggttttccta tgacacccgt tgctttgact caacagtcac tgaggctgat   2040
atccgtacgg aggaagacct ctatcaatct tgtgacctgg tccctgaggc ccgcgcggcc   2100
ataaggtctc tcacagagag gctttacatc gggggcccac ttaccaattc taagggacaa   2160
aactgcggct atcggcgatg ccgcgcaagc ggcgtgctga ccactagctg cggtaacacc   2220
ataacttgct accttaaggc tagtgcggcc tgtcgagctg caaagctcca ggactgcacc   2280
atgctcgtgt gcggcgacga cctcgtcgtt atctgtgaaa gcgccggtgt caaggaggac   2340
gctgcgagcc tgagagcctt caccgaggct atgaccaggt actccggccc cccgggagac   2400
ccggctcaac cagaatacga cttggagctt ataacatcct gctcctccaa tgtgtcggtc   2460
gcgcgcgacg gcgctggcca aagggtctat tatctgaccc gtgaacctga gactcccctc   2520
gcgcgtgccg cttgggagac agcaagacac actccagtga actcctggct aggcaacatc   2580
atcatgtttg cccccactct gtgggtacgg atggtcctca tgacccactt attctccata   2640
ctcatagttc aggagcacct tgaaaaggct ctagattgtg aaatctatgg agccacacac   2700
tccgtcccac cgttggacct acctgaaatc attcaaagac tccatggcct cagcgcgttt   2760
tcgctccaca gttactctcc aggtgaaatc aatagggtgg cttcatgcct caggaaactt   2820
ggggttccac ccttgcgagc ttggagacac cgggcccgga gcgtccgcgc cacactccta   2880
tcccaggggg ggaaagccgc catatgcggt aagtacctct tcaactgggc ggtgaaaacc   2940
```

-continued

```
aaactcaaac tcattccatt accgctcgcg tctcatttgg acttgtccaa ttggttcacg   3000

ggcggctaca gcgggggaga catttatcac agcgtgtctc atgcccggcc ccgttggttt   3060

ctctggtgcc tactcctact ctcagtaggg gtaggcatct acctccttcc caaccga      3117


<210> SEQ ID NO 18
<211> LENGTH: 1039
<212> TYPE: PRT
<213> ORGANISM: Hepatitis C virus

<400> SEQUENCE: 18

Ala Ser Ser Trp Leu Lys Asp Val Trp Asn Trp Ile Cys Glu Val Leu
1               5                   10                  15

Ser Asp Phe Lys Asn Trp Leu Lys Ala Lys Leu Val Pro Gln Leu Pro
            20                  25                  30

Gly Ile Pro Phe Val Ser Cys Gln Arg Gly Tyr Arg Gly Val Trp Arg
        35                  40                  45

Gly Glu Gly Ile Val His Thr Arg Cys Pro Cys Gly Ala Asn Ile Thr
    50                  55                  60

Gly His Val Lys Asn Gly Ser Met Arg Ile Val Gly Pro Lys Thr Cys
65                  70                  75                  80

Ser Asn Thr Trp Arg Gly Ser Phe Pro Ile Asn Ala Tyr Thr Thr Gly
                85                  90                  95

Pro Cys Thr Pro Ser Pro Ala Pro Asn Tyr Thr Phe Ala Leu Trp Arg
            100                 105                 110

Val Ser Ala Glu Glu Tyr Val Glu Val Arg Arg Leu Gly Asp Phe His
        115                 120                 125

Tyr Val Thr Gly Val Thr Thr Asp Lys Leu Lys Cys Pro Cys Gln Val
    130                 135                 140

Pro Ser Pro Glu Phe Ser Thr Glu Val Asp Gly Val Arg Leu His Arg
145                 150                 155                 160

Tyr Ala Pro Pro Cys Lys Pro Leu Leu Arg Asp Glu Val Thr Phe Ser
                165                 170                 175

Val Gly Phe Asn Glu Tyr Leu Val Gly Ser Gln Leu Pro Cys Glu Pro
            180                 185                 190

Glu Pro Asp Val Ala Ala Leu Thr Ser Met Leu Thr Asp Pro Ser His
        195                 200                 205

Ile Thr Ala Lys Thr Ala Ala Arg Arg Leu Lys Arg Gly Ser Pro Pro
    210                 215                 220

Ser Leu Ala Ser Ser Ser Ala Ser Gln Leu Ser Ala Pro Ser Leu Lys
225                 230                 235                 240

Ala Thr Cys Thr Thr His His Asp Ser Pro Asp Ala Asp Leu Ile Glu
                245                 250                 255

Ala Asn Leu Leu Trp Arg Arg Glu Met Gly Gly Asn Ile Thr Arg Val
            260                 265                 270

Glu Ser Glu Asn Lys Ile Val Val Leu Asp Ser Phe Asp Pro Leu Val
        275                 280                 285

Ala Glu Glu Asp Asp Arg Glu Ile Ser Ile Pro Ala Glu Ile Leu Arg
    290                 295                 300

Lys Phe Lys Gln Phe Pro Pro Ala Met Pro Ile Trp Ala Arg Pro Asp
305                 310                 315                 320

Tyr Asn Pro Pro Leu Val Glu Pro Trp Lys Arg Pro Asp Cys Asp Pro
                325                 330                 335

Pro Leu Val His Gly Cys Pro Leu Pro Pro Pro Lys Pro Thr Pro Val
            340                 345                 350
```

-continued

```
Pro Pro Pro Arg Lys Lys Arg Thr Val Val Leu Asp Glu Ser Thr Val
        355                 360                 365

Ser Ser Ala Leu Ala Glu Leu Ala Thr Lys Thr Phe Gly Ser Ser Thr
    370                 375                 380

Thr Ser Gly Val Thr Ser Gly Glu Ala Ala Glu Ser Ser Pro Ala Leu
385                 390                 395                 400

Ser Cys Asp Gly Glu Leu Asp Ser Glu Ala Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Ser Asp Gly Gly Thr Glu Asp Val Val Cys Cys
        435                 440                 445

Ser Met Ser Tyr Ser Trp Thr Gly Ala Leu Ile Thr Pro Cys Ala Ala
    450                 455                 460

Glu Glu Thr Lys Leu Pro Ile Asn Ala Leu Ser Asn Ser Leu Leu Arg
465                 470                 475                 480

His His Asn Leu Val Tyr Ser Thr Thr Ser Arg Ser Ala Gly Lys Arg
                485                 490                 495

Gln Lys Lys Val Thr Phe Asp Arg Leu Gln Val Leu Asp Asp His Tyr
            500                 505                 510

Arg Asp Val Leu Lys Glu Ala Lys Ala Lys Ala Ser Thr Val Lys Ala
        515                 520                 525

Lys Leu Leu Ser Val Glu Glu Ala Cys Ser Leu Thr Pro Pro His Ser
    530                 535                 540

Ala Arg Ser Lys Phe Gly Tyr Gly Pro Lys Asp Val Arg Ser His Ser
545                 550                 555                 560

Ser Lys Ala Ile Arg His Ile Asn Ser Val Trp Gln Asp Leu Leu Glu
                565                 570                 575

Asp Asn Thr Thr Pro Ile Asp Thr Thr Ile Met Ala Lys Asn Glu Val
            580                 585                 590

Phe Cys Val Lys Ala Glu Lys Gly Gly Arg Lys Pro Ala Arg Leu Ile
        595                 600                 605

Val Tyr Pro Asp Leu Gly Val Arg Val Cys Glu Lys Arg Ala Leu Tyr
    610                 615                 620

Asp Val Val Lys Gln Leu Pro Ile Ala Val Met Gly Pro Ser Tyr Gly
625                 630                 635                 640

Phe Gln Tyr Ser Pro Ala Gln Arg Val Asp Phe Leu Leu Asn Ala Trp
                645                 650                 655

Lys Ser Lys Lys Asn Pro Met Gly Phe Ser Tyr Asp Thr Arg Cys Phe
            660                 665                 670

Asp Ser Thr Val Thr Glu Ala Asp Ile Arg Thr Glu Glu Asp Leu Tyr
        675                 680                 685

Gln Ser Cys Asp Leu Val Pro Glu Ala Arg Ala Ala Ile Arg Ser Leu
    690                 695                 700

Thr Glu Arg Leu Tyr Ile Gly Gly Pro Leu Thr Asn Ser Lys Gly Gln
705                 710                 715                 720

Asn Cys Gly Tyr Arg Arg Cys Arg Ala Ser Gly Val Leu Thr Thr Ser
                725                 730                 735

Cys Gly Asn Thr Ile Thr Cys Tyr Leu Lys Ala Ser Ala Ala Cys Arg
            740                 745                 750

Ala Ala Lys Leu Gln Asp Cys Thr Met Leu Val Cys Gly Asp Asp Leu
        755                 760                 765
```

-continued

```
Val Val Ile Cys Glu Ser Ala Gly Val Lys Glu Asp Ala Ala Ser Leu
    770                 775                 780

Arg Ala Phe Thr Glu Ala Met Thr Arg Tyr Ser Gly Pro Pro Gly Asp
785                 790                 795                 800

Pro Ala Gln Pro Glu Tyr Asp Leu Glu Leu Ile Thr Ser Cys Ser Ser
                805                 810                 815

Asn Val Ser Val Ala Arg Asp Gly Ala Gly Gln Arg Val Tyr Tyr Leu
            820                 825                 830

Thr Arg Glu Pro Glu Thr Pro Leu Ala Arg Ala Ala Trp Glu Thr Ala
        835                 840                 845

Arg His Thr Pro Val Asn Ser Trp Leu Gly Asn Ile Ile Met Phe Ala
    850                 855                 860

Pro Thr Leu Trp Val Arg Met Val Leu Met Thr His Leu Phe Ser Ile
865                 870                 875                 880

Leu Ile Val Gln Glu His Leu Glu Lys Ala Leu Asp Cys Glu Ile Tyr
                885                 890                 895

Gly Ala Thr His Ser Val Pro Pro Leu Asp Leu Pro Glu Ile Ile Gln
            900                 905                 910

Arg Leu His Gly Leu Ser Ala Phe Ser Leu His Ser Tyr Ser Pro Gly
        915                 920                 925

Glu Ile Asn Arg Val Ala Ser Cys Leu Arg Lys Leu Gly Val Pro Pro
    930                 935                 940

Leu Arg Ala Trp Arg His Arg Ala Arg Ser Val Arg Ala Thr Leu Leu
945                 950                 955                 960

Ser Gln Gly Gly Lys Ala Ala Ile Cys Gly Lys Tyr Leu Phe Asn Trp
                965                 970                 975

Ala Val Lys Thr Lys Leu Lys Leu Ile Pro Leu Pro Leu Ala Ser His
            980                 985                 990

Leu Asp Leu Ser Asn Trp Phe Thr  Gly Gly Tyr Ser Gly  Gly Asp Ile
        995                 1000                 1005

Tyr His  Ser Val Ser His Ala  Arg Pro Arg Trp Phe  Leu Trp Cys
    1010                 1015                 1020

Leu Leu  Leu Leu Ser Val Gly  Val Gly Ile Tyr Leu  Leu Pro Asn
    1025                 1030                 1035

Arg


<210> SEQ ID NO 19
<211> LENGTH: 18
<212> TYPE: DNA
<213> ORGANISM: Artificial Sequence
<220> FEATURE:
<223> OTHER INFORMATION: Synthetic HCV Primer

<400> SEQUENCE: 19

gccagccccc tatggggg                                                    18


<210> SEQ ID NO 20
<211> LENGTH: 24
<212> TYPE: DNA
<213> ORGANISM: Artificial Sequence
<220> FEATURE:
<223> OTHER INFORMATION: Synthetic HCV Primer

<400> SEQUENCE: 20

gtttaggatt cgtgctcatg gtgc                                             24


<210> SEQ ID NO 21
```

-continued

<211> LENGTH: 25
<212> TYPE: DNA
<213> ORGANISM: Artificial Sequence
<220> FEATURE:
<223> OTHER INFORMATION: Synthetic HCV Primer

<400> SEQUENCE: 21
gaccgtgcac catgagcacg aatcc 25

<210> SEQ ID NO 22
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 22
tccgacggcc gaagcgggca 20

<210> SEQ ID NO 23
<211> LENGTH: 24
<212> TYPE: DNA
<213> ORGANISM: Artificial Sequence
<220> FEATURE:
<223> OTHER INFORMATION: Synthetic HCV Primer

<400> SEQUENCE: 23
cccggttgct ctttctctat cttc 24

<210> SEQ ID NO 24
<211> LENGTH: 26
<212> TYPE: DNA
<213> ORGANISM: Artificial Sequence
<220> FEATURE:
<223> OTHER INFORMATION: Synthetic HCV Primer

<400> SEQUENCE: 24
ggatagatgg agcaattgca gtcttg 26

<210> SEQ ID NO 25
<211> LENGTH: 25
<212> TYPE: DNA
<213> ORGANISM: Artificial Sequence
<220> FEATURE:
<223> OTHER INFORMATION: Synthetic HCV Primer

<400> SEQUENCE: 25
caagactgca attgctccat ctatc 25

<210> SEQ ID NO 26
<211> LENGTH: 32
<212> TYPE: DNA
<213> ORGANISM: Artificial Sequence
<220> FEATURE:
<223> OTHER INFORMATION: Synthetic HCV Primer

<400> SEQUENCE: 26
agcctgtgct cgaccccccc cacatacatc ct 32

<210> SEQ ID NO 27
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 27

-continued

```
caactggatt caccaaggtg                                              20


<210> SEQ ID NO 28
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 28

gcagactggc ctgcaagatc                                              20


<210> SEQ ID NO 29
<211> LENGTH: 19
<212> TYPE: DNA
<213> ORGANISM: Artificial Sequence
<220> FEATURE:
<223> OTHER INFORMATION: Synthetic HCV Primer

<400> SEQUENCE: 29

acatcaccaa aatcatgct                                               19


<210> SEQ ID NO 30
<211> LENGTH: 18
<212> TYPE: DNA
<213> ORGANISM: Artificial Sequence
<220> FEATURE:
<223> OTHER INFORMATION: Synthetic HCV Primer

<400> SEQUENCE: 30

cccagtgggt gcgtaatg                                                18


<210> SEQ ID NO 31
<211> LENGTH: 33
<212> TYPE: DNA
<213> ORGANISM: Artificial Sequence
<220> FEATURE:
<223> OTHER INFORMATION: Synthetic HCV Primer

<400> SEQUENCE: 31

cgcggatccg tgtgcacccg tggggttgca aag                               33


<210> SEQ ID NO 32
<211> LENGTH: 35
<212> TYPE: DNA
<213> ORGANISM: Artificial Sequence
<220> FEATURE:
<223> OTHER INFORMATION: Synthetic HCV Primer

<400> SEQUENCE: 32

cgaggcttct agctagtgac gacctccagg tccgc                             35


<210> SEQ ID NO 33
<211> LENGTH: 33
<212> TYPE: DNA
<213> ORGANISM: Artificial Sequence
<220> FEATURE:
<223> OTHER INFORMATION: Synthetic HCV Primer

<400> SEQUENCE: 33

cgcggatccg cccactgccc ctacctcgag cag                               33


<210> SEQ ID NO 34
<211> LENGTH: 35
<212> TYPE: DNA
```

-continued

```
<213> ORGANISM: Artificial Sequence
<220> FEATURE:
<223> OTHER INFORMATION: Synthetic HCV Primer

<400> SEQUENCE: 34

cgaagcttct aagcacacgg ggcgatgcaa tccga                                 35


<210> SEQ ID NO 35
<211> LENGTH: 29
<212> TYPE: DNA
<213> ORGANISM: Artificial Sequence
<220> FEATURE:
<223> OTHER INFORMATION: Synthetic HCV Primer

<400> SEQUENCE: 35

ctgggactgg atatgcgagg tgctgagcg                                        29


<210> SEQ ID NO 36
<211> LENGTH: 28
<212> TYPE: DNA
<213> ORGANISM: Artificial Sequence
<220> FEATURE:
<223> OTHER INFORMATION: Synthetic HCV Primer

<400> SEQUENCE: 36

gagctgccaa ggtcttagtg gcaagctc                                         28


<210> SEQ ID NO 37
<211> LENGTH: 20
<212> TYPE: DNA
<213> ORGANISM: Artificial Sequence
<220> FEATURE:
<223> OTHER INFORMATION: Synthetic HCV Primer

<400> SEQUENCE: 37

tatgggcacg gccggattat                                                  20


<210> SEQ ID NO 38
<211> LENGTH: 22
<212> TYPE: DNA
<213> ORGANISM: Artificial Sequence
<220> FEATURE:
<223> OTHER INFORMATION: Synthetic HCV Primer

<400> SEQUENCE: 38

ttcattcttg gccatgatgg ta                                               22


<210> SEQ ID NO 39
<211> LENGTH: 22
<212> TYPE: DNA
<213> ORGANISM: Artificial Sequence
<220> FEATURE:
<223> OTHER INFORMATION: Synthetic HCV Primer

<400> SEQUENCE: 39

atagacacta ccatcatggc ca                                               22


<210> SEQ ID NO 40
<211> LENGTH: 21
<212> TYPE: DNA
<213> ORGANISM: Artificial Sequence
<220> FEATURE:
<223> OTHER INFORMATION: Synthetic HCV Primer

<400> SEQUENCE: 40

acggggccta aaggcctgga g                                                21
```

-continued

<210> SEQ ID NO 41
<211> LENGTH: 341
<212> TYPE: DNA
<213> ORGANISM: Hepatitis C Virus Isolate 1

<400> SEQUENCE: 41
gccagccccc tgatgggggc gacactccac catgaatcac tcccctgtga ggaactactg 60
tcttcacgca gaaagcgtct agccatggcg ttagtatgag tgtcgtgcag cctccaggac 120 ccccctccc gggagagcca tagtggtctg cggaaccggt gagtacaccg gaattgccag 180
gacgaccggg tcctttcttg gatcaacccg ctcaatgcct ggagatttgg gcgtgccccc 240
gcaagactgc tagccgagta gtgttgggtc gcgaaaggcc ttgtggtact gcctgatagg 300
gtgcttgcga gtgccccggg aggtctcgta gaccgtgcac c 341

<210> SEQ ID NO 42
<211> LENGTH: 573
<212> TYPE: DNA
<213> ORGANISM: Hepatitis C Virus Isolate 1

<400> SEQUENCE: 42
atgagcacga atcctaaacc tcaaaaaaaa aacaaacgta acaccaaccg tcgcccacag 60
gacgtcaagt tcccgggtgg cggtcagatc gttggtggag tttacttgtt gccgcgcagg 120
ggccctagat tgggtgtgcg cgcgacgaga aagacttccg agcggtcgca acctcgaggt 180
agacgtcagc ctatccccaa ggctcgtcgg cccgagggca ggacctgggc tcagcccggg 240
tacccttggc ccctctatgg caatgagggc tgcgggtggg cgggatggct cctgtctccc 300
cgtggctctc ggcctagctg gggccccaca gacccccggc gtaggtcgcg caatttgggt 360
aaggtcatcg ataccettac gtgcggcttc gccgacctca tggggtacat accgctcgtc 420
ggcgcccctc ttggaggcgc tgccagggcc ctggcgcatg gcgtccgggt tctggaagac 480
ggcgtgaact atgcaacagg gaaccttcct ggttgctctt tctctatctt ccttctggcc 540
ctgctctctt gcttgactgt gcccgcttcg gcc 573

<210> SEQ ID NO 43
<211> LENGTH: 571
<212> TYPE: DNA
<213> ORGANISM: Hepatitis C Virus Isolate 1

<400> SEQUENCE: 43
agtgcgcaac tccacggggc tttaccacgt caccaatgat tgccctaact cgagtattgt 60
gtacgaggcg gccgatgcca tcctgcacac tccggggtgc gtcccttgcg ttcgtgaggg 120
caacgcctcg aggtgttggg tggcgatgac ccctacggtg gccaccaggg atggcaaact 180
ccccgcgacg cagcttcgac gtcacatcga tctgcttgtc gggagcgcca ccctctgttc 240
ggccctctac gtgggggacc tatgcgggtc tgtctttctt gtcggccaac tgttcacctt 300
ctctcccagg cgccactgga cgacgcaagg ttgcaattgc tctatctatc ccggccatat 360
aacgggtcac cgcatggcat gggatatgat gatgaactgg tcccctacga cggcgttggt 420
aatggctcag ctgctccgga tcccacaagc catcttggac atgatcgctg gtgctcactg 480
gggagtcctg gcgggcatag cgtatttctc catggtgggg aactgggcga aggtcctggt 540
agtgctgctg ctatttgccg gcgtcgacgc g 571

<210> SEQ ID NO 44

-continued

<211> LENGTH: 1274
<212> TYPE: DNA
<213> ORGANISM: Hepatitis C Virus Isolate 1

<400> SEQUENCE: 44

```
acccacgtca ccgggggaag tgccggccac actgtgtctg gatttgttag cctcctcgca     60
ccaggcgcca agcagaacgt ccagctgatc aacaccaacg gcagttggca cctcaatagc    120
acggccctga actgcaatga tagcctcaac accggctggt tggcagggct tttctatcac    180
cacaagttca actcttcagg ctgtcctgag aggctagcca gctgccgacc ccttaccgat    240
tttgaccagg gctggggccc tatcagttat gccaacggaa gcggccccga ccagcgcccc    300
tactgctggc actacccccc aaaaccttgc ggtattgtgc ccgcgaagag tgtgtgtggt    360
ccggtatatt gcttcactcc cagccccgtg gtggtgggaa cgaccgacag gtcgggcgcg    420
cccacctaca gctggggtga aaatgatacg gacgtcttcg tccttaacaa taccaggcca    480
ccgctgggca attggttcgg ttgtacctgg atgaactcaa ctggattcac caaagtgtgc    540
ggagcgcctc cttgtgtcat cggaggggcg ggcaacaaca ccctgcactg ccccactgat    600
tgcttccgca agcatccgga cgccacatac tctcggtgcg gctccggtcc ctggatcaca    660
cccaggtgcc tggtcgacta cccgtatagg ctttggcatt atccttgtac catcaactac    720
accatattta aaatcaggat gtacgtggga ggggtcgaac acaggctgga agctgcctgc    780
aactggacgc ggggcgaacg ttgcgatctg gaagacaggg acaggtccga gctcagcccg    840
ttactgctga ccactacaca gtggcaggtc ctcccgtgtt ccttcacaac cctaccagcc    900
ttgtccaccg gcctcatcca cctccaccag aacattgtgg acgtgcagta cttgtacggg    960
gtggggtcaa gcatcgcgtc ctgggccatt aagtgggagt acgtcgttct cctgttcctt   1020
ctgcttgcag acgcgcgcgt ctgctcctgc ttgtggatga tgctactcat atcccaagcg   1080
gaggcggctt tggagaacct cgtaatactt aatgcagcat ccctggccgg gacgcacggt   1140
cttgtatcct tcctcgtgtt cttctgcttt gcatggtatt tgaagggtaa gtgggtgccc   1200
ggagcggtct ataccttcta cgggatgtgg cctctcctcc tgctcctgtt ggcgttgccc   1260
cagcgggcgt acgc                                                     1274
```

<210> SEQ ID NO 45
<211> LENGTH: 590
<212> TYPE: DNA
<213> ORGANISM: Hepatitis C virus

<400> SEQUENCE: 45

```
tggacacgga ggtggccgcg tcgtgtggcg gtgttgttct cgtcgggttg atggcgctga     60
ctctgtcacc atattacaag cgctatatca gctggtgctt gtggtggctt cagtattttc    120
tgaccagagt ggaagcgcaa ctgcacgtgt ggattccccc cctcaacgtc cgagggggc    180
gcgacgccgt catcttactc atgtgtgctg tacacccgac tctggtattt gacatcacca    240
aattgctgct ggccgtcttc ggaccccttt ggattcttca agccagtttg cttaaagtac    300
cctactttgt gcgcgtccaa ggccttctcc ggttctgcgc gttagcgcgg aagatgatcg    360
gaggccatta cgtgcaaatg gtcatcatta agttaggggc gcttactggc acctatgttt    420
ataaccatct cactcctctt cgggactggg cgcacaacgg cttgcgagat ctggccgtgg    480
ctgtagagcc agtcgtcttc tcccaaatgg agaccaagct catcacgtgg ggggcagata    540
ccgccgcgtg cggtgacatc atcaacggct tgcctgtttc cgcccgcagg               590
```

-continued

<210> SEQ ID NO 46
<211> LENGTH: 1952
<212> TYPE: DNA
<213> ORGANISM: Hepatitis C virus

<400> SEQUENCE: 46
ggccgggaga tactgctcgg gccagccgat ggaatggtct ccaaggggtg gaggttgctg 60
gcgcccatca cggcgtacgc ccagcagaca aggggcctcc tagggtgcat aatcaccagc 120
ctaactggcc gggacaaaaa ccaagtggag ggtgaggtcc agattgtgtc aactgctgcc 180
caaaccttcc tggcaacgtg catcaatggg gtgtgctgga ctgtctacca cggggccgga 240
acgaggacca tcgcgtcacc caagggtcct gtcatccaga tgtataccaa tgtagaccaa 300
gaccttgtgg gctggcccgc tccgcaaggt agccgctcat tgacaccctg cacttgcggc 360
tcctcggacc tttacctggt cacgaggcac gccgatgtca ttcccgtgcg ccggcggggt 420
gatagcaggg gcagcctgct gtcgccccgg cccatttcct acttgaaagg ctcctcgggg 480
ggtccgctgt tgtgccccgc ggggcacgcc gtgggcatat ttagggccgc ggtgtgcacc 540
cgtggagtgg ctaaggcggt ggactttatc cctgtggaga acctagagac aaccatgagg 600
tccccggtgt tcacggataa ctcctctcca ccagtagtgc cccagagctt ccaggtggct 660
cacctccatg ctcccacagg cagcggcaaa agcaccaagg tcccggctgc atatgcagct 720
cagggctata aggtgctagt actcaacccc tctgttgctg caacactggg ctttggtgct 780
tacatgtcca aggctcatgg gatcgatcct aacatcagga ccggggtgag aacaattacc 840
actggcagcc ccatcacgta ctccacctac ggcaagttcc ttgccgacgg cgggtgctcg 900
gggggcgctt atgacataat aatttgtgac gagtgccact ccacggatgc cacatccatc 960
ttgggcatcg gcactgtcct tgaccaagca gagactgcgg gggcgagact ggttgtgctc 1020
gccaccgcca cccctccggg ctccgtcact gtgccccatc ccaacatcga ggaggttgct 1080
ctgtccacca ccggagagat cccttttttac ggcaaggcta tccccctcga agtaatcaag 1140
ggggggagac atctcatctt ctgtcattca aagaagaagt gcgacgaact cgccgcaaag 1200
ctggtcgcat tgggcatcaa tgccgtggcc tactaccgcg gtcttgacgt gtccgtcatc 1260
ccgaccagcg gcgatgttgt cgtcgtggca accgatgccc tcatgaccgg ctataccggc 1320
gacttcgact cggtgataga ctgcaatacg tgtgtcaccc agacagtcga tttcagcctt 1380
gaccctacct tcaccattga gacaatcacg ctcccccagg atgctgtctc ccgcactcaa 1440
cgtcggggca ggactggcag gggaagcca ggcatctaca gatttgtggc accgggggag 1500
cgcccctccg gcatgttcga ctcgtccgtc ctctgtgagt gctatgacgc aggctgtgct 1560
tggtatgagc tcacgcccgc cgagactaca gttaggctac gagcgtacat gaacaccccg 1620
gggcttcccg tgtgccagga ccatcttgaa ttttgggagg gcgtctttac aggcctcact 1680
catatagatg cccactttct atcccagaca aagcagagtg ggagaacct tccttacctg 1740 gtagcgtacc aagccaccgt gtgcgctagg gctcaagccc ctcccccatc gtgggaccag 1800
atgtggaagt gtttgattcg cctcaagccc accctccatg ggccaacacc cctgctatac 1860
agactgggcg ctgttcagaa tgaaatcacc ctgacgcacc cagtcaccaa atacatcatg 1920
acatgcatgt cggccgacct ggaggtcgtc ac 1952

<210> SEQ ID NO 47
<211> LENGTH: 944
<212> TYPE: DNA
<213> ORGANISM: Hepatitis C virus Isolate 1

-continued

<400> SEQUENCE: 47
agcacctggg tgctcgttgg cggcgtcctg gctgctttgg ccgcgtattg cctgtcaaca 60
ggctgcgtgg tcatagtggg cagggtcgtc ttgtccggga agccggcaat catacctgac 120
agggaagtcc tctaccgaga gttcgatgag atggaagagt gctctcagca cttaccgtac 180
atcgagcaag ggatgatgct cgccgagcag ttcaagcaga aggccctcgg cctcctgcag 240
accgcgtccc gtcaggcaga ggttatcgcc cctgctgtcc agaccaactg gcaaaaactc 300
gagaccttct gggcgaagca tatgtggaac ttcatcagtg ggatacaata cttggcgggc 360
ttgtcaacgc tgcctggtaa ccccgccatt gcttcattga tggcttttac agctgctgtc 420
accagcccac taaccactag ccaaaccctc ctcttcaaca tattgggggg gtgggtggct 480
gcccagctcg ccgcccccgg tgccgctact gcctttgtgg gcgctggctt agctggcgcc 540
gccatcggca gtgttggact ggggaaggtc ctcatagaca tccttgcagg gtatggcgcg 600
ggcgtggcgg gagctcttgt ggcattcaag atcatgagcg gtgaggtccc ctccacggag 660
gacctggtca atctactgcc cgccatcctc tcgcccggag ccctcgtagt cggcgtggtc 720
tgtgcagcaa tactgcgccg gcacgttggc ccgggcgagg gggcagtgca gtggatgaac 780
cggctgatag ccttcgcctc ccgggggaac catgtttccc ccacgcacta cgtgccggag 840
agcgatgcag ctgcccgcgt cactgccata ctcagcagcc tcactgtaac ccagctcctg 900
aggcgactgc accagtggat aagctcggag tgtaccactc catg 944

<210> SEQ ID NO 48
<211> LENGTH: 3113
<212> TYPE: DNA
<213> ORGANISM: Hepatitis C Virus Isolate 1

<400> SEQUENCE: 48
gttcctggct aagggacatc tgggactgga tatgcgaggt gttgagcgac tttaagacct 60
ggctaaaagc taagctcatg ccacagctgc ctgggatccc ctttgtgtcc tgccagcgcg 120
ggtataaggg ggtctggcga gtggacggca tcatgcacac tcgctgccac tgtggagctg 180
agatcactgg acatgtcaaa aacgggacga tgaggatcgt cggtcctagg acctgcagga 240
acatgtggag tgggaccttc cccattaatg cctacaccac gggcccctgt accccccttc 300
ctgcgccgaa ctacacgttc gcgctatgga gggtgtctgc agaggaatat gtggagataa 360
ggcaggtggg ggacttccac tacgtgacgg gtatgactac tgacaatctc aaatgcccgt 420
gccaggtccc atcgcccgaa tttttcacag aattggacgg ggtgcgccta cataggtttg 480
cgccccccctg caagcccttg ctgcgggagg aggtatcatt cagagtagga ctccacgaat 540
acccggtagg gtcgcaatta ccttgcgagc ccgaaccgga cgtggccgtg ttgacgtcca 600
tgctcactga tccctcccat ataacagcag aggcggccgg gcgaaggttg gcgaggggat 660
caccccccctc tgtggccagc tcctcggcta gccagctatc cgctccatct ctcaaggcaa 720
cttgcaccgc taaccatgac tcccctgatg ctgagctcat agaggccaac ctcctatgga 780
ggcaggagat gggcggcaac atcaccaggg ttgagtcaga aaacaaagtg gtgattctgg 840
actccttcga tccgcttgtg gcggaggagg acgagcggga gatctccgta cccgcagaaa 900
tcctgcggaa gtctcggaga ttcgcccagg ccctgcccgt ttgggcgcgg ccggactata 960
acccccccgct agtggagacg tggaaaaagc ccgactacga accacctgtg gtccatggct 1020
gtccgcttcc acctccaaag tcccctcctg tgcctccgcc tcggaagaag cggacggtgg 1080
tcctcactga atcaacccta tctactgcct tggccgagct cgccaccaga agctttggca 1140

```
gctcctcaac ttccggcatt acgggcgaca atacgacaac atcctctgag cccgcccctt   1200

ctggctgccc ccccgactcc gacgctgagt cctattcctc catgcccccc ctggaggggg   1260

agcctgggga tccggatctt agcgacgggt catggtcaac ggtcagtagt gaggccaacg   1320

cggaggatgt cgtgtgctgc tcaatgtctt actcttggac aggcgcactc gtcaccccgt   1380

gcgccgcgga agaacagaaa ctgcccatca atgcactaag caactcgttg ctacgtcacc   1440

acaatttggt gtattccacc acctcacgca gtgcttgcca aaggcagaag aaagtcacat   1500

ttgacagact gcaagttctg gacagccatt accaggacgt actcaaggag gttaaggcag   1560

cggcgtcaaa agtgaaggct aacttgctat ccgtagagga agcttgcagc ctgacgcccc   1620

cacactcagc caaatccaag tttggttatg ggcaaaaaga cgtccgttgc catgccagaa   1680

aggccgtaag ccacatcaac tccgtgtgga aagaccttct ggaagacaat gtaacaccaa   1740

tagacactac catcatggct aagaacgagg ttttctgcgt tcagcctgag aagggggtc    1800

gtaagccagc tcgtctcatc gtgttccccg atctgggcgt gcgcgtgtgc gaaaagagag   1860

ctttgtacga cgtggttaca aagctcccct tggccgtgat gggaagctcc tacggattcc   1920

aatactcacc aggacagcgg gttgaattcc tcgtgcacgc gtggaagtcc aagaaaaccc   1980

caatggggtt ctcgtatgat acccgctgct ttgactccac agtcactgag agcgacatcc   2040

gtacggagga ggcaatctac caatgttgtg acctcgaccc ccaagcccgc gtggccatca   2100

agtccctcac cgagaggctt tatgttgggg gccctcttac caattcaagg ggggagaact   2160

gcggctatcg caggtgccgc gcgagcggcg tactgacaac tagctgtggt aacaccctca   2220

cttgctacat caaggcccgg gcagcctgtc gagccgcagg gctccaggac tgcaccatgc   2280

tcgtgtgtgg cgacgactta gtcgttatct gtgaaagcgc gggggtccag gaggacgcgg   2340

cgagcctgag agccttcacg gaggctatga ccaggtactc cgcccccct ggggaccccc    2400

cacaaccaga atacgacttg gagctcataa catcatgctc ctccaacgtg tcagtcgcga   2460

acgacggcgc tggaaagagg gtctactacc tcacccgtga ccctacaacc cccctcgcga   2520

gagctgcgtg ggagacagca agacacactc cagtcaattc ctggctaggc aacataatca   2580

tgtttgcccc cacactgtgg gcgaggatga tactgatgac ccatttcttt agcgtcctta   2640

tagccaggga ccagcttgaa caggccctcg attgcgagat ctacggggcc tgctactcca   2700

tagaaccact tgatctacct ccaatcattc aaagactcca tggcctcagc gcattttcac   2760

tccacagtta ctctccaggt gaaattaata gggtggccgc atgcctcaga aaacttgggg   2820

taccgccctt gcgagcttgg agacaccggg cccggagcgt ccgcgctagg cttctggcca   2880

gaggaggcag ggctgccata tgtggcaagt acctcttcaa ctgggcagta agaacaaagc   2940

tcaaactcac tccaatagcg gccgctggcc agctggactt gtccggctgg ttcacggctg   3000

gctacagcgg gggagacatt tatcacagcg tgtctcatgc ccggccccgc tggatctggt   3060

tttgcctact cctgcttgca gcaggggtag gcatctacct cctccccaac cga          3113
```

<210> SEQ ID NO 49
<211> LENGTH: 26
<212> TYPE: DNA
<213> ORGANISM: Hepatitis C Virus Isolate 1

<400> SEQUENCE: 49

```
gaaggttggg gtaaacactc cggcct                                          26
```

<210> SEQ ID NO 50

-continued

<211> LENGTH: 191
<212> TYPE: PRT
<213> ORGANISM: Hepatitis C Virus Isolate 1

<400> SEQUENCE: 50

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 51
<211> LENGTH: 190
<212> TYPE: PRT
<213> ORGANISM: Hepatitis C Virus Isolate 1

<400> SEQUENCE: 51

```
Val Arg Asn Ser Thr Gly Leu Tyr His Val Thr Asn Asp Cys Pro Asn
1               5                   10                  15

Ser Ser Ile Val Tyr Glu Ala Ala Asp Ala Ile Leu His Thr Pro Gly
            20                  25                  30

Cys Val Pro Cys Val Arg Glu Gly Asn Ala Ser Arg Cys Trp Val Ala
        35                  40                  45

Met Thr Pro Thr Val Ala Thr Arg Asp Gly Lys Leu Pro Ala Thr Gln
    50                  55                  60

Leu Arg Arg His Ile Asp Leu Leu Val Gly Ser Ala Thr Leu Cys Ser
65                  70                  75                  80

Ala Leu Tyr Val Gly Asp Leu Cys Gly Ser Val Phe Leu Val Gly Gln
                85                  90                  95

Leu Phe Thr Phe Ser Pro Arg Arg His Trp Thr Thr Gln Gly Cys Asn
            100                 105                 110

Cys Ser Ile Tyr Pro Gly His Ile Thr Gly His Arg Met Ala Trp Asp
        115                 120                 125

Met Met Met Asn Trp Ser Pro Thr Thr Ala Leu Val Met Ala Gln Leu
    130                 135                 140

Leu Arg Ile Pro Gln Ala Ile Leu Asp Met Ile Ala Gly Ala His Trp
145                 150                 155                 160
```

-continued

```
Gly Val Leu Ala Gly Ile Ala Tyr Phe Ser Met Val Gly Asn Trp Ala
                165                 170                 175

Lys Val Leu Val Val Leu Leu Leu Phe Ala Gly Val Asp Ala
            180                 185                 190


<210> SEQ ID NO 52
<211> LENGTH: 425
<212> TYPE: PRT
<213> ORGANISM: Hepatitis C Virus Isolate 1

<400> SEQUENCE: 52

Thr His Val Thr Gly Gly Ser Ala Gly His Thr Val Ser Gly Phe Val
1               5                   10                  15

Ser Leu Leu Ala Pro Gly Ala Lys Gln Asn Val Gln Leu Ile Asn Thr
            20                  25                  30

Asn Gly Ser Trp His Leu Asn Ser Thr Ala Leu Asn Cys Asn Asp Ser
        35                  40                  45

Leu Asn Thr Gly Trp Leu Ala Gly Leu Phe Tyr His His Lys Phe Asn
    50                  55                  60

Ser Ser Gly Cys Pro Glu Arg Leu Ala Ser Cys Arg Pro Leu Thr Asp
65                  70                  75                  80

Phe Asp Gln Gly Trp Gly Pro Ile Ser Tyr Ala Asn Gly Ser Gly Pro
                85                  90                  95

Asp Gln Arg Pro Tyr Cys Trp His Tyr Pro Pro Lys Pro Cys Gly Ile
            100                 105                 110

Val Pro Ala Lys Ser Val Cys Gly Pro Val Tyr Cys Phe Thr Pro Ser
        115                 120                 125

Pro Val Val Val Gly Thr Thr Asp Arg Ser Gly Ala Pro Thr Tyr Ser
    130                 135                 140

Trp Gly Glu Asn Asp Thr Asp Val Phe Val Leu Asn Asn Thr Arg Pro
145                 150                 155                 160

Pro Leu Gly Asn Trp Phe Gly Cys Thr Trp Met Asn Ser Thr Gly Phe
                165                 170                 175

Thr Lys Val Cys Gly Ala Pro Pro Cys Val Ile Gly Gly Ala Gly Asn
            180                 185                 190

Asn Thr Leu His Cys Pro Thr Asp Cys Phe Arg Lys His Pro Asp Ala
        195                 200                 205

Thr Tyr Ser Arg Cys Gly Ser Gly Pro Trp Ile Thr Pro Arg Cys Leu
    210                 215                 220

Val Asp Tyr Pro Tyr Arg Leu Trp His Tyr Pro Cys Thr Ile Asn Tyr
225                 230                 235                 240

Thr Ile Phe Lys Ile Arg Met Tyr Val Gly Gly Val Glu His Arg Leu
                245                 250                 255

Glu Ala Ala Cys Asn Trp Thr Arg Gly Glu Arg Cys Asp Leu Glu Asp
            260                 265                 270

Arg Asp Arg Ser Glu Leu Ser Pro Leu Leu Leu Thr Thr Gln Trp
        275                 280                 285

Gln Val Leu Pro Cys Ser Phe Thr Thr Leu Pro Ala Leu Ser Thr Gly
    290                 295                 300

Leu Ile His Leu His Gln Asn Ile Val Asp Val Gln Tyr Leu Tyr Gly
305                 310                 315                 320

Val Gly Ser Ser Ile Ala Ser Trp Ala Ile Lys Trp Glu Tyr Val Val
                325                 330                 335

Leu Leu Phe Leu Leu Leu Ala Asp Ala Arg Val Cys Ser Cys Leu Trp
```

-continued

```
            340                 345                 350

Met Met Leu Leu Ile Ser Gln Ala Glu Ala Ala Leu Glu Asn Leu Val
        355                 360                 365

Ile Leu Asn Ala Ala Ser Leu Ala Gly Thr His Gly Leu Val Ser Phe
    370                 375                 380

Leu Val Phe Phe Cys Phe Ala Trp Tyr Leu Lys Gly Lys Trp Val Pro
385                 390                 395                 400

Gly Ala Val Tyr Thr Phe Tyr Gly Met Trp Pro Leu Leu Leu Leu Leu
                405                 410                 415

Leu Ala Leu Pro Gln Arg Ala Tyr Ala
            420                 425


<210> SEQ ID NO 53
<211> LENGTH: 197
<212> TYPE: PRT
<213> ORGANISM: Hepatitis C Virus Isolate 1

<400> SEQUENCE: 53

Leu Asp Thr Glu Val Ala Ala Ser Cys Gly Gly Val Val Leu Val Gly
1               5                   10                  15

Leu Met Ala Leu Thr Leu Ser Pro Tyr Tyr Lys Arg Tyr Ile Ser Trp
            20                  25                  30

Cys Leu Trp Trp Leu Gln Tyr Phe Leu Thr Arg Val Glu Ala Gln Leu
        35                  40                  45

His Val Trp Ile Pro Pro Leu Asn Val Arg Gly Gly Arg Asp Ala Val
    50                  55                  60

Ile Leu Leu Met Cys Ala Val His Pro Thr Leu Val Phe Asp Ile Thr
65                  70                  75                  80

Lys Leu Leu Leu Ala Val Phe Gly Pro Leu Trp Ile Leu Gln Ala Ser
                85                  90                  95

Leu Leu Lys Val Pro Tyr Phe Val Arg Val Gln Gly Leu Leu Arg Phe
            100                 105                 110

Cys Ala Leu Ala Arg Lys Met Ile Gly Gly His Tyr Val Gln Met Val
        115                 120                 125

Ile Ile Lys Leu Gly Ala Leu Thr Gly Thr Tyr Val Tyr Asn His Leu
    130                 135                 140

Thr Pro Leu Arg Asp Trp Ala His Asn Gly Leu Arg Asp Leu Ala Val
145                 150                 155                 160

Ala Val Glu Pro Val Val Phe Ser Gln Met Glu Thr Lys Leu Ile Thr
                165                 170                 175

Trp Gly Ala Asp Thr Ala Ala Cys Gly Asp Ile Ile Asn Gly Leu Pro
            180                 185                 190

Val Ser Ala Arg Arg
        195


<210> SEQ ID NO 54
<211> LENGTH: 651
<212> TYPE: PRT
<213> ORGANISM: Hepatitis C Virus Isolate 1

<400> SEQUENCE: 54

Gly Arg Glu Ile Leu Leu Gly Pro Ala Asp Gly Met Val Ser Lys Gly
1               5                   10                  15

Trp Arg Leu Leu Ala Pro Ile Thr Ala Tyr Ala Gln Gln Thr Arg Gly
            20                  25                  30

Leu Leu Gly Cys Ile Ile Thr Ser Leu Thr Gly Arg Asp Lys Asn Gln
```

-continued

```
        35                  40                  45

Val Glu Gly Glu Val Gln Ile Val Ser Thr Ala Ala Gln Thr Phe Leu
    50                  55                  60

Ala Thr Cys Ile Asn Gly Val Cys Trp Thr Val Tyr His Gly Ala Gly
65                  70                  75                  80

Thr Arg Thr Ile Ala Ser Pro Lys Gly Pro Val Ile Gln Met Tyr Thr
                85                  90                  95

Asn Val Asp Gln Asp Leu Val Gly Trp Pro Ala Pro Gln Gly Ser Arg
            100                 105                 110

Ser Leu Thr Pro Cys Thr Cys Gly Ser Ser Asp Leu Tyr Leu Val Thr
        115                 120                 125

Arg His Ala Asp Val Ile Pro Val Arg Arg Arg Gly Asp Ser Arg Gly
    130                 135                 140

Ser Leu Leu Ser Pro Arg Pro Ile Ser Tyr Leu Lys Gly Ser Ser Gly
145                 150                 155                 160

Gly Pro Leu Leu Cys Pro Ala Gly His Ala Val Gly Ile Phe Arg Ala
                165                 170                 175

Ala Val Cys Thr Arg Gly Val Ala Lys Ala Val Asp Phe Ile Pro Val
            180                 185                 190

Glu Asn Leu Glu Thr Thr Met Arg Ser Pro Val Phe Thr Asp Asn Ser
        195                 200                 205

Ser Pro Pro Val Val Pro Gln Ser Phe Gln Val Ala His Leu His Ala
    210                 215                 220

Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255

Gly Phe Gly Ala Tyr Met Ser Lys Ala His Gly Ile Asp Pro Asn Ile
            260                 265                 270

Arg Thr Gly Val Arg Thr Ile Thr Thr Gly Ser Pro Ile Thr Tyr Ser
        275                 280                 285

Thr Tyr Gly Lys Phe Leu Ala Asp Gly Gly Cys Ser Gly Gly Ala Tyr
    290                 295                 300

Asp Ile Ile Ile Cys Asp Glu Cys His Ser Thr Asp Ala Thr Ser Ile
305                 310                 315                 320

Leu Gly Ile Gly Thr Val Leu Asp Gln Ala Glu Thr Ala Gly Ala Arg
                325                 330                 335

Leu Val Val Leu Ala Thr Ala Thr Pro Pro Gly Ser Val Thr Val Pro
            340                 345                 350

His Pro Asn Ile Glu Glu Val Ala Leu Ser Thr Thr Gly Glu Ile Pro
        355                 360                 365

Phe Tyr Gly Lys Ala Ile Pro Leu Glu Val Ile Lys Gly Gly Arg His
    370                 375                 380

Leu Ile Phe Cys His Ser Lys Lys Lys Cys Asp Glu Leu Ala Ala Lys
385                 390                 395                 400

Leu Val Ala Leu Gly Ile Asn Ala Val Ala Tyr Tyr Arg Gly Leu Asp
                405                 410                 415

Val Ser Val Ile Pro Thr Ser Gly Asp Val Val Val Val Ala Thr Asp
            420                 425                 430

Ala Leu Met Thr Gly Tyr Thr Gly Asp Phe Asp Ser Val Ile Asp Cys
        435                 440                 445

Asn Thr Cys Val Thr Gln Thr Val Asp Phe Ser Leu Asp Pro Thr Phe
    450                 455                 460
```

-continued

```
Thr Ile Glu Thr Ile Thr Leu Pro Gln Asp Ala Val Ser Arg Thr Gln
465                 470                 475                 480

Arg Arg Gly Arg Thr Gly Arg Gly Lys Pro Gly Ile Tyr Arg Phe Val
                485                 490                 495

Ala Pro Gly Glu Arg Pro Ser Gly Met Phe Asp Ser Ser Val Leu Cys
            500                 505                 510

Glu Cys Tyr Asp Ala Gly Cys Ala Trp Tyr Glu Leu Thr Pro Ala Glu
        515                 520                 525

Thr Thr Val Arg Leu Arg Ala Tyr Met Asn Thr Pro Gly Leu Pro Val
    530                 535                 540

Cys Gln Asp His Leu Glu Phe Trp Glu Gly Val Phe Thr Gly Leu Thr
545                 550                 555                 560

His Ile Asp Ala His Phe Leu Ser Gln Thr Lys Gln Ser Gly Glu Asn
                565                 570                 575

Leu Pro Tyr Leu Val Ala Tyr Gln Ala Thr Val Cys Ala Arg Ala Gln
            580                 585                 590

Ala Pro Pro Pro Ser Trp Asp Gln Met Trp Lys Cys Leu Ile Arg Leu
        595                 600                 605

Lys Pro Thr Leu His Gly Pro Thr Pro Leu Leu Tyr Arg Leu Gly Ala
    610                 615                 620

Val Gln Asn Glu Ile Thr Leu Thr His Pro Val Thr Lys Tyr Ile Met
625                 630                 635                 640

Thr Cys Met Ser Ala Asp Leu Glu Val Val Thr
                645                 650


<210> SEQ ID NO 55
<211> LENGTH: 315
<212> TYPE: PRT
<213> ORGANISM: Hepatitis C Virus Isolate 1

<400> SEQUENCE: 55

Ser Thr Trp Val Leu Val Gly Gly Val Leu Ala Ala Leu Ala Ala Tyr
1               5                   10                  15

Cys Leu Ser Thr Gly Cys Val Val Ile Val Gly Arg Val Val Leu Ser
            20                  25                  30

Gly Lys Pro Ala Ile Ile Pro Asp Arg Glu Val Leu Tyr Arg Glu Phe
        35                  40                  45

Asp Glu Met Glu Glu Cys Ser Gln His Leu Pro Tyr Ile Glu Gln Gly
    50                  55                  60

Met Met Leu Ala Glu Gln Phe Lys Gln Lys Ala Leu Gly Leu Leu Gln
65                  70                  75                  80

Thr Ala Ser Arg Gln Ala Glu Val Ile Ala Pro Ala Val Gln Thr Asn
                85                  90                  95

Trp Gln Lys Leu Glu Thr Phe Trp Ala Lys His Met Trp Asn Phe Ile
            100                 105                 110

Ser Gly Ile Gln Tyr Leu Ala Gly Leu Ser Thr Leu Pro Gly Asn Pro
        115                 120                 125

Ala Ile Ala Ser Leu Met Ala Phe Thr Ala Ala Val Thr Ser Pro Leu
    130                 135                 140

Thr Thr Ser Gln Thr Leu Leu Phe Asn Ile Leu Gly Gly Trp Val Ala
145                 150                 155                 160

Ala Gln Leu Ala Ala Pro Gly Ala Ala Thr Ala Phe Val Gly Ala Gly
                165                 170                 175

Leu Ala Gly Ala Ala Ile Gly Ser Val Gly Leu Gly Lys Val Leu Ile
```

-continued

```
        180                 185                 190

Asp Ile Leu Ala Gly Tyr Gly Ala Gly Val Ala Gly Ala Leu Val Ala
            195                 200                 205

Phe Lys Ile Met Ser Gly Glu Val Pro Ser Thr Glu Asp Leu Val Asn
    210                 215                 220

Leu Leu Pro Ala Ile Leu Ser Pro Gly Ala Leu Val Val Gly Val Val
225                 230                 235                 240

Cys Ala Ala Ile Leu Arg Arg His Val Gly Pro Gly Glu Gly Ala Val
                245                 250                 255

Gln Trp Met Asn Arg Leu Ile Ala Phe Ala Ser Arg Gly Asn His Val
            260                 265                 270

Ser Pro Thr His Tyr Val Pro Glu Ser Asp Ala Ala Ala Arg Val Thr
        275                 280                 285

Ala Ile Leu Ser Ser Leu Thr Val Thr Gln Leu Leu Arg Arg Leu His
    290                 295                 300

Gln Trp Ile Ser Ser Glu Cys Thr Thr Pro Cys
305                 310                 315


<210> SEQ ID NO 56
<211> LENGTH: 1039
<212> TYPE: PRT
<213> ORGANISM: Hepatitis C Virus Isolate 1

<400> SEQUENCE: 56

Ser Gly Ser Trp Leu Arg Asp Ile Trp Asp Trp Ile Cys Glu Val Leu
1               5                   10                  15

Ser Asp Phe Lys Thr Trp Leu Lys Ala Lys Leu Met Pro Gln Leu Pro
            20                  25                  30

Gly Ile Pro Phe Val Ser Cys Gln Arg Gly Tyr Lys Gly Val Trp Arg
        35                  40                  45

Val Asp Gly Ile Met His Thr Arg Cys His Cys Gly Ala Glu Ile Thr
    50                  55                  60

Gly His Val Lys Asn Gly Thr Met Arg Ile Val Gly Pro Arg Thr Cys
65                  70                  75                  80

Arg Asn Met Trp Ser Gly Thr Phe Pro Ile Asn Ala Tyr Thr Thr Gly
                85                  90                  95

Pro Cys Thr Pro Leu Pro Ala Pro Asn Tyr Thr Phe Ala Leu Trp Arg
            100                 105                 110

Val Ser Ala Glu Glu Tyr Val Glu Ile Arg Gln Val Gly Asp Phe His
        115                 120                 125

Tyr Val Thr Gly Met Thr Thr Asp Asn Leu Lys Cys Pro Cys Gln Val
    130                 135                 140

Pro Ser Pro Glu Phe Phe Thr Glu Leu Asp Gly Val Arg Leu His Arg
145                 150                 155                 160

Phe Ala Pro Pro Cys Lys Pro Leu Leu Arg Glu Glu Val Ser Phe Arg
                165                 170                 175

Val Gly Leu His Glu Tyr Pro Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Ala Ala Gly Arg Arg Leu Ala Arg Gly Ser Pro Pro
    210                 215                 220

Ser Val Ala Ser Ser Ser Ala Ser Gln Leu Ser Ala Pro Ser Leu Lys
225                 230                 235                 240
```

-continued

```
Ala Thr Cys Thr Ala Asn His Asp Ser Pro Asp Ala Glu Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Asp Pro Leu Val
        275                 280                 285

Ala Glu Glu Asp Glu Arg Glu Ile Ser Val Pro Ala Glu Ile Leu Arg
    290                 295                 300

Lys Ser Arg Arg Phe Ala Gln Ala Leu Pro Val Trp Ala Arg Pro Asp
305                 310                 315                 320

Tyr Asn Pro Pro Leu Val Glu Thr Trp Lys Lys Pro Asp Tyr Glu Pro
                325                 330                 335

Pro Val Val His Gly Cys Pro Leu Pro Pro Pro Lys Ser Pro Pro Val
            340                 345                 350

Pro Pro Pro Arg Lys Lys Arg Thr Val Val Leu Thr Glu Ser Thr Leu
        355                 360                 365

Ser Thr Ala Leu Ala Glu Leu Ala Thr Arg Ser Phe Gly Ser Ser Ser
    370                 375                 380

Thr Ser Gly Ile Thr Gly Asp Asn Thr Thr Thr Ser Ser Glu Pro Ala
385                 390                 395                 400

Pro Ser Gly Cys Pro Pro Asp Ser Asp Ala Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Ser Glu Ala Asn Ala Glu Asp Val Val Cys Cys
        435                 440                 445

Ser Met Ser Tyr Ser Trp Thr Gly Ala Leu Val Thr Pro Cys Ala Ala
    450                 455                 460

Glu Glu Gln Lys Leu Pro Ile Asn Ala Leu Ser Asn Ser Leu Leu Arg
465                 470                 475                 480

His His Asn Leu Val Tyr Ser Thr Thr Ser Arg Ser Ala Cys Gln Arg
                485                 490                 495

Gln Lys Lys Val Thr Phe Asp Arg Leu Gln Val Leu Asp Ser His Tyr
            500                 505                 510

Gln Asp Val Leu Lys Glu Val Lys Ala Ala Ala Ser Lys Val Lys Ala
        515                 520                 525

Asn Leu Leu Ser Val Glu Glu Ala Cys Ser Leu Thr Pro Pro His Ser
    530                 535                 540

Ala Lys Ser Lys Phe Gly Tyr Gly Ala Lys Asp Val Arg Cys His Ala
545                 550                 555                 560

Arg Lys Ala Val Thr His Ile Asn Ser Val Trp Lys Asp Leu Leu Glu
                565                 570                 575

Asp Asn Val Thr Pro Ile Asp Thr Thr Ile Met Ala Lys Asn Glu Val
            580                 585                 590

Phe Cys Val Gln Pro Glu Lys Gly Gly Arg Lys Pro Ala Arg Leu Ile
        595                 600                 605

Val Phe Pro Asp Leu Gly Val Arg Val Cys Glu Lys Met Ala Leu Tyr
    610                 615                 620

Asp Val Val Thr Lys Leu Pro Leu Ala Val Met Gly Ser Ser Tyr Gly
625                 630                 635                 640

Phe Gln Tyr Ser Pro Gly Gln Arg Val Glu Phe Leu Val Gln Ala Trp
                645                 650                 655

Lys Ser Lys Lys Thr Pro Met Gly Phe Ser Tyr Asp Thr Arg Cys Phe
```

-continued

```
            660                 665                 670

Asp Ser Thr Val Thr Glu Ser Asp Ile Arg Thr Glu Glu Ala Ile Tyr
        675                 680                 685

Gln Cys Cys Asp Leu Asp Pro Gln Ala Arg Val Ala Ile Lys Ser Leu
    690                 695                 700

Thr Glu Arg Leu Tyr Val Gly Gly Pro Leu Thr Asn Ser Arg Gly Glu
705                 710                 715                 720

Asn Cys Gly Tyr Arg Arg Cys Arg Ala Ser Gly Val Leu Thr Thr Ser
                725                 730                 735

Cys Gly Asn Thr Leu Thr Cys Tyr Ile Lys Ala Arg Ala Ala Cys Arg
            740                 745                 750

Ala Ala Gly Leu Gln Asp Cys Thr Met Leu Val Cys Gly Asp Asp Leu
        755                 760                 765

Val Val Ile Cys Glu Ser Ala Gly Val Gln Glu Asp Ala Ala Ser Leu
    770                 775                 780

Arg Ala Phe Thr Glu Ala Met Thr Arg Tyr Ser Ala Pro Pro Gly Asp
785                 790                 795                 800

Pro Pro Gln Pro Glu Tyr Asp Leu Glu Leu Ile Thr Ser Cys Ser Ser
                805                 810                 815

Asn Val Ser Val Ala His Asp Gly Ala Gly Lys Arg Val Tyr Tyr Leu
            820                 825                 830

Thr Arg Asp Pro Thr Thr Pro Leu Ala Arg Ala Ala Trp Glu Thr Ala
        835                 840                 845

Arg His Thr Pro Val Asn Ser Trp Leu Gly Asn Ile Ile Met Phe Ala
    850                 855                 860

Pro Thr Leu Trp Ala Arg Met Ile Leu Met Thr His Phe Phe Ser Val
865                 870                 875                 880

Leu Ile Ala Arg Asp Gln Leu Glu Gln Ala Leu Asp Cys Glu Ile Tyr
                885                 890                 895

Gly Ala Cys Tyr Ser Ile Glu Pro Leu Asp Leu Pro Pro Ile Ile Gln
            900                 905                 910

Arg Leu His Gly Leu Ser Ala Phe Ser Leu His Ser Tyr Ser Pro Gly
        915                 920                 925

Glu Ile Asn Arg Val Ala Ala Cys Leu Arg Lys Leu Gly Val Pro Pro
    930                 935                 940

Leu Arg Ala Trp Arg His Arg Ala Arg Ser Val Arg Ala Arg Leu Leu
945                 950                 955                 960

Ala Arg Gly Gly Arg Ala Ala Ile Cys Gly Lys Tyr Leu Phe Asn Trp
                965                 970                 975

Ala Val Arg Thr Lys Leu Lys Leu Thr Pro Ile Ala Ala Ala Gly Gln
            980                 985                 990

Leu Asp Leu Ser Gly Trp Phe Thr  Ala Gly Tyr Ser Gly  Gly Asp Ile
        995                 1000                1005

Tyr His  Ser Val Ser His Ala  Arg Pro Arg Trp Ile  Trp Phe Cys
    1010                1015                1020

Leu Leu  Leu Leu Ala Ala Gly  Val Gly Ile Tyr Leu  Leu Pro Asn
    1025                1030                1035

Arg
```